US012780949B2

(12) United States Patent
An et al.

(10) Patent No.: US 12,780,949 B2
(45) Date of Patent: Nov. 3, 2026

(54) ANTI-CLAUDIN 18.2 MULTI-SPECIFIC ANTIBODIES AND USES THEREOF

(71) Applicant: ABPRO CORPORATION, Woburn, MA (US)

(72) Inventors: Gang An, Woburn, MA (US); Zusheng Li, Woburn, MA (US); Yuan Liu, Woburn, MA (US); Adam Pelzek, Woburn, MA (US); Shaun Murphy, Woburn, MA (US); Lucy Zhang, Woburn, MA (US); Shengqin Wan, Woburn, MA (US); Yangde Chen, Woburn, MA (US); Marco Muda, Woburn, MA (US); James Lulo, Woburn, MA (US); Wei Li, Woburn, MA (US)

(73) Assignee: ABPRO CORPORATION, Burlington, MA (US)

( * ) Notice: Subject to any disclaimer, the term of this patent is extended or adjusted under 35 U.S.C. 154(b) by 790 days.

(21) Appl. No.: 18/019,728

(22) PCT Filed: Aug. 5, 2021

(86) PCT No.: PCT/US2021/044801
§ 371 (c)(1),
(2) Date: Feb. 3, 2023

(87) PCT Pub. No.: WO2022/032004
PCT Pub. Date: Feb. 10, 2022

(65) Prior Publication Data

US 2023/0279152 A1 Sep. 7, 2023

Related U.S. Application Data

(60) Provisional application No. 63/144,657, filed on Feb. 2, 2021, provisional application No. 63/074,582, filed on Sep. 4, 2020, provisional application No. 63/061,895, filed on Aug. 6, 2020.

(51) Int. Cl.

| | |
|---|---|
| ***A61P 35/00*** | (2006.01) |
| ***C07K 14/705*** | (2006.01) |
| ***C07K 16/46*** | (2006.01) |
| ***C12N 15/63*** | (2006.01) |

(52) U.S. Cl.
CPC ............ *C07K 16/468* (2013.01); *A61P 35/00* (2018.01); *C12N 15/63* (2013.01); *C07K 2317/31* (2013.01); *C07K 2317/52* (2013.01); *C07K 2317/565* (2013.01)

(58) Field of Classification Search
CPC .. A61P 35/00; C07K 14/705; C07K 2317/565
USPC ...................................................... 424/136.1
See application file for complete search history.

(56) References Cited

U.S. PATENT DOCUMENTS

| | | | |
|---|---|---|---|
| 2012/0141501 A1 | 6/2012 | Yoshida et al. |
| 2017/0298120 A1 | 10/2017 | Sasisekharan et al. |
| 2018/0318437 A1 | 11/2018 | Lerchen et al. |
| 2018/0355038 A1 | 12/2018 | Smith et al. |
| 2018/0362620 A1 | 12/2018 | Dennis et al. |
| 2019/0076525 A1 | 3/2019 | Sahin et al. |

FOREIGN PATENT DOCUMENTS

| | | |
|---|---|---|
| JP | 2020018298 A | 2/2020 |
| WO | 2010137654 A1 | 12/2010 |
| WO | 2019219089 A1 | 11/2019 |
| WO | 2019242505 A1 | 12/2019 |
| WO | 2020023679 A1 | 1/2020 |
| WO | 2020135674 * | 7/2020 |
| WO | 2020147321 A1 | 7/2020 |
| WO | 2022032003 A2 | 2/2022 |

OTHER PUBLICATIONS

U.S. Appl. No. 18/294,755, Lulo: James.*
Chen et al (J Pharm Anal. Apr. 2023;13(4):367-375. doi: 10.1016/j.jpha.2023.02.011. Epub Feb. 28, 2023).*
Effer et al (Antibodies (Basel) Mar. 12, 2024;13(1):20. doi: 10.3390/antib13010020).*
International Search Report and Written Opinion issued in PCT/US2021/044801, mailed Jan. 28, 2022, 14 pages.
International Search Report and Written Opinion issued in PCT/US2021/044801, mailed Mar. 1, 2022, 12 pages.
UniProt Accession No. A0A2S1YQL5, UniProtKB—A02AS1YQL5 (A0A2S1YQL5_(FLAO), Jul. 18, 2018, retrieved from uniprot.org/uniprot/A0A2S1YQL5 on Feb. 14, 2022.
UniProt Accession No. Q920E8, UniProtKB—Q920E8 (Q920E8_MOUSE), Dec. 1, 2001, retrieved from uniprot.org/uniprot/Q920E8 on Feb. 14, 2022.
Deli, "Potential use of tight junction modulators to reversibly open membranous barriers and improve drug delivery," Biochim Biophys Acta (2009) vol. 1788, pp. 892-910.
Furuse et al., "Claudin-1 and '2: Novel Integral Membrane Proteins Localizing at Tight Junctions with No Sequence Similarity to Occludin," J Cell Biol (1998) vol. 141, pp. 1539-1550.
Markov et al., "Claudin clusters as determinants of epithelial barrier function," IUBMB Life (2015) vol. 67, pp. 29-35.
Martin et al., "Loss of tight junction barrier function and its role in cancer metastasis," Biochim Biophys Acta (2009) vol. 1788, pp. 872-891.
Micke et al., "Aberrantly activated claudin 6 and 18.2 as potential therapy targets in non-small-cell lung cancer," Int J Cancer (2014) vol. 135, No. 9, pp. 2206-2214.
Niimi et al., "claudin-18 a Novel Downstream Target Gene for the T/EBP/NKX2.1 Homeodomain Transcription Factor, Encodes Lung- and Stomach-Specific Isoforms through Alternative Splicing," Mol Cell Biol (2001) vol. 21, No. 21, pp. 7380-7390.

(Continued)

*Primary Examiner* — Lynn A Bristol
(74) *Attorney, Agent, or Firm* — K&L Gates LLP

(57) ABSTRACT

The present disclosure relates generally to immunoglobulin-related compositions that can bind to the Claudin 18.2 protein. The multi-specific antibodies of the present technology are useful in methods for detecting and treating a Claudin 18.2-associated cancer in a subject in need thereof.

33 Claims, 29 Drawing Sheets

Specification includes a Sequence Listing.

(56) References Cited

OTHER PUBLICATIONS

Nitta et al., "Size-selective loosening of the blood-brain barrier in claudin-5-deficient mice," J Cell Biol (2003) vol. 161, pp. 653-660.
Shimobaba et al., "Claudin-18 inhibits cell proliferation and motility mediated by inhibition of phosphorylation of PDK1 and Akt in human lung adenocarcinoma A549 cells," Biochim Biophys Acta (2016) vol. 1863, pp. 1170-1178.
Singh et al., "Anti-claudin 18.2 antibody as new targeted therapy for advanced gastric cancer," J Hematol Oncol (2017) vol. 10, No. 1, Article 105, 5 pages.
Tanaka et al., "Claudin-18 Is an Early-Stage Marker of Pancreatic Carcinogenesis," J Histochem Cytochem (2011) vol. 59, No. 10, pp. 942-952.
Tokumitsu et al., "Immunocytochemistry for Claudin-18 and Maspin in biliary brushing cytology increases the accuracy of diagnosing pancreatobiliary malignancies," Cytopathology (2017) vol. 28, No. 2, pp. 116-121.

* cited by examiner h18.1-EL1 (SEQ ID NO: 1): h18.1-EL1: DMWSTQDLYDNPVTSVFQYEGLWRSCVRQSSGFTECRPYFTILGLPAMLQAVRA
h18.2-EL1 (SEQ ID NO: 2): h18.2-EL1: DQWSTQDLYNNPVTAVFNYQGLWRSCVRESSGFTECRGYFTLLGLPAMLQAVRA
m18.2-EL1 (SEQ ID NO: 2): m18.2-EL1: DQWSTQDLYNNPVTAVFNYQGLWRSCVRESSGFTECRGYFTLLGLPAMLQAVRA h18.1-EL2 (SEQ ID NO: 3): h18.1-EL2: VTNFWMSTANMYTGMGGMVQTVQTRYTFGAA
h18.2-EL2 (SEQ ID NO: 3): h18.2-EL2: VTNFWMSTANMYTGMGGMVQTVQTRYTFGAA

FIG. 2

| Clone ID | 32G4 | 47D10 | 29G4 | 31A6 | 15B10 |
|---|---|---|---|---|---|
| EC50 (nM) | 0.502 | 1.973 | 1.260 | 10.903 | 2.196 |

hCLDN18.2 (SEQ ID NO: 4):

```
        10         20         30         40         50
MAVTACQGLG FVVSLIGIAG IIAATCMDQW STQDLYNNPV TAVFNYQGLW
        60         70         80         90        100
RSCVRESSGF TECRGYFTLL GLPAMLQAVR ALMIVGIVLG AIGLLVSIFA
       110        120        130        140        150
LKCIRIGSME DSAKANMTLT SGIMFIVSGL CAIAGVSVFA NMLVTNFWMS
       160        170        180        190        200
TANMYTGMGG MVQTVQTRYT FGAALFVGWV AGGLTLIGGV MMCIACRGLA
       210        220        230        240        250
PEETNYKAVS YHASGHSVAY KPGGFKASTG FGSNTKNKKI YDGGARTEDE
       260
VQSYPSKHDY V
```

FIG. 10 hCLDN18.1 (SEQ ID NO: 5):

```
        10         20         30         40         50
MSTTTCQVVA FLLSILGLAG CIAATGMDMW STQDLYDNPV TSVFQYEGLW
        60         70         80         90        100
RSCVRQSSGF TECRPYFTIL GLPAMLQAVR ALMIVGIVLG AIGLLVSIFA
       110        120        130        140        150
LKCIRIGSME DSAKANMTLT SGIMFIVSGL CAIAGVSVFA NMLVTNFWMS
       160        170        180        190        200
TANMYTGMGG MVQTVQTRYT FGAALFVGWV AGGLTLIGGV MMCIACRGLA
       210        220        230        240        250
PEETNYKAVS YHASGHSVAY KPGGFKASTG FGSNTKNKKI YDGGARTEDE
       260
VQSYPSKHDY V
```

FIG. 11

32G4-VH CDR1 (SEQ ID NO: 6): GYSSTGYN
32G4-VH CDR2 (SEQ ID NO: 7): INPYYGGI
32G4-VH CDR3 (SEQ ID NO: 8): ARDYYGNSFAY
32G4-VL CDR1 (SEQ ID NO: 9): QSLLNSGNQKNY
32G4-VL CDR2 (SEQ ID NO: 10): WASTRES
32G4-huVL4 CDR2 (SEQ ID NO: 155): WASTLES
32G4-VL CDR3 (SEQ ID NO: 11): QNNYYFPYT

47D10-VH CDR1 (SEQ ID NO: 12): GFAFSSSA
47D10-VH CDR2 (SEQ ID NO: 13): MTVGYIYT
47D10-VH CDR3 (SEQ ID NO: 14): ARQGYGNAMDY
47D10-VL CDR1 (SEQ ID NO: 15): QSLLNSGNQKNY
47D10-VL CDR2 (SEQ ID NO: 16): WASTRES
47D10-huVL4 CDR2 (SEQ ID NO: 156): WASTRET
47D10-VL CDR3 (SEQ ID NO: 17): QNNYIYPLT

29G4-VH CDR1 (SEQ ID NO: 18): GFSLTNYG
29G4-VH CDR2 (SEQ ID NO: 19): IWAGGNT
29G4-VH CDR3 (SEQ ID NO: 20): ARGGYGNSCDY
29G4-VL CDR1 (SEQ ID NO: 21): QSLLNSGNQKNY
29G4-VL CDR2 (SEQ ID NO: 22): WASTRGS
29G4-VL CDR3 (SEQ ID NO: 23): QNDYFYPLT

31A6-VH CDR1 (SEQ ID NO: 24): GYTFASYN
31A6-VH CDR2 (SEQ ID NO: 25): IYPGKDGS
31A6-VH CDR3 (SEQ ID NO: 26): ARGGYYGNSFDY
31A6-VL CDR1 (SEQ ID NO: 27): QSLLNSGNLKNY
31A6-VL CDR2 (SEQ ID NO: 28): WASIRES
31A6-VL CDR3 (SEQ ID NO: 29): QNAYTFPFT

15B10-VH CDR1 (SEQ ID NO: 30): GYAFSNYL
15B10-VH CDR2 (SEQ ID NO: 31): IHPGSGT
15B10-VH CDR3 (SEQ ID NO: 32): SRRWYGNSLIY
15B10-VL CDR1 (SEQ ID NO: 33): QSLLNSGNQRNY
15B10-VL CDR2 (SEQ ID NO: 34): WASTRES
15B10-VL CDR3 (SEQ ID NO: 35): QNDYFYPFT

FIG. 12

32G4-VH (SEQ ID NO: 36):
EVQLQQSGPELENPGASVKIFCKASGYSSTGYNINWVKQSSGKSLEWIGNINPYYGGI
TYNQKFKGKATLTVDKSSSTAYVQLKSLTSEDSAVYYCARDYYGNSFAYWGQGTL
VTVST
32G4-VL (SEQ ID NO: 37):
DIVMTQSPSSLTVTAGEKVTMSCKSSQSLLNSGNQKNYLTWYQQNPGQPPKLLIFW
ASTRESGVPDRFTGSGSGTDFTLTISSVQAEDLAVYYCQNNYYFPYTFGGGTKLEIR

47D10-VH sequence (SEQ ID NO: 38):
QVMLVESGGGLVKPGGSLKLSCAASGFAFSSSAMSWIRQTPEKRLEWVATMTVGYI
YTYYLDTVKGRFIISRDNANNTLYLQMSSLRSEDSAMYYCARQGYGNAMDYWGQG
TSVTVSS
47D10-VL sequence (SEQ ID NO: 39):
DIVMTQSPSSLTVTAGEKVTMSCKSSQSLLNSGNQKNYLTWYQQKPGQPPKLLIYW
ASTRESGVPYRFTGSGSGTDFTLTISSVEAEDLAVYYCQNNYIYPLTFGAGTKLELK

29G4-VH sequence (SEQ ID NO: 40):
QVQLKESGPGLVAPSQTLSITCTVSGFSLTNYGVQWVRQPPGKGLEWLGVIWAGGN
TNYNSALLSRLSISKDTSKSQVFLKMNSLKTDDTAMYYCARGGYGNSCDYWGQGT
LVTVSA
29G4-VL sequence (SEQ ID NO: 41):
DIVMTQSPSSLTVTAGEKVTMNCKSSQSLLNSGNQKNYLAWYRQKPGQPPKLLIYW
ASTRGSGVPDRFTGSGSGTDFALTISSVQAEDLAVYYCQNDYFYPLTFGAGTKLDLK

31A6-VH sequence (SEQ ID NO: 42):
QTYLQQSGAELVRSGASVKMSCKASGYTFASYNIHWVKQTPGQGLEWIGYIYPGKD
GSHYNQKFRDKATLTADTSSSTAYMQISSLTSEDSAVYFCARGGYYGNSFDYWGQG
TLVTVSA
31A6-VL sequence (SEQ ID NO: 43):
DIVMSQSPSSLTVTTGEKVTMTCKSSQSLLNSGNLKNYLAWYQQKPGQPPKLLIYW
ASIRESGVPDRFTGSGSGTDFTLTIISVQAEDLAIYYCQNAYTFPFTLGGGTKLEIK

15B10-VH sequence (SEQ ID NO: 44):
QVQLQQSGAELVRPGTSVKVSCKASGYAFSNYLIDWVKQRPGQGLEWIGVIHPGSG
TNYNENFKGKATLTADKSSSTAYMQLSSLTSDDSAVYFCSRRWYGNSLIYWGQGTL
VTVSA
15B10-VL sequence (SEQ ID NO: 45):
DIVMTQSPSSLTVTAGEKVTMTCKSSQSLLNSGNQRNYLTWYQQKPGQPPKLLIYW
ASTRESGVPDRFTGSGSGTDFTLTISSVQAEDLAVYYCQNDYFYPFTFGSGTKLEIK

FIG. 13

32G4-huVH1 (SEQ ID NO: 46):
EVQLVQSGAEVKKPGASVKVSCKASGYSSTGYNINWVRQAPGQGLEWIGNINPYYGGITYNQKFQGRVTLTVDKSSSTAYMELSRLRSDDTVVYYCARDYYGNSFAYWGQGTLVTVSS

32G4-huVH2 (SEQ ID NO: 47):
QVQLVQSGAEVKKPGASVKVSCKASGYSSTGYNINWVRQAPGQGLEWMGNINPYYGGITYNQKFQGRVTMTVDKSISTAYMELSRLRSDDTVVYYCARDYYGNSFAYWGQGTLVTVSS

32G4-huVH3 (SEQ ID NO: 48):
EVQLVQSGSELKKPGASVKVSCKASGYSSTGYNINWVRQAPGQGLEWIGNINPYYGGITYNQGFTGRFVLSVDKSSSTAYLQISSLKAEDTAVYYCARDYYGNSFAYWGQGTLVTVSS

32G4-huVH4 (SEQ ID NO: 49):
QVQLVQSGSELKKPGASVKVSCKASGYSSTGYNINWVRQAPGQGLEWMGNINPYYGGITYNQGFTGRFVFSVDKSVSTAYLQISSLKAEDTAVYYCARDYYGNSFAYWGQGTLVTVSS

32G4-huVL1 (SEQ ID NO: 50):
DIVMTQSPDSLAVSLGERATINCKSSQSLLNSGNQKNYLTWYQQKPGQPPKLLIFWASTRESGVPDRFSGSGSGTDFTLTISSLQAEDVAVYYCQNNYYFPYTFGQGTKLEIK

32G4-huVL2 (SEQ ID NO: 51):
DIVMTQSPLSLPVTPGEPASISCRSSQSLLNSGNQKNYLTWYLQKPGQSPQLLIFWASTRESGVPDRFSGSGSGTDFTLKISRVEAEDVGVYYCQNNYYFPYTFGQGTKLEIK

32G4-huVL3 (SEQ ID NO: 52):
DIQMTQSPSSLSASVGDRVTITCRSSQSLLNSGNQKNYLTWYQQKPGKAPKLLIFWASTRESGVPSRFSGSGSGTDFTLTISSLQPEDFATYYCQNNYYFPYTFGQGTKLEIK

32G4-huVL4 (SEQ ID NO: 53):
DIQMTQSPSSLSASVGDRVTITCRSSQSLLNSGNQKNYLTWYQQKPGKAPKLLIFWASTLESGVPSRFSGSGSGTDFTLTISSLQPEDFATYYCQNNYYFPYTFGQGTKLEIK

FIG. 14

47D10-huVH1 (SEQ ID NO: 54):
QVMLVESGGGLVKPGGSLRLSCAASGFAFSSSAMSWIRQAPGKGLEWVATMTVGYI
YTYYLDSVKGRFTISRDNANNSLYLQMNSLRAEDTAVYYCARQGYGNAMDYWGQ
GTLVTVSS

47D10-huVH2 (SEQ ID NO: 55):
QVQLVESGGGLVKPGGSLRLSCAASGFAFSSSAMSWIRQAPGKGLEWVATMTVGYI
YTYYLDSVKGRFTISRDNAKNSLYLQMNSLRAEDTAVYYCARQGYGNAMDYWGQ
GTLVTVSS

47D10-huVH3 (SEQ ID NO: 56):
QVMLVQSGAEVKKPGASVKVSCKASGFAFSSSAMSWIRQAPGQRLEWVATMTVGY
IYTYYLDKFQGRVTITRDNANNTLYMELSSLRSEDTAVYYCARQGYGNAMDYWGQ
GTLVTVSS

47D10-huVH4 (SEQ ID NO: 57):
QVQLVQSGAEVKKPGASVKVSCKASGFAFSSSAMSWVRQAPGQRLEWMATMTVG
YIYTYYLDKFQGRVTITRDNSANTLYMELSSLRSEDTAVYYCARQGYGNAMDYWG
QGTLVTVSS

47D10-huVL1 (SEQ ID NO: 58):
DIVMTQSPDSLAVSLGERATINCKSSQSLLNSGNQKNYLTWYQQKPGQPPKLLIYWA
STRESGVPDRFSGSGSGTDFTLTISSLQAEDVAVYYCQNNYIYPLTFGQGTKLEIK

47D10-huVL2 (SEQ ID NO: 59):
DIVMTQSPLSLPVTPGEPASISCRSSQSLLNSGNQKNYLTWYLQKPGQSPQLLIYWAS
TRESGVPDRFSGSGSGTDFTLKISRVEAEDVGVYYCQNNYIYPLTFGQGTKLEIK

47D10-huVL3 (SEQ ID NO: 60):
DIVMTQSPGTLSLSPGERATLSCRSSQSLLNSGNQKNYLTWYQQKPGQAPRLLIYWA
STRESGIPDRFSGSGSGTDFTLTISRLEPEDFAVYYCQNNYIYPLTFGQGTKLEIK

47D10-huVL4 (SEQ ID NO: 61):
EIVMTQSPGTLSLSPGERATLSCRSSQSLLNSGNQKNYLTWYQQKPGQAPRLLIYWA
STRETGIPDRFSGSGSGTDFTLTISRLEPEDFAVYYCQNNYIYPLTFGQGTKLEIK

FIG. 15

32G4-huIgG1-V8

32G4-huIgG1-V8 heavy chain (SEQ ID NO: 62):
*QVQLVQSGAEVKKPGASVKVSCKASGYSSTGYNINWVRQAPGQGLEWMGNINPYYGGITY*
*NQKFQGRVTMTVDKSISTAYMELSRLRSDDTVVYYCARDYYGNSFAYWGQGTLVTVSS*AS
TKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

32G4-huIgG1-V8 light chain (SEQ ID NO: 63):
*DIQMTQSPSSLSASVGDRVTITCRSSQSLLNSGNQKNYLTWYQQKPGKAPKLLIFWASTLES*
*GVPSRFSGSGSGTDFTLTISSLQPEDFATYYCQNNYYFPYTFGQGTKLEIK*RTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC

32G4-huIgG1-V9

32G4-huIgG1-V9 heavy chain (SEQ ID NO: 64):
*EVQLVQSGSELKKPGASVKVSCKASGYSSTGYNINWVRQAPGQGLEWIGNINPYYGGITYN*
*QGFTGRFVLSVDKSSSTAYLQISSLKAEDTAVYYCARDYYGNSFAYWGQGTLVTVSS*ASTK
GPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK

32G4-huIgG1-V9 light chain (SEQ ID NO: 65):
*DIVMTQSPDSLAVSLGERATINCKSSQSLLNSGNQKNYLTWYQQKPGQPPKLLIFWASTRE*
*SGVPDRFSGSGSGTDFTLTISSLQAEDVAVYYCQNNYYFPYTFGQGTKLEIK*RTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC

FIG. 16

47D10-huIgG1-V6

47D10-huIgG1-V6 heavy chain (SEQ ID NO: 66):
*QVQLVESGGGLVKPGGSLRLSCAASGFAFSSSAMSWIRQAPGKGLEWVATMTVGYIYTYYLDSVKGRFTISRDNAKNSLYLQMNSLRAEDTAVYYCAROGYGNAMDYWGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK

47D10-huIgG1-V6 light chain (SEQ ID NO: 67):
*DIVMTQSPLSLPVTPGEPASISCRSSQSLLNSGNQKNYLTWYLQKPGQSPQLLIYWASTRESGVPDRFSGSGSGTDFTLKISRVEAEDVGVYYCQNNYIYPLTFGQGTKLEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

47D10-huIgG1-V7

47D10-huIgG1-V7 heavy chain (SEQ ID NO: 68):
*QVQLVESGGGLVKPGGSLRLSCAASGFAFSSSAMSWIRQAPGKGLEWVATMTVGYIYTYYLDSVKGRFTISRDNAKNSLYLQMNSLRAEDTAVYYCAROGYGNAMDYWGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK

47D10-huIgG1-V7 light chain (SEQ ID NO: 69):
*DIVMTQSPGTLSLSPGERATLSCRSSQSLLNSGNQKNYLTWYQQKPGQAPRLLIYWASTRESGIPDRFSGSGSGTDFTLTISRLEPEDFAVYYCQNNYIYPLTFGQGTKLEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG. 17

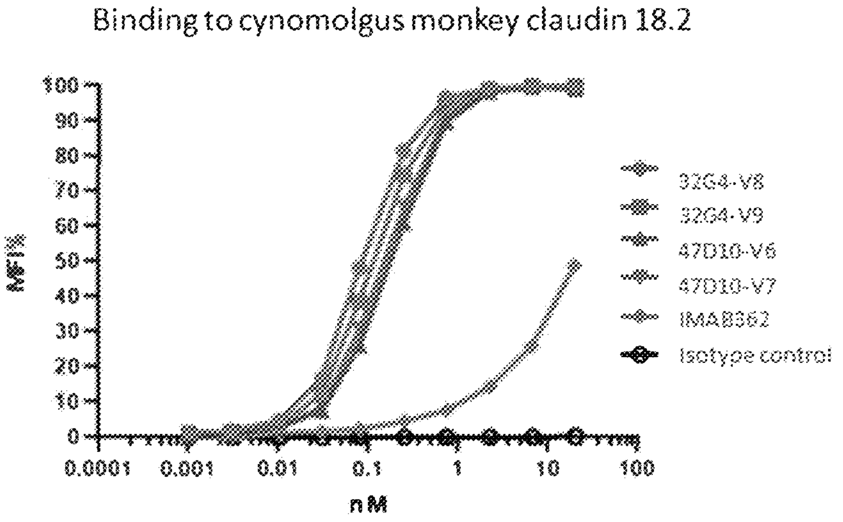
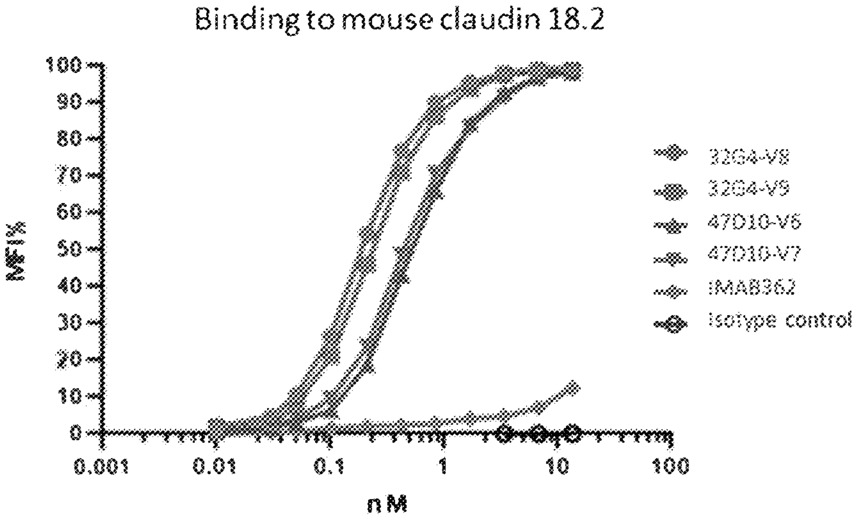
Binding to mouse and cyno claudin 18.2
| | EC50 Cyno 18.2 | EC50 Mouse 18.2 |
|---|---|---|
| 32G4-V8 | 0.087nM | 0.189nM |
| 32G4-V9 | 0.115nM | 0.231nM |
| 47D10-V6 | 0.163nM | 0.518nM |
| 47D10-V7 | 0.195nM | 0.443nM |
| IMAB362 | 144.643nM | 183.537nM |
FIG. 19

32G4-V8 x OKT3

32G4-V8 x OKT3 heavy Chain (SEQ ID NO: 81):
*QVQLVQSGAEVKKPGASVKVSCKASGYSSTGYNINWVRQAPGQGLEWMGNINPYYGGITY NQKFQGRVTMTVDKSISTAYMELSRLRSDDTVVYYCARDYYGNSFAYWGQGTLVTVSS*AS TKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPEAA GGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQ VYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGK

32G4-V8 x OKT3 light Chain (SEQ ID NO: 82):
*DIQMTQSPSSLSASVGDRVTITCRSSQSLLNSGNQKNYLTWYQQKPGKAPKLLIFWASTLES GVPSRFSGSGSGTDFTLTISSLQPEDFATYYCQNNYYFPYTFGQGTKLEIK*RTVAAPSVFIF PPSDEQLKSGTASVVCLLNNFYPREAKVQWKVDNALQSGNSQESVTEQDSKDSTYS LSSTLTLSKADYEKHKVYACEVTHQGLSSPVTKSFNRGECTSGGGGSGGGGSGGG GS*QVQLVQSGGGVVQPGRSLRLSCKASGYTFTRYTMHWVRQAPGKGLEWIGYINPSRGYT NYNQKFKDRFTISRDNSKNTAFLQMDSLRPEDTGVYFCARYYDDHYSLDYWGQGTPVTVS* SGGGGSGGGGSGGGGSGGGGSGGGGSGGGGS*DIQMTQSPSSLSASVGDRVTITCSA SSSVSYMNWYQQTPGKAPKRWIYDTSKLASGVPSRFSGSGSGTDYTFTISSLQPEDIATYYC QQWSSNPFTFGQGTKLQIT*

32G4-V9 x OKT3

32G4-V9 x OKT3 heavy chain (SEQ ID NO: 83):
*EVQLVQSGSELKKPGASVKVSCKASGYSSTGYNINWVRQAPGQGLEWIGNINPYYGGITYN QGFTGRFVLSVDKSSSTAYLQISSLKAEDTAVYYCARDYYGNSFAYWGQGTLVTVSS*ASTK GPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPEAAG GPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFF LYSKLTVDKSRWQQGNVFSCSVMHEALHNHYTQKSLSLSPGK

32G4-V9 x OKT3 light chain (SEQ ID NO: 84):
*DIVMTQSPDSLAVSLGERATINCKSSQSLLNSGNQKNYLTWYQQKPGQPPKLLIFWASTRE SGVPDRFSGSGSGTDFTLTISSLQAEDVAVYYCQNNYYFPYTFGQGTKLEIK*RTVAAPSVF IFPPSDEQLKSGTASVVCLLNNFYPREAKVQWKVDNALQSGNSQESVTEQDSKDSTY SLSSTLTLSKADYEKHKVYACEVTHQGLSSPVTKSFNRGECTSGGGGSGGGGSGGG GS*QVQLVQSGGGVVQPGRSLRLSCKASGYTFTRYTMHWVRQAPGKGLEWIGYINPSRGYT NYNQKFKDRFTISRDNSKNTAFLQMDSLRPEDTGVYFCARYYDDHYSLDYWGQGTPVTVS* SGGGGSGGGGSGGGGSGGGGSGGGGSGGGGS*DIQMTQSPSSLSASVGDRVTITCSA SSSVSYMNWYQQTPGKAPKRWIYDTSKLASGVPSRFSGSGSGTDYTFTISSLQPEDIATYYC QQWSSNPFTFGQGTKLQIT*

FIG. 20

47D10-V6 x OKT3

47D10-V6 x OKT3 heavy chain (SEQ ID NO: 85):
*QVQLVESGGGLVKPGGSLRLSCAASGFAFSSSAMSWIRQAPGKGLEWVATMTVGYIYTYYL DSVKGRFTISRDNAKNSLYLQMNSLRAEDTAVYYCARQGYGNAMDYWGQGTLVTVSS*AST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPEAA GGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQ VYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGK

47D10-V6 x OKT3 light chain (SEQ ID NO: 86):
*DIVMTQSPLSLPVTPGEPASISCRSSQSLLNSGNQKNYLTWYLQKPGQSPQLLIYWASTRES GVPDRFSGSGSGTDFTLKISRVEAEDVGVYYCQNNYIYPLTFGQGTKLEIK*RTVAAPSVFI FPPSDEQLKSGTASVVCLLNNFYPREAKVQWKVDNALQSGNSQESVTEQDSKDSTY SLSSTLTLSKADYEKHKVYACEVTHQGLSSPVTKSFNRGECTSGGGGSGGGGSGGG GS*QVQLVQSGGGVVQPGRSLRLSCKASGYTFTRYTMHWVRQAPGKGLEWIGYINPSRGYT NYNQKFKDRFTISRDNSKNTAFLQMDSLRPEDTGVYFCARYYDDHYSLDYWGQGTPVTVS S*GGGGSGGGGSGGGGSGGGGSGGGGSGGGGS*DIQMTQSPSSLSASVGDRVTITCSA SSSVSYMNWYQQTPGKAPKRWIYDTSKLASGVPSRFSGSGSGTDYTFTISSLQPEDIATYYC QQWSSNPFTFGQGTKLQIT*

47D10-V7 x OKT3

47D10-V7 x OKT3 heavy chain (SEQ ID NO: 87):
*QVQLVESGGGLVKPGGSLRLSCAASGFAFSSSAMSWIRQAPGKGLEWVATMTVGYIYTYYL DSVKGRFTISRDNAKNSLYLQMNSLRAEDTAVYYCARQGYGNAMDYWGQGTLVTVSS*AST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPEAA GGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQ VYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGK

47D10-V7 x OKT3 light chain (SEQ ID NO: 88):
*DIVMTQSPGTLSLSPGERATLSCRSSQSLLNSGNQKNYLTWYQQKPGQAPRLLIYWASTRES GIPDRFSGSGSGTDFTLTISRLEPEDFAVYYCQNNYIYPLTFGQGTKLEIK*RTVAAPSVFIF PPSDEQLKSGTASVVCLLNNFYPREAKVQWKVDNALQSGNSQESVTEQDSKDSTYS LSSTLTLSKADYEKHKVYACEVTHQGLSSPVTKSFNRGECTSGGGGSGGGGSGGG GS*QVQLVQSGGGVVQPGRSLRLSCKASGYTFTRYTMHWVRQAPGKGLEWIGYINPSRGYT NYNQKFKDRFTISRDNSKNTAFLQMDSLRPEDTGVYFCARYYDDHYSLDYWGQGTPVTVS S*GGGGSGGGGSGGGGSGGGGSGGGGSGGGGS*DIQMTQSPSSLSASVGDRVTITCSA SSSVSYMNWYQQTPGKAPKRWIYDTSKLASGVPSRFSGSGSGTDYTFTISSLQPEDIATYYC QQWSSNPFTFGQGTKLQIT*

FIG. 21

32G4-V8 x huSP34
32G4-V8 x huSP34 heavy chain (SEQ ID NO: 89):
*QVQLVQSGAEVKKPGASVKVSCKASGYSSTGYNINWVRQAPGQGLEWMGNINPYYGGITY*
*NQKFQGRVTMTVDKSISTAYMELSRLRSDDTVVYYCARDYYGNSFAYWGQGTLVTVSS*AS
TKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAA
GGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

32G4-V8 x huSP34 light chain (SEQ ID NO: 90):
*DIQMTQSPSSLSASVGDRVTITCRSSQSLLNSGNQKNYLTWYQQKPGKAPKLLIFWASTLES*
*GVPSRFSGSGSGTDFTLTISSLQPEDFATYYCQNNYYFPYTFGQGTKLEIK*RTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGECTSGGGGSGGGGSGGG
GS*EVQLVESGGGLVKPGGSLRLSCAASGFTFNTYAMNWVRQAPGKGLEWVARIRSKYNN*
*YATYYADSVKGRFTISRDDSQSSLYLQMNSLRAEDTAVYYCVRHGNFGNSYVSWFAYWGQ*
*GTLVTVSS*GGGGSGGGGSGGGGSGGGGSGGGGSGGGGS*QAVVTQEPSFSVSPGGT*
*VTLTCGSSTGAVTTSNYANWVQQTPGQAFRGLIGGTNKRAPGVPDRFSGSLIGDKAALTIT*
*GAQADDESDYFCALWYSNLWVFGGGTKLTVL*

32G4-V9 x huSP34
32G4-V9 x huSP34 heavy chain (SEQ ID NO: 91):
*EVQLVQSGSELKKPGASVKVSCKASGYSSTGYNINWVRQAPGQGLEWIGNINPYYGGITYN*
*QGFTGRFVLSVDKSSSTAYLQISSLKAEDTAVYYCARDYYGNSFAYWGQGTLVTVSS*ASTK
GPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

32G4-V9 x huSP34 light chain (SEQ ID NO: 92):
*DIVMTQSPDSLAVSLGERATINCKSSQSLLNSGNQKNYLTWYQQKPGQPPKLLIFWASTRE*
*SGVPDRFSGSGSGTDFTLTISSLQAEDVAVYYCQNNYYFPYTFGQGTKLEIK*RTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGECTSGGGGSGGGGSGGG
GS*EVQLVESGGGLVKPGGSLRLSCAASGFTFNTYAMNWVRQAPGKGLEWVARIRSKYNN*
*YATYYADSVKGRFTISRDDSQSSLYLQMNSLRAEDTAVYYCVRHGNFGNSYVSWFAYWGQ*
*GTLVTVSS*GGGGSGGGGSGGGGSGGGGSGGGGSGGGGS*QAVVTQEPSFSVSPGGT*
*VTLTCGSSTGAVTTSNYANWVQQTPGQAFRGLIGGTNKRAPGVPDRFSGSLIGDKAALTIT*
*GAQADDESDYFCALWYSNLWVFGGGTKLTVL*

FIG. 22

47D10-V6 x huSP34

47D10-V6 x huSP34 heavy chain (SEQ ID NO: 93):
QVQLVESGGGLVKPGGSLRLSCAASGFAFSSSAMSWIRQAPGKGLEWVATMTVGYIYTYYL
DSVKGRFTISRDNAKNSLYLQMNSLRAEDTAVYYCARQGYGNAMDYWGQGTLVTVSSAST
KGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAA
GGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

47D10-V6 x huSP34 light chain (SEQ ID NO: 94):
DIVMTQSPLSLPVTPGEPASISCRSSQSLLNSGNQKNYLTWYLQKPGQSPQLLIYWASTRES
GVPDRFSGSGSGTDFTLKISRVEAEDVGVYYCQNNYIYPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGECTSGGGGSGGGGSGGG
GSEVQLVESGGGLVKPGGSLRLSCAASGFTFNTYAMNWVRQAPGKGLEWVARIRSKYNN
YATYYADSVKGRFTISRDDSQSSLYLQMNSLRAEDTAVYYCVRHGNFGNSYVSWFAYWGQ
GTLVTVSSGGGGSGGGGSGGGGSGGGGSGGGGSGGGGSQAVVTQEPSFSVSPGGT
VTLTCGSSTGAVTTSNYANWVQQTPGQAFRGLIGGTNKRAPGVPDRFSGSLIGDKAALTIT
GAQADDESDYFCALWYSNLWVFGGGTKLTVL

47D10-V7 x huSP34

47D10-V7 x huSP34 heavy chain (SEQ ID NO: 95):
QVQLVESGGGLVKPGGSLRLSCAASGFAFSSSAMSWIRQAPGKGLEWVATMTVGYIYTYYL
DSVKGRFTISRDNAKNSLYLQMNSLRAEDTAVYYCARQGYGNAMDYWGQGTLVTVSSAST
KGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAA
GGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

47D10-V7 x huSP34 light chain (SEQ ID NO: 96):
DIVMTQSPGTLSLSPGERATLSCRSSQSLLNSGNQKNYLTWYQQKPGQAPRLLIYWASTRES
GIPDRFSGSGSGTDFTLTISRLEPEDFAVYYCQNNYIYPLTFGQGTKLEIKRTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGECTSGGGGSGGGGSGGG
GSEVQLVESGGGLVKPGGSLRLSCAASGFTFNTYAMNWVRQAPGKGLEWVARIRSKYNN
YATYYADSVKGRFTISRDDSQSSLYLQMNSLRAEDTAVYYCVRHGNFGNSYVSWFAYWGQ
GTLVTVSSGGGGSGGGGSGGGGSGGGGSGGGGSGGGGSQAVVTQEPSFSVSPGGT
VTLTCGSSTGAVTTSNYANWVQQTPGQAFRGLIGGTNKRAPGVPDRFSGSLIGDKAALTIT
GAQADDESDYFCALWYSNLWVFGGGTKLTVL

FIG. 23

OKT3 $V_H$ (SEQ ID NO: 97)

*QVQLVQSGGGVVQPGRSLRLSCKASGYTFTRYTMHWVRQAPGKGLEWIGYINPSRGYTNY
NQKFKDRFTISRDNSKNTAFLQMDSLRPEDTGVYFCARYYDDHYSLDYWGQGTPVTVSS*

OKT3 $V_L$ (SEQ ID NO: 98)

*DIQMTQSPSSLSASVGDRVTITCSASSSVSYMNWYQQTPGKAPKRWIYDTSKLASGVPSRFS
GSGSGTDYTFTISSLQPEDIATYYCQQWSSNPFTFGQGTKLQIT*

HuSP34 $V_H$ 1 (SEQ ID NO: 99)

*EVQLVESGGGLVQPGGSLRLSCAASGFTFNTYAMNWVRQAPGKGLEWVARIRSKYNNYAT
YYADSVKGRFTISRDDSQSSLYLQMNSLKTEDTAVYYCVRHGNFGNSYVSWFAYWGQGTL
VTVSS*

HuSP34 $V_H$ 2 (SEQ ID NO: 100)

*EVQLVESGGGLVQPGGSLRLSCAASGFTFNTYAMNWVRQAPGKGLEWVARIRSKYNNYAT
YYADSVKGRFTISRDDSKSSLYLQMNSLKTEDTAVYYCVRHGNFGNSYVSWFAYWGQGTL
VTVSS*

HuSP34 $V_H$ 3 (SEQ ID NO: 101)

*EVQLVESGGGLVKPGGSLRLSCAASGFTFNTYAMNWVRQAPGKGLEWVARIRSKYNNYAT
YYADSVKGRFTISRDDSQSSLYLQMNSLRAEDTAVYYCVRHGNFGNSYVSWFAYWGQGTL
VTVSS*

HuSP34 $V_H$ 4 (SEQ ID NO: 102)

*EVQLVESGGGLVKPGGSLRLSCAASGFTFNTYAMNWVRQAPGKGLEWVARIRSKYNNYAT
YYADSVKGRFTISRDDAKSSLYLQMNSLRAEDTAVYYCVRHGNFGNSYVSWFAYWGQGTL
VTVSS*

HuSP34 $V_H$ 5 (SEQ ID NO: 157)

*EVQLVESGGGLVQPGGSLKLSCAASGFTFNTYAMNWVRQAPGKGLEWVARIRSKYNNYAT
YYADSVKDRFTISRDDSKNTAYLQMNSLKTEDTAVYYCVRHGNFGNSYVSWFAYWGQGTL
VTVSS*

HuSP34 $V_L$ (SEQ ID NO: 103)

*QAVVTQEPSFSVSPGGTVTLTCGSSTGAVTTSNYANWVQQTPGQAFRGLIGGTNKRAPGV
PDRFSGSLIGDKAALTITGAQADDESDYFCALWYSNLWVFGGGTKLTVL*

HuSP34 $V_L$ 5 (SEQ ID NO: 158)

*QTVVTQEPSLTVSPGGTVTLTCRSSTGAVTTSNYANWVQQKPGQAFRGLIGGTNKRAPGV
PARFSGSLLGGKAALTLSGVQPEDEAIYFCALWYSNLWVFGGGTKLEIK*

FIG. 25

32G4-V8 x huSP34-v5

32G4-V8 x huSP34-v5 heavy chain (SEQ ID NO: 159)

*QVQLVQSGAEVKKPGASVKVSCKASGYSSTGYNINWVRQAPGQGLEWMGNINPYYGG*
*ITYNQKFQGRVTMTVDKSISTAYMELSRLRSDDTVVYYCARDYYGNSFAYWGQGTLVT*
*VSS*ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHT
CPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLS
LSPGK

32G4-V8 x huSP34-v5 light chain (SEQ ID NO: 160)

*DIQMTQSPSSLSASVGDRVTITCRSSQSLLNSGNQKNYLTWYQQKPGKAPKLLIFWAST*
*LESGVPSRFSGSGSGTDFTLTISSLQPEDFATYYCQNNYYFPYTFGQGTKLEIK*RTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGECTSGGGGS
GGGGSGGGGS*EVQLVESGGGLVQPGGSLKLSCAASGFTFNTYAMNWVRQAPGKGL*
*EWVARIRSKYNNYATYYADSVKDRFTISRDDSKNTAYLQMNSLKTEDTAVYYCVRHGNF*
*GNSYVSWFAYWGQGTLVTVSS*GGGGSGGGGSGGGGSGGGGSGGGGSGGGGS*Q*
*TVVTQEPSLTVSPGGTVTLTCRSSTGAVTTSNYANWVQQKPGQAFRGLIGGTNKRAPG*
*VPARFSGSLLGGKAALTLSGVQPEDEAIYFCALWYSNLWVFGGGTKLEIK*

47D10-V7 x huSP34-v5

47D10-V7 x huSP34-v5 heavy chain ((SEQ ID NO: 161)

*QVQLVESGGGLVKPGGSLRLSCAASGFAFSSSAMSWIRQAPGKGLEWVATMTVGYIYT*
*YYLDSVKGRFTISRDNAKNSLYLQMNSLRAEDTAVYYCARQGYGNAMDYWGQGTLVT*
*VSS*ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHT
CPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLS
LSPGK

47D10-V7 x huSP34-v5 light chain (SEQ ID NO: 162)

*DIVMTQSPGTLSLSPGERATLSCRSSQSLLNSGNQKNYLTWYQQKPGQAPRLLIYWAST*
*RESGIPDRFSGSGSGTDFTLTISRLEPEDFAVYYCQNNYIYPLTFGQGTKLEIK*RTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGECTSGGGGS
GGGGSGGGGS*EVQLVESGGGLVQPGGSLKLSCAASGFTFNTYAMNWVRQAPGKGL*
*EWVARIRSKYNNYATYYADSVKDRFTISRDDSKNTAYLQMNSLKTEDTAVYYCVRHGNF*
*GNSYVSWFAYWGQGTLVTVSS*GGGGSGGGGSGGGGSGGGGSGGGGSGGGGS*Q*
*TVVTQEPSLTVSPGGTVTLTCRSSTGAVTTSNYANWVQQKPGQAFRGLIGGTNKRAPG*
*VPARFSGSLLGGKAALTLSGVQPEDEAIYFCALWYSNLWVFGGGTKLEIK*

FIG. 26

| Freeze and Thaw 3 cycles | SEC-HPLC Purity | | | |
|---|---|---|---|---|
| | T0 | Cycle 1 | Cycle 2 | Cycle 3 |
| Buffer 1: 20mM sodium citrate, 0.02% PS80, pH6.0 | 95.9% | 92.3% | 92.9% | 97.4% |
| Buffer 2: 20mM sodium citrate, 5.8% sucrose, 0.02% polysorbate 80, pH7.2) | 93.8% | 92.6% | 95.1% | 97.1% |
| Buffer 3: Phosphate-buffered saline, 1X, pH 7.4) | 98.0% | 97.7% | 98.2% | 98.9% |

| 4°C | SEC-HPLC Purity | | | | |
|---|---|---|---|---|---|
| | T0 | D1 | D3 | D7 | D14 |
| Buffer 1: 20mM sodium citrate, 0.02% PS80, pH6.0 | 95.9% | 97.6% | 96.7% | 96.1% | 98.9% |
| Buffer 2: 20mM sodium citrate, 5.8% sucrose, 0.02% polysorbate 80, pH7.2) | 93.8% | 96.1% | 96.1% | 95.0% | 97.6% |
| Buffer 3: Phosphate-buffered saline, 1X, pH 7.4) | 98.0% | 98.6% | 99.3% | 98.5% | 99.8% |

| Room Temperature | SEC-HPLC Purity | | | | |
|---|---|---|---|---|---|
| | T0 | D1 | D3 | D7 | D14 |
| Buffer 1: 20mM sodium citrate, 0.02% PS80, pH6.0 | 95.9% | 96.8% | 96.5% | 97.5% | 99.0% |
| Buffer 2: 20mM sodium citrate, 5.8% sucrose, 0.02% polysorbate 80, pH7.2) | 93.8% | 95.6% | 95.9% | 96.5% | 98.3% |
| Buffer 3: Phosphate-buffered saline, 1X, pH 7.4) | 98.0% | 98.6% | 99.0% | 98.1% | 99.2% |

| 40°C | SEC-HPLC Purity | | | | |
|---|---|---|---|---|---|
| | T0 | D1 | D3 | D7 | D14 |
| Buffer 1: 20mM sodium citrate, 0.02% PS80, pH6.0 | 95.9% | 96.0% | 97.0% | 95.7% | 95.5% |
| Buffer 2: 20mM sodium citrate, 5.8% sucrose, 0.02% polysorbate 80, pH7.2) | 93.8% | 94.3% | 96.4% | 93.0% | 94.7% |
| Buffer 3: Phosphate-buffered saline, 1X, pH 7.4) | 98.0% | 97.7% | 98.0% | 95.6% | 89.0% |

FIG. 28

SEQUENCE LISTING

```
<160> NUMBER OF SEQ ID NOS: 165

<210> SEQ ID NO 1
<211> LENGTH: 54
<212> TYPE: PRT
<213> ORGANISM: Homo sapiens

<400> SEQUENCE: 1

Asp Met Trp Ser Thr Gln Asp Leu Tyr Asp Asn Pro Val Thr Ser Val
1               5                   10                  15

Phe Gln Tyr Glu Gly Leu Trp Arg Ser Cys Val Arg Gln Ser Ser Gly
            20                  25                  30

Phe Thr Glu Cys Arg Pro Tyr Phe Thr Ile Leu Gly Leu Pro Ala Met
        35                  40                  45

Leu Gln Ala Val Arg Ala
    50


<210> SEQ ID NO 2
<211> LENGTH: 54
<212> TYPE: PRT
<213> ORGANISM: Unknown
<220> FEATURE:
<223> OTHER INFORMATION: Description of Unknown:
      18.2-EL sequence

<400> SEQUENCE: 2

Asp Gln Trp Ser Thr Gln Asp Leu Tyr Asn Asn Pro Val Thr Ala Val
1               5                   10                  15

Phe Asn Tyr Gln Gly Leu Trp Arg Ser Cys Val Arg Glu Ser Ser Gly
            20                  25                  30

Phe Thr Glu Cys Arg Gly Tyr Phe Thr Leu Leu Gly Leu Pro Ala Met
        35                  40                  45

Leu Gln Ala Val Arg Ala
    50


<210> SEQ ID NO 3
<211> LENGTH: 31
<212> TYPE: PRT
<213> ORGANISM: Homo sapiens

<400> SEQUENCE: 3

Val Thr Asn Phe Trp Met Ser Thr Ala Asn Met Tyr Thr Gly Met Gly
1               5                   10                  15

Gly Met Val Gln Thr Val Gln Thr Arg Tyr Thr Phe Gly Ala Ala
            20                  25                  30


<210> SEQ ID NO 4
<211> LENGTH: 261
<212> TYPE: PRT
<213> ORGANISM: Homo sapiens

<400> SEQUENCE: 4

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60
```

Gly Tyr Phe Thr Leu Leu Gly Leu Pro Ala Met Leu Gln Ala Val Arg
65 70 75 80

Ala Leu Met Ile Val Gly Ile Val Leu Gly Ala Ile Gly Leu Leu Val
85 90 95

Ser Ile Phe Ala Leu Lys Cys Ile Arg Ile Gly Ser Met Glu Asp Ser
100 105 110

Ala Lys Ala Asn Met Thr Leu Thr Ser Gly Ile Met Phe Ile Val Ser
115 120 125

Gly Leu Cys Ala Ile Ala Gly Val Ser Val Phe Ala Asn Met Leu Val
130 135 140

Thr Asn Phe Trp Met Ser Thr Ala Asn Met Tyr Thr Gly Met Gly Gly
145 150 155 160

Met Val Gln Thr Val Gln Thr Arg Tyr Thr Phe Gly Ala Ala Leu Phe
165 170 175

Val Gly Trp Val Ala Gly Gly Leu Thr Leu Ile Gly Gly Val Met Met
180 185 190

Cys Ile Ala Cys Arg Gly Leu Ala Pro Glu Glu Thr Asn Tyr Lys Ala
195 200 205

Val Ser Tyr His Ala Ser Gly His Ser Val Ala Tyr Lys Pro Gly Gly
210 215 220

Phe Lys Ala Ser Thr Gly Phe Gly Ser Asn Thr Lys Asn Lys Lys Ile
225 230 235 240

Tyr Asp Gly Gly Ala Arg Thr Glu Asp Glu Val Gln Ser Tyr Pro Ser
245 250 255

Lys His Asp Tyr Val
260

<210> SEQ ID NO 5
<211> LENGTH: 261
<212> TYPE: PRT
<213> ORGANISM: Homo sapiens

<400> SEQUENCE: 5

Met Ser Thr Thr Thr Cys Gln Val Val Ala Phe Leu Leu Ser Ile Leu
1 5 10 15

Gly Leu Ala Gly Cys Ile Ala Ala Thr Gly Met Asp Met Trp Ser Thr
20 25 30

Gln Asp Leu Tyr Asp Asn Pro Val Thr Ser Val Phe Gln Tyr Glu Gly
35 40 45

Leu Trp Arg Ser Cys Val Arg Gln Ser Ser Gly Phe Thr Glu Cys Arg
50 55 60

Pro Tyr Phe Thr Ile Leu Gly Leu Pro Ala Met Leu Gln Ala Val Arg
65 70 75 80

Ala Leu Met Ile Val Gly Ile Val Leu Gly Ala Ile Gly Leu Leu Val
85 90 95

Ser Ile Phe Ala Leu Lys Cys Ile Arg Ile Gly Ser Met Glu Asp Ser
100 105 110

Ala Lys Ala Asn Met Thr Leu Thr Ser Gly Ile Met Phe Ile Val Ser
115 120 125

Gly Leu Cys Ala Ile Ala Gly Val Ser Val Phe Ala Asn Met Leu Val
130 135 140

Thr Asn Phe Trp Met Ser Thr Ala Asn Met Tyr Thr Gly Met Gly Gly
145 150 155 160

Met Val Gln Thr Val Gln Thr Arg Tyr Thr Phe Gly Ala Ala Leu Phe
165 170 175

```
Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Ser Ser Thr Gly Tyr Asn
1               5


<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Asn Pro Tyr Tyr Gly Gly Ile
1               5


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Asp Tyr Tyr Gly Asn Ser Phe Ala Tyr
1               5                   10


<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Leu Leu Asn Ser Gly Asn Gln Lys Asn Tyr
1               5                   10


<210> SEQ ID NO 10
<211> LENGTH: 7
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 10

Trp Ala Ser Thr Arg Glu Ser
1 5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Gln Asn Asn Tyr Tyr Phe Pro Tyr Thr
1 5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gly Phe Ala Phe Ser Ser Ser Ala
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Met Thr Val Gly Tyr Ile Tyr Thr
1 5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Ala Arg Gln Gly Tyr Gly Asn Ala Met Asp Tyr
1 5 10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gln Ser Leu Leu Asn Ser Gly Asn Gln Lys Asn Tyr
1 5 10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ala Ser Thr Arg Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Asn Asn Tyr Ile Tyr Pro Leu Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Ser Leu Thr Asn Tyr Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Trp Ala Gly Gly Asn Thr
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Gly Gly Tyr Gly Asn Ser Cys Asp Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Leu Leu Asn Ser Gly Asn Gln Lys Asn Tyr
1 5 10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Trp Ala Ser Thr Arg Gly Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gln Asn Asp Tyr Phe Tyr Pro Leu Thr
1 5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Tyr Thr Phe Ala Ser Tyr Asn
1 5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Ile Tyr Pro Gly Lys Asp Gly Ser
1 5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Ala Arg Gly Gly Tyr Tyr Gly Asn Ser Phe Asp Tyr
1 5 10

<210> SEQ ID NO 27
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gln Ser Leu Leu Asn Ser Gly Asn Leu Lys Asn Tyr
1 5 10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Trp Ala Ser Ile Arg Glu Ser
1 5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Gln Asn Ala Tyr Thr Phe Pro Phe Thr
1 5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gly Tyr Ala Phe Ser Asn Tyr Leu
1 5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Ile His Pro Gly Ser Gly Thr
1 5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Ser Arg Arg Trp Tyr Gly Asn Ser Leu Ile Tyr 1 5 10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Ser Leu Leu Asn Ser Gly Asn Gln Arg Asn Tyr
1 5 10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Trp Ala Ser Thr Arg Glu Ser
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gln Asn Asp Tyr Phe Tyr Pro Phe Thr
1 5

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Glu Val Gln Leu Gln Gln Ser Gly Pro Glu Leu Glu Asn Pro Gly Ala
1 5 10 15

Ser Val Lys Ile Phe Cys Lys Ala Ser Gly Tyr Ser Ser Thr Gly Tyr
20 25 30

Asn Ile Asn Trp Val Lys Gln Ser Ser Gly Lys Ser Leu Glu Trp Ile
35 40 45

Gly Asn Ile Asn Pro Tyr Tyr Gly Gly Ile Thr Tyr Asn Gln Lys Phe
50 55 60

Lys Gly Lys Ala Thr Leu Thr Val Asp Lys Ser Ser Ser Thr Ala Tyr
65 70 75 80

Val Gln Leu Lys Ser Leu Thr Ser Glu Asp Ser Ala Val Tyr Tyr Cys
85 90 95

Ala Arg Asp Tyr Tyr Gly Asn Ser Phe Ala Tyr Trp Gly Gln Gly Thr
100 105 110

Leu Val Thr Val Ser Thr
115

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Gln Gln Asn Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asn Tyr Tyr Phe Pro Tyr Thr Phe Gly Gly Gly Thr Lys Leu Glu Ile
100 105 110

Arg

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Gln Val Met Leu Val Glu Ser Gly Gly Gly Leu Val Lys Pro Gly Gly
1 5 10 15

Ser Leu Lys Leu Ser Cys Ala Ala Ser Gly Phe Ala Phe Ser Ser Ser
20 25 30

Ala Met Ser Trp Ile Arg Gln Thr Pro Glu Lys Arg Leu Glu Trp Val
35 40 45

Ala Thr Met Thr Val Gly Tyr Ile Tyr Thr Tyr Tyr Leu Asp Thr Val
50 55 60

Lys Gly Arg Phe Ile Ile Ser Arg Asp Asn Ala Asn Asn Thr Leu Tyr
65 70 75 80

Leu Gln Met Ser Ser Leu Arg Ser Glu Asp Ser Ala Met Tyr Tyr Cys
85 90 95

Ala Arg Gln Gly Tyr Gly Asn Ala Met Asp Tyr Trp Gly Gln Gly Thr
100 105 110

Ser Val Thr Val Ser Ser
115

<210> SEQ ID NO 39
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Tyr Arg Phe Thr Gly Ser Gly Ser Gly Thr Asp Phe Thr Leu Thr
65 70 75 80

Ile Ser Ser Val Glu Ala Glu Asp Leu Ala Val Tyr Tyr Cys Gln Asn
85 90 95

Asn Tyr Ile Tyr Pro Leu Thr Phe Gly Ala Gly Thr Lys Leu Glu Leu
100 105 110

Lys

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Gln Val Gln Leu Lys Glu Ser Gly Pro Gly Leu Val Ala Pro Ser Gln
1 5 10 15

Thr Leu Ser Ile Thr Cys Thr Val Ser Gly Phe Ser Leu Thr Asn Tyr
20 25 30

Gly Val Gln Trp Val Arg Gln Pro Pro Gly Lys Gly Leu Glu Trp Leu
35 40 45

Gly Val Ile Trp Ala Gly Gly Asn Thr Asn Tyr Asn Ser Ala Leu Leu
50 55 60

Ser Arg Leu Ser Ile Ser Lys Asp Thr Ser Lys Ser Gln Val Phe Leu
65 70 75 80

Lys Met Asn Ser Leu Lys Thr Asp Asp Thr Ala Met Tyr Tyr Cys Ala
85 90 95

Arg Gly Gly Tyr Gly Asn Ser Cys Asp Tyr Trp Gly Gln Gly Thr Leu
100 105 110

Val Thr Val Ser Ala
115

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Asp Ile Val Met Thr Gln Ser Pro Ser Ser Leu Thr Val Thr Ala Gly
1 5 10 15

Glu Lys Val Thr Met Asn Cys Lys Ser Ser Gln Ser Leu Leu Asn Ser
20 25 30

Gly Asn Gln Lys Asn Tyr Leu Ala Trp Tyr Arg Gln Lys Pro Gly Gln
35 40 45

```
Pro Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Leu Thr Phe Gly Ala Gly Thr Lys Leu Asp Leu
            100                 105                 110

Lys


<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Thr Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Ala Ser Tyr
            20                  25                  30

Asn Ile His Trp Val Lys Gln Thr Pro Gly Gln Gly Leu Glu Trp Ile
        35                  40                  45

Gly Tyr Ile Tyr Pro Gly Lys Asp Gly Ser His Tyr Asn Gln Lys Phe
    50                  55                  60

Arg Asp Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Gly Tyr Tyr Gly Asn Ser Phe Asp Tyr Trp Gly Gln Gly
            100                 105                 110

Thr Leu Val Thr Val Ser Ala
        115


<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Ser Gln Ser Pro Ser Ser Leu Thr Val Thr Thr Gly
1               5                   10                  15

Glu Lys Val Thr Met Thr Cys Lys Ser Ser Gln Ser Leu Leu Asn Ser
            20                  25                  30

Gly Asn Leu Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Thr Gly Ser Gly Ser Gly Thr Asp Phe Thr Leu Thr
65                  70                  75                  80

Ile Ile Ser Val Gln Ala Glu Asp Leu Ala Ile Tyr Tyr Cys Gln Asn
                85                  90                  95

Ala Tyr Thr Phe Pro Phe Thr Leu Gly Gly Gly Thr Lys Leu Glu Ile
```

100 105 110

Lys

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ser Asn Tyr
            20                  25                  30

Leu Ile Asp Trp Val Lys Gln Arg Pro Gly Gln Gly Leu Glu Trp Ile
        35                  40                  45

Gly Val Ile His Pro Gly Ser Gly Thr Asn Tyr Asn Glu Asn Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Asp Asp Ser Ala Val Tyr Phe Cys Ser
                85                  90                  95

Arg Arg Trp Tyr Gly Asn Ser Leu Ile Tyr Trp Gly Gln Gly Thr Leu
            100                 105                 110

Val Thr Val Ser Ala
        115
```

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Phe Thr Phe Gly Ser Gly Thr Lys Leu Glu Ile
            100                 105                 110

Lys
```

<210> SEQ ID NO 46
<211> LENGTH: 118
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 46

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Ile
        35                  40                  45

Gly Asn Ile Asn Pro Tyr Tyr Gly Gly Ile Thr Tyr Asn Gln Lys Phe
    50                  55                  60

Gln Gly Arg Val Thr Leu Thr Val Asp Lys Ser Ser Ser Thr Ala Tyr
65                  70                  75                  80

Met Glu Leu Ser Arg Leu Arg Ser Asp Asp Thr Val Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser
        115
```

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Met
        35                  40                  45

Gly Asn Ile Asn Pro Tyr Tyr Gly Gly Ile Thr Tyr Asn Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser
        115
```

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Ser Thr Gly Tyr
```

```
            20                  25                  30

Asn Ile Asn Trp Val Arg Gln Ala Pro Gly Gln Gly Leu Glu Trp Ile
        35                  40                  45

Gly Asn Ile Asn Pro Tyr Tyr Gly Gly Ile Thr Tyr Asn Gln Gly Phe
    50                  55                  60

Thr Gly Arg Phe Val Leu Ser Val Asp Lys Ser Ser Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser
        115


<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Met
        35                  40                  45

Gly Asn Ile Asn Pro Tyr Tyr Gly Gly Ile Thr Tyr Asn Gln Gly Phe
    50                  55                  60

Thr Gly Arg Phe Val Phe Ser Val Asp Lys Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser
        115


<210> SEQ ID NO 50
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
```

```
65                  70                  75                  80

Ile Ser Ser Leu Gln Ala Glu Asp Val Ala Val Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys


<210> SEQ ID NO 51
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys


<210> SEQ ID NO 52
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Phe Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys
```

<210> SEQ ID NO 53
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Leu Leu Asn Ser
20 25 30

Gly Asn Gln Lys Asn Tyr Leu Thr Trp Tyr Gln Gln Lys Pro Gly Lys
35 40 45

Ala Pro Lys Leu Leu Ile Phe Trp Ala Ser Thr Leu Glu Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Asn
85 90 95

Asn Tyr Tyr Phe Pro Tyr Thr Phe Gly Gln Gly Thr Lys Leu Glu Ile
100 105 110

Lys

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Gln Val Met Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val
50 55 60

Lys Gly Arg Phe Thr Ile Ser Arg Asp Asn Ala Asn Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Tyr Gly Asn Ala Met Asp Tyr Trp Gly Gln Gly Thr
100 105 110

Leu Val Thr Val Ser Ser
115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ser Ser
            20                  25                  30

Ala Met Ser Trp Ile Arg Gln Ala Pro Gly Lys Gly Leu Glu Trp Val
        35                  40                  45

Ala Thr Met Thr Val Gly Tyr Ile Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser
        115
```

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Gln Val Met Leu Val Gln Ser Gly Ala Glu Val Lys Lys Pro Gly Ala
1               5                   10                  15

Ser Val Lys Val Ser Cys Lys Ala Ser Gly Phe Ala Phe Ser Ser Ser
            20                  25                  30

Ala Met Ser Trp Ile Arg Gln Ala Pro Gly Gln Arg Leu Glu Trp Val
        35                  40                  45

Ala Thr Met Thr Val Gly Tyr Ile Tyr Thr Tyr Tyr Leu Asp Lys Phe
    50                  55                  60

Gln Gly Arg Val Thr Ile Thr Arg Asp Asn Ala Asn Asn Thr Leu Tyr
65                  70                  75                  80

Met Glu Leu Ser Ser Leu Arg Ser Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser
        115
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Ala Phe Ser Ser Ser
            20                  25                  30

Ala Met Ser Trp Val Arg Gln Ala Pro Gly Gln Arg Leu Glu Trp Met
        35                  40                  45
```

```
Ala Thr Met Thr Val Gly Tyr Ile Tyr Thr Tyr Tyr Leu Asp Lys Phe
    50                  55                  60

Gln Gly Arg Val Thr Ile Thr Arg Asp Asn Ser Ala Asn Thr Leu Tyr
65                  70                  75                  80

Met Glu Leu Ser Ser Leu Arg Ser Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser
        115


<210> SEQ ID NO 58
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys


<210> SEQ ID NO 59
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asn Tyr Ile Tyr Pro Leu Thr Phe Gly Gln Gly Thr Lys Leu Glu Ile
```

```
            100                 105                 110

Lys


<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys


<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Arg Leu Leu Ile Tyr Trp Ala Ser Thr Arg Glu Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys


<210> SEQ ID NO 62
<211> LENGTH: 448
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Met
        35                  40                  45

Gly Asn Ile Asn Pro Tyr Tyr Gly Gly Ile Thr Tyr Asn Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 63
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Phe Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 64
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Ser Thr Gly Tyr
            20                  25                  30
```

-continued

```
Asn Ile Asn Trp Val Arg Gln Ala Pro Gly Gln Gly Leu Glu Trp Ile
        35                  40                  45

Gly Asn Ile Asn Pro Tyr Tyr Gly Gly Ile Thr Tyr Asn Gln Gly Phe
    50                  55                  60

Thr Gly Arg Phe Val Leu Ser Val Asp Lys Ser Ser Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 65
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asn Tyr Tyr Phe Pro Tyr Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 66
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Gln Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys

```
                85                  90                  95

Ala Arg Gln Gly Tyr Gly Asn Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 67
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Asn Ser
20 25 30

Gly Asn Gln Lys Asn Tyr Leu Thr Trp Tyr Leu Gln Lys Pro Gly Gln
35 40 45

Ser Pro Gln Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Gln Asn
85 90 95

Asn Tyr Ile Tyr Pro Leu Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 68
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Gln Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Tyr Gly Asn Ala Met Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 69
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
```

```
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 70
<211> LENGTH: 384
<212> TYPE: PRT
<213> ORGANISM: Homo sapiens

<400> SEQUENCE: 70

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205
```

```
Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
    370                 375                 380
```

<210> SEQ ID NO 71
<211> LENGTH: 330
<212> TYPE: PRT
<213> ORGANISM: Homo sapiens

<400> SEQUENCE: 71

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330


<210> SEQ ID NO 72
<211> LENGTH: 326
<212> TYPE: PRT
<213> ORGANISM: Homo sapiens

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
```

```
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 73
<211> LENGTH: 377
<212> TYPE: PRT
<213> ORGANISM: Homo sapiens

<400> SEQUENCE: 73

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 74
<211> LENGTH: 452
<212> TYPE: PRT
<213> ORGANISM: Homo sapiens

<400> SEQUENCE: 74

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285
```

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 75
<211> LENGTH: 327
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu

```
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 76
<211> LENGTH: 353
<212> TYPE: PRT
<213> ORGANISM: Homo sapiens

<400> SEQUENCE: 76

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240
```

```
Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr


<210> SEQ ID NO 77
<211> LENGTH: 340
<212> TYPE: PRT
<213> ORGANISM: Homo sapiens

<400> SEQUENCE: 77

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255
```

```
Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340


<210> SEQ ID NO 78
<211> LENGTH: 106
<212> TYPE: PRT
<213> ORGANISM: Homo sapiens

<400> SEQUENCE: 78

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Gly Gly Ser Gly Gly Gly Gly Ser Gly Gly Gly Gly Ser
1               5                   10                  15


<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

```
<210> SEQ ID NO 81
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Met
        35                  40                  45

Gly Asn Ile Asn Pro Tyr Tyr Gly Gly Ile Thr Tyr Asn Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 82
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Phe Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Gln Val Gln
225                 230                 235                 240

Leu Val Gln Ser Gly Gly Gly Val Val Gln Pro Gly Arg Ser Leu Arg
                245                 250                 255

Leu Ser Cys Lys Ala Ser Gly Tyr Thr Phe Thr Arg Tyr Thr Met His
            260                 265                 270

Trp Val Arg Gln Ala Pro Gly Lys Gly Leu Glu Trp Ile Gly Tyr Ile
        275                 280                 285
```

Asn Pro Ser Arg Gly Tyr Thr Asn Tyr Asn Gln Lys Phe Lys Asp Arg
    290                 295                 300

Phe Thr Ile Ser Arg Asp Asn Ser Lys Asn Thr Ala Phe Leu Gln Met
305                 310                 315                 320

Asp Ser Leu Arg Pro Glu Asp Thr Gly Val Tyr Phe Cys Ala Arg Tyr
                325                 330                 335

Tyr Asp Asp His Tyr Ser Leu Asp Tyr Trp Gly Gln Gly Thr Pro Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gly Gly Gly
    370                 375                 380

Gly Ser Asp Ile Gln Met Thr Gln Ser Pro Ser Ser Leu Ser Ala Ser
385                 390                 395                 400

Val Gly Asp Arg Val Thr Ile Thr Cys Ser Ala Ser Ser Ser Val Ser
                405                 410                 415

Tyr Met Asn Trp Tyr Gln Gln Thr Pro Gly Lys Ala Pro Lys Arg Trp
            420                 425                 430

Ile Tyr Asp Thr Ser Lys Leu Ala Ser Gly Val Pro Ser Arg Phe Ser
        435                 440                 445

Gly Ser Gly Ser Gly Thr Asp Tyr Thr Phe Thr Ile Ser Ser Leu Gln
    450                 455                 460

Pro Glu Asp Ile Ala Thr Tyr Tyr Cys Gln Gln Trp Ser Ser Asn Pro
465                 470                 475                 480

Phe Thr Phe Gly Gln Gly Thr Lys Leu Gln Ile Thr
                485                 490

<210> SEQ ID NO 83
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Ser Thr Gly Tyr
            20                  25                  30

Asn Ile Asn Trp Val Arg Gln Ala Pro Gly Gln Gly Leu Glu Trp Ile
        35                  40                  45

Gly Asn Ile Asn Pro Tyr Tyr Gly Gly Ile Thr Tyr Asn Gln Gly Phe
    50                  55                  60

Thr Gly Arg Phe Val Leu Ser Val Asp Lys Ser Ser Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn

```
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 84
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60
```

-continued

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Gln Val Gln
225                 230                 235                 240

Leu Val Gln Ser Gly Gly Gly Val Val Gln Pro Gly Arg Ser Leu Arg
                245                 250                 255

Leu Ser Cys Lys Ala Ser Gly Tyr Thr Phe Thr Arg Tyr Thr Met His
            260                 265                 270

Trp Val Arg Gln Ala Pro Gly Lys Gly Leu Glu Trp Ile Gly Tyr Ile
        275                 280                 285

Asn Pro Ser Arg Gly Tyr Thr Asn Tyr Asn Gln Lys Phe Lys Asp Arg
    290                 295                 300

Phe Thr Ile Ser Arg Asp Asn Ser Lys Asn Thr Ala Phe Leu Gln Met
305                 310                 315                 320

Asp Ser Leu Arg Pro Glu Asp Thr Gly Val Tyr Phe Cys Ala Arg Tyr
                325                 330                 335

Tyr Asp Asp His Tyr Ser Leu Asp Tyr Trp Gly Gln Gly Thr Pro Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gly Gly Gly
    370                 375                 380

Gly Ser Asp Ile Gln Met Thr Gln Ser Pro Ser Ser Leu Ser Ala Ser
385                 390                 395                 400

Val Gly Asp Arg Val Thr Ile Thr Cys Ser Ala Ser Ser Ser Val Ser
                405                 410                 415

Tyr Met Asn Trp Tyr Gln Gln Thr Pro Gly Lys Ala Pro Lys Arg Trp
            420                 425                 430

Ile Tyr Asp Thr Ser Lys Leu Ala Ser Gly Val Pro Ser Arg Phe Ser
        435                 440                 445

Gly Ser Gly Ser Gly Thr Asp Tyr Thr Phe Thr Ile Ser Ser Leu Gln
    450                 455                 460

Pro Glu Asp Ile Ala Thr Tyr Tyr Cys Gln Gln Trp Ser Ser Asn Pro
465                 470                 475                 480

Phe Thr Phe Gly Gln Gly Thr Lys Leu Gln Ile Thr
```

485 490

<210> SEQ ID NO 85
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Gln Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Tyr Gly Asn Ala Met Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

-continued

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 86
<211> LENGTH: 492
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Asn Ser
20 25 30

Gly Asn Gln Lys Asn Tyr Leu Thr Trp Tyr Leu Gln Lys Pro Gly Gln
35 40 45

Ser Pro Gln Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Gln Asn
85 90 95

Asn Tyr Ile Tyr Pro Leu Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys Thr Ser Gly Gly
210 215 220

Gly Gly Ser Gly Gly Gly Gly Ser Gly Gly Gly Gly Ser Gln Val Gln
225 230 235 240

Leu Val Gln Ser Gly Gly Gly Val Val Gln Pro Gly Arg Ser Leu Arg
245 250 255

Leu Ser Cys Lys Ala Ser Gly Tyr Thr Phe Thr Arg Tyr Thr Met His
260 265 270

Trp Val Arg Gln Ala Pro Gly Lys Gly Leu Glu Trp Ile Gly Tyr Ile
275 280 285

Asn Pro Ser Arg Gly Tyr Thr Asn Tyr Asn Gln Lys Phe Lys Asp Arg
290 295 300

Phe Thr Ile Ser Arg Asp Asn Ser Lys Asn Thr Ala Phe Leu Gln Met
305 310 315 320

Asp Ser Leu Arg Pro Glu Asp Thr Gly Val Tyr Phe Cys Ala Arg Tyr
325 330 335

Tyr Asp Asp His Tyr Ser Leu Asp Tyr Trp Gly Gln Gly Thr Pro Val
340 345 350

Thr Val Ser Ser Gly Gly Gly Gly Ser Gly Gly Gly Gly Ser Gly Gly
355 360 365

Gly Gly Ser Gly Gly Gly Gly Ser Gly Gly Gly Gly Ser Gly Gly Gly
370 375 380

Gly Ser Asp Ile Gln Met Thr Gln Ser Pro Ser Ser Leu Ser Ala Ser
385 390 395 400

Val Gly Asp Arg Val Thr Ile Thr Cys Ser Ala Ser Ser Ser Val Ser
405 410 415

Tyr Met Asn Trp Tyr Gln Gln Thr Pro Gly Lys Ala Pro Lys Arg Trp
420 425 430

Ile Tyr Asp Thr Ser Lys Leu Ala Ser Gly Val Pro Ser Arg Phe Ser
435 440 445

Gly Ser Gly Ser Gly Thr Asp Tyr Thr Phe Thr Ile Ser Ser Leu Gln
450 455 460

Pro Glu Asp Ile Ala Thr Tyr Tyr Cys Gln Gln Trp Ser Ser Asn Pro
465 470 475 480

Phe Thr Phe Gly Gln Gly Thr Lys Leu Gln Ile Thr
485 490

<210> SEQ ID NO 87
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Gln Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Tyr Gly Asn Ala Met Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 88
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Asp Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45
```

-continued

```
Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Gln Val Gln
225                 230                 235                 240

Leu Val Gln Ser Gly Gly Gly Val Val Gln Pro Gly Arg Ser Leu Arg
                245                 250                 255

Leu Ser Cys Lys Ala Ser Gly Tyr Thr Phe Thr Arg Tyr Thr Met His
            260                 265                 270

Trp Val Arg Gln Ala Pro Gly Lys Gly Leu Glu Trp Ile Gly Tyr Ile
        275                 280                 285

Asn Pro Ser Arg Gly Tyr Thr Asn Tyr Asn Gln Lys Phe Lys Asp Arg
    290                 295                 300

Phe Thr Ile Ser Arg Asp Asn Ser Lys Asn Thr Ala Phe Leu Gln Met
305                 310                 315                 320

Asp Ser Leu Arg Pro Glu Asp Thr Gly Val Tyr Phe Cys Ala Arg Tyr
                325                 330                 335

Tyr Asp Asp His Tyr Ser Leu Asp Tyr Trp Gly Gln Gly Thr Pro Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gly Gly Gly
    370                 375                 380

Gly Ser Asp Ile Gln Met Thr Gln Ser Pro Ser Ser Leu Ser Ala Ser
385                 390                 395                 400

Val Gly Asp Arg Val Thr Ile Thr Cys Ser Ala Ser Ser Ser Val Ser
                405                 410                 415

Tyr Met Asn Trp Tyr Gln Gln Thr Pro Gly Lys Ala Pro Lys Arg Trp
            420                 425                 430

Ile Tyr Asp Thr Ser Lys Leu Ala Ser Gly Val Pro Ser Arg Phe Ser
        435                 440                 445

Gly Ser Gly Ser Gly Thr Asp Tyr Thr Phe Thr Ile Ser Ser Leu Gln
    450                 455                 460

Pro Glu Asp Ile Ala Thr Tyr Tyr Cys Gln Gln Trp Ser Ser Asn Pro
```

465 470 475 480

Phe Thr Phe Gly Gln Gly Thr Lys Leu Gln Ile Thr
485 490

<210> SEQ ID NO 89
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Ser Thr Gly Tyr
20 25 30

Asn Ile Asn Trp Val Arg Gln Ala Pro Gly Gln Gly Leu Glu Trp Met
35 40 45

Gly Asn Ile Asn Pro Tyr Tyr Gly Gly Ile Thr Tyr Asn Gln Lys Phe
50 55 60

Gln Gly Arg Val Thr Met Thr Val Asp Lys Ser Ile Ser Thr Ala Tyr
65 70 75 80

Met Glu Leu Ser Arg Leu Arg Ser Asp Asp Thr Val Val Tyr Tyr Cys
85 90 95

Ala Arg Asp Tyr Tyr Gly Asn Ser Phe Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 90
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Phe Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Lys Pro Gly Gly Ser Leu Arg
                245                 250                 255
```

Leu Ser Cys Ala Ala Ser Gly Phe Thr Phe Asn Thr Tyr Ala Met Asn
260 265 270

Trp Val Arg Gln Ala Pro Gly Lys Gly Leu Glu Trp Val Ala Arg Ile
275 280 285

Arg Ser Lys Tyr Asn Asn Tyr Ala Thr Tyr Tyr Ala Asp Ser Val Lys
290 295 300

Gly Arg Phe Thr Ile Ser Arg Asp Asp Ser Gln Ser Ser Leu Tyr Leu
305 310 315 320

Gln Met Asn Ser Leu Arg Ala Glu Asp Thr Ala Val Tyr Tyr Cys Val
325 330 335

Arg His Gly Asn Phe Gly Asn Ser Tyr Val Ser Trp Phe Ala Tyr Trp
340 345 350

Gly Gln Gly Thr Leu Val Thr Val Ser Ser Gly Gly Gly Gly Ser Gly
355 360 365

Gly Gly Gly Ser Gly Gly Gly Gly Ser Gly Gly Gly Gly Ser Gly Gly
370 375 380

Gly Gly Ser Gly Gly Gly Gly Ser Gln Ala Val Val Thr Gln Glu Pro
385 390 395 400

Ser Phe Ser Val Ser Pro Gly Gly Thr Val Thr Leu Thr Cys Gly Ser
405 410 415

Ser Thr Gly Ala Val Thr Thr Ser Asn Tyr Ala Asn Trp Val Gln Gln
420 425 430

Thr Pro Gly Gln Ala Phe Arg Gly Leu Ile Gly Gly Thr Asn Lys Arg
435 440 445

Ala Pro Gly Val Pro Asp Arg Phe Ser Gly Ser Leu Ile Gly Asp Lys
450 455 460

Ala Ala Leu Thr Ile Thr Gly Ala Gln Ala Asp Asp Glu Ser Asp Tyr
465 470 475 480

Phe Cys Ala Leu Trp Tyr Ser Asn Leu Trp Val Phe Gly Gly Gly Thr
485 490 495

Lys Leu Thr Val Leu
500

<210> SEQ ID NO 91
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

Glu Val Gln Leu Val Gln Ser Gly Ser Glu Leu Lys Lys Pro Gly Ala
1 5 10 15

Ser Val Lys Val Ser Cys Lys Ala Ser Gly Tyr Ser Ser Thr Gly Tyr
20 25 30

Asn Ile Asn Trp Val Arg Gln Ala Pro Gly Gln Gly Leu Glu Trp Ile
35 40 45

Gly Asn Ile Asn Pro Tyr Tyr Gly Gly Ile Thr Tyr Asn Gln Gly Phe
50 55 60

Thr Gly Arg Phe Val Leu Ser Val Asp Lys Ser Ser Ser Thr Ala Tyr
65 70 75 80

Leu Gln Ile Ser Ser Leu Lys Ala Glu Asp Thr Ala Val Tyr Tyr Cys
85 90 95

Ala Arg Asp Tyr Tyr Gly Asn Ser Phe Ala Tyr Trp Gly Gln Gly Thr

```
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 92
<211> LENGTH: 501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Lys Pro Gly Gly Ser Leu Arg
                245                 250                 255

Leu Ser Cys Ala Ala Ser Gly Phe Thr Phe Asn Thr Tyr Ala Met Asn
            260                 265                 270

Trp Val Arg Gln Ala Pro Gly Lys Gly Leu Glu Trp Val Ala Arg Ile
        275                 280                 285

Arg Ser Lys Tyr Asn Asn Tyr Ala Thr Tyr Tyr Ala Asp Ser Val Lys
    290                 295                 300

Gly Arg Phe Thr Ile Ser Arg Asp Asp Ser Gln Ser Ser Leu Tyr Leu
305                 310                 315                 320

Gln Met Asn Ser Leu Arg Ala Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Gly Gly Gly Gly Ser Gly
        355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gln Ala Val Val Thr Gln Glu Pro
385                 390                 395                 400

Ser Phe Ser Val Ser Pro Gly Gly Thr Val Thr Leu Thr Cys Gly Ser
                405                 410                 415

Ser Thr Gly Ala Val Thr Thr Ser Asn Tyr Ala Asn Trp Val Gln Gln
            420                 425                 430

Thr Pro Gly Gln Ala Phe Arg Gly Leu Ile Gly Gly Thr Asn Lys Arg
```

```
        435                 440                 445

Ala Pro Gly Val Pro Asp Arg Phe Ser Gly Ser Leu Ile Gly Asp Lys
    450                 455                 460

Ala Ala Leu Thr Ile Thr Gly Ala Gln Ala Asp Asp Glu Ser Asp Tyr
465                 470                 475                 480

Phe Cys Ala Leu Trp Tyr Ser Asn Leu Trp Val Phe Gly Gly Gly Thr
                485                 490                 495

Lys Leu Thr Val Leu
            500


<210> SEQ ID NO 93
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ser Ser
            20                  25                  30

Ala Met Ser Trp Ile Arg Gln Ala Pro Gly Lys Gly Leu Glu Trp Val
        35                  40                  45

Ala Thr Met Thr Val Gly Tyr Ile Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 94
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

Ser Pro Val Thr Lys Ser Phe Asn Arg Gly Glu Cys Thr Ser Gly Gly
210 215 220

Gly Gly Ser Gly Gly Gly Gly Ser Gly Gly Gly Gly Ser Glu Val Gln
225 230 235 240

Leu Val Glu Ser Gly Gly Gly Leu Val Lys Pro Gly Gly Ser Leu Arg
245 250 255

Leu Ser Cys Ala Ala Ser Gly Phe Thr Phe Asn Thr Tyr Ala Met Asn
260 265 270

Trp Val Arg Gln Ala Pro Gly Lys Gly Leu Glu Trp Val Ala Arg Ile
275 280 285

Arg Ser Lys Tyr Asn Asn Tyr Ala Thr Tyr Tyr Ala Asp Ser Val Lys
290 295 300

Gly Arg Phe Thr Ile Ser Arg Asp Asp Ser Gln Ser Ser Leu Tyr Leu
305 310 315 320

Gln Met Asn Ser Leu Arg Ala Glu Asp Thr Ala Val Tyr Tyr Cys Val
325 330 335

Arg His Gly Asn Phe Gly Asn Ser Tyr Val Ser Trp Phe Ala Tyr Trp
340 345 350

Gly Gln Gly Thr Leu Val Thr Val Ser Ser Gly Gly Gly Gly Ser Gly
355 360 365

Gly Gly Gly Ser Gly Gly Gly Gly Ser Gly Gly Gly Gly Ser Gly Gly
370 375 380

Gly Gly Ser Gly Gly Gly Gly Ser Gln Ala Val Val Thr Gln Glu Pro
385 390 395 400

Ser Phe Ser Val Ser Pro Gly Gly Thr Val Thr Leu Thr Cys Gly Ser
405 410 415

Ser Thr Gly Ala Val Thr Thr Ser Asn Tyr Ala Asn Trp Val Gln Gln
420 425 430

Thr Pro Gly Gln Ala Phe Arg Gly Leu Ile Gly Gly Thr Asn Lys Arg
435 440 445

Ala Pro Gly Val Pro Asp Arg Phe Ser Gly Ser Leu Ile Gly Asp Lys
450 455 460

Ala Ala Leu Thr Ile Thr Gly Ala Gln Ala Asp Asp Glu Ser Asp Tyr
465 470 475 480

Phe Cys Ala Leu Trp Tyr Ser Asn Leu Trp Val Phe Gly Gly Gly Thr
485 490 495

Lys Leu Thr Val Leu
500

<210> SEQ ID NO 95
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 95

Gln Val Gln Leu Val Glu Ser Gly Gly Gly Leu Val Lys Pro Gly Gly
1 5 10 15

Ser Leu Arg Leu Ser Cys Ala Ala Ser Gly Phe Ala Phe Ser Ser Ser
20 25 30

Ala Met Ser Trp Ile Arg Gln Ala Pro Gly Lys Gly Leu Glu Trp Val
35 40 45

Ala Thr Met Thr Val Gly Tyr Ile Tyr Thr Tyr Tyr Leu Asp Ser Val

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 96
<211> LENGTH: 501
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 96

```
Asp Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Lys Pro Gly Gly Ser Leu Arg
                245                 250                 255

Leu Ser Cys Ala Ala Ser Gly Phe Thr Phe Asn Thr Tyr Ala Met Asn
            260                 265                 270

Trp Val Arg Gln Ala Pro Gly Lys Gly Leu Glu Trp Val Ala Arg Ile
        275                 280                 285

Arg Ser Lys Tyr Asn Asn Tyr Ala Thr Tyr Tyr Ala Asp Ser Val Lys
    290                 295                 300

Gly Arg Phe Thr Ile Ser Arg Asp Asp Ser Gln Ser Ser Leu Tyr Leu
305                 310                 315                 320

Gln Met Asn Ser Leu Arg Ala Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Gly Gly Gly Gly Ser Gly
        355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gln Ala Val Val Thr Gln Glu Pro
```

385 390 395 400

Ser Phe Ser Val Ser Pro Gly Gly Thr Val Thr Leu Thr Cys Gly Ser
405 410 415

Ser Thr Gly Ala Val Thr Thr Ser Asn Tyr Ala Asn Trp Val Gln Gln
420 425 430

Thr Pro Gly Gln Ala Phe Arg Gly Leu Ile Gly Gly Thr Asn Lys Arg
435 440 445

Ala Pro Gly Val Pro Asp Arg Phe Ser Gly Ser Leu Ile Gly Asp Lys
450 455 460

Ala Ala Leu Thr Ile Thr Gly Ala Gln Ala Asp Asp Glu Ser Asp Tyr
465 470 475 480

Phe Cys Ala Leu Trp Tyr Ser Asn Leu Trp Val Phe Gly Gly Gly Thr
485 490 495

Lys Leu Thr Val Leu
500

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Gln Val Gln Leu Val Gln Ser Gly Gly Gly Val Val Gln Pro Gly Arg
1 5 10 15

Ser Leu Arg Leu Ser Cys Lys Ala Ser Gly Tyr Thr Phe Thr Arg Tyr
20 25 30

Thr Met His Trp Val Arg Gln Ala Pro Gly Lys Gly Leu Glu Trp Ile
35 40 45

Gly Tyr Ile Asn Pro Ser Arg Gly Tyr Thr Asn Tyr Asn Gln Lys Phe
50 55 60

Lys Asp Arg Phe Thr Ile Ser Arg Asp Asn Ser Lys Asn Thr Ala Phe
65 70 75 80

Leu Gln Met Asp Ser Leu Arg Pro Glu Asp Thr Gly Val Tyr Phe Cys
85 90 95

Ala Arg Tyr Tyr Asp Asp His Tyr Ser Leu Asp Tyr Trp Gly Gln Gly
100 105 110

Thr Pro Val Thr Val Ser Ser
115

<210> SEQ ID NO 98
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Thr Pro Gly Lys Ala Pro Lys Arg Trp Ile Tyr
35 40 45

Asp Thr Ser Lys Leu Ala Ser Gly Val Pro Ser Arg Phe Ser Gly Ser

```
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105


<210> SEQ ID NO 99
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Gln Ser Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
```

115 120 125

<210> SEQ ID NO 101
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 101

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Gln Ser Ser
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 102
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ala Lys Ser Ser
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Gln Ala Val Val Thr Gln Glu Pro Ser Phe Ser Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Asp Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Asp Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
tgggtatctg gtacctgtgg g 21

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
aggctgttgg tgctgatgtt ctggatt 27

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
ctcttggtgc ttctgttgtt ctggattcct 30

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
ctgttagtgc tctggattcg ggaaacc 27

<210> SEQ ID NO 108

<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
gggctgcttk tgytctgkat cyct 24

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
ctagggstgc tkvtrctctg gatcccwggw 30

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
ctgytatggg trctgckgct ctgg 24

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ttsytgctaa tcagtgycwc agtyryaatg 30

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
gtcacagtca tagtgtctaa tgga 24

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
ggkctcytgt tgctctgkyt tcmwggt 27

<210> SEQ ID NO 114
<211> LENGTH: 27

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggmwtcttgt tgctctggtt tccaggt 27

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
caggtcctgg sgttgctgct gctg 24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tttctactgc tctgtgtgtc tggt 24

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ytkctstggt trtmtggwgy tgawggr 27

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cagktyytbg krytyytkct kytctgg 27

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ctgctaatca gtgcctcagt cataatatcc 30

<210> SEQ ID NO 120
<211> LENGTH: 27
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 120
ttcagcttcc tgctaatcag tgcytca 27

<210> SEQ ID NO 121
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ctrtkggtgc tgmtgytctg grttccw 27

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ttgctctkkt ttcmaggtay caratgt 27

<210> SEQ ID NO 123
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cagttcctgt ttctgttagt gctctgg 27

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
caggtcytkg yrttsstgyt kctstgg 27

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gccaccatgg rywthmrrrt g 21

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
actggatggt gggaagat 18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aggggccagt ggatagac 18

<210> SEQ ID NO 128
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
atagacagat gggggtgtcg ttttggc 27

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cttgaccagg catcctagag tca 23

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
aggggccagt ggatagactg atgg 24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
agggaccaag ggatagacag atgg 24

<210> SEQ ID NO 132
<211> LENGTH: 20
<212> TYPE: DNA
<213> ORGANISM: Artificial Sequence
<220> FEATURE:

<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, g or t

<400> SEQUENCE: 132
sargtnmagc tgsagsagtc 20

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, g or t

<400> SEQUENCE: 133
sargtnmagc tgsagsagtc wgg 23

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gayattgtgm tsacmcarwc tmca 24

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ggatggtggg aagatggata cagttggtgc 30

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
atgatggtgt taagtcttct gtacctg 27

<210> SEQ ID NO 137
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctgttsacag ycyttcckgg tatcctg 27

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 138
rcattyccaa gctgtrtcct dtcc 24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 139
ctgctgmytg tccctgcata tgtc 24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 140
ctcytgtcag daactgcagg ygtc 24

<210> SEQ ID NO 141
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 141
atgggatgga gcygkatcwt bctctty 27

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 142
cactggatct ttctctccct g 21

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 143
atgggatgga gctatatcwt bctctty 27

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 144
gcaacagcyw ymggtgtcca ctcc 24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 145
ctgatggcag tggttayagg ggtc 24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 146
kcadyarcta caggtgyyca ctcc 24

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 147
cttttamawg gtrtccagtg t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 148
gctcttttaa aaggggtcca g 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 149
ctgagctgtg ywttyattrt t 21

```
<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150

cttgtcsttv ttttaaaagg tgtc                                            24


<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151

atgctgttag ggctggtttt c                                               21


<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152

ttcctgatgg cagctgccca aagt                                            24


<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153

ctgttsacag ccwttcctgg t                                               21


<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154

ctggcattac tcttctgcct g                                               21


<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Trp Ala Ser Thr Leu Glu Ser
1               5
```

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Trp Ala Ser Thr Arg Glu Thr
1               5

<210> SEQ ID NO 157
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 158
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Ile Tyr Phe Cys Ala Leu Trp Tyr Ser Asn
                85                  90                  95

Leu Trp Val Phe Gly Gly Gly Thr Lys Leu Glu Ile Lys
            100                 105

<210> SEQ ID NO 159
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 159

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Ser Thr Gly Tyr
20 25 30

Asn Ile Asn Trp Val Arg Gln Ala Pro Gly Gln Gly Leu Glu Trp Met
35 40 45

Gly Asn Ile Asn Pro Tyr Tyr Gly Gly Ile Thr Tyr Asn Gln Lys Phe
50 55 60

Gln Gly Arg Val Thr Met Thr Val Asp Lys Ser Ile Ser Thr Ala Tyr
65 70 75 80

Met Glu Leu Ser Arg Leu Arg Ser Asp Asp Thr Val Val Tyr Tyr Cys
85 90 95

Ala Arg Asp Tyr Tyr Gly Asn Ser Phe Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys

```
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 160
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Phe Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asn Tyr Tyr Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Gln Pro Gly Gly Ser Leu Lys
                245                 250                 255

Leu Ser Cys Ala Ala Ser Gly Phe Thr Phe Asn Thr Tyr Ala Met Asn
            260                 265                 270
```

```
Trp Val Arg Gln Ala Pro Gly Lys Gly Leu Glu Trp Val Ala Arg Ile
        275                 280                 285

Arg Ser Lys Tyr Asn Asn Tyr Ala Thr Tyr Tyr Ala Asp Ser Val Lys
    290                 295                 300

Asp Arg Phe Thr Ile Ser Arg Asp Asp Ser Lys Asn Thr Ala Tyr Leu
305                 310                 315                 320

Gln Met Asn Ser Leu Lys Thr Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Gly Gly Gly Gly Ser Gly
        355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Arg Ser
                405                 410                 415

Ser Thr Gly Ala Val Thr Thr Ser Asn Tyr Ala Asn Trp Val Gln Gln
            420                 425                 430

Lys Pro Gly Gln Ala Phe Arg Gly Leu Ile Gly Gly Thr Asn Lys Arg
        435                 440                 445

Ala Pro Gly Val Pro Ala Arg Phe Ser Gly Ser Leu Leu Gly Gly Lys
    450                 455                 460

Ala Ala Leu Thr Leu Ser Gly Val Gln Pro Glu Asp Glu Ala Ile Tyr
465                 470                 475                 480

Phe Cys Ala Leu Trp Tyr Ser Asn Leu Trp Val Phe Gly Gly Gly Thr
                485                 490                 495

Lys Leu Glu Ile Lys
            500


<210> SEQ ID NO 161
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ser Ser
            20                  25                  30

Ala Met Ser Trp Ile Arg Gln Ala Pro Gly Lys Gly Leu Glu Trp Val
        35                  40                  45

Ala Thr Met Thr Val Gly Tyr Ile Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 162
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Val Met Thr Gln Ser Pro Gly Thr Leu Ser Leu Ser Pro Gly
1               5                   10                  15

Glu Arg Ala Thr Leu Ser Cys Arg Ser Ser Gln Ser Leu Leu Asn Ser
            20                  25                  30

Gly Asn Gln Lys Asn Tyr Leu Thr Trp Tyr Gln Gln Lys Pro Gly Gln
```

-continued

```
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Asn
                85                  90                  95

Asn Tyr Ile Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Gln Pro Gly Gly Ser Leu Lys
                245                 250                 255

Leu Ser Cys Ala Ala Ser Gly Phe Thr Phe Asn Thr Tyr Ala Met Asn
            260                 265                 270

Trp Val Arg Gln Ala Pro Gly Lys Gly Leu Glu Trp Val Ala Arg Ile
        275                 280                 285

Arg Ser Lys Tyr Asn Asn Tyr Ala Thr Tyr Tyr Ala Asp Ser Val Lys
    290                 295                 300

Asp Arg Phe Thr Ile Ser Arg Asp Asp Ser Lys Asn Thr Ala Tyr Leu
305                 310                 315                 320

Gln Met Asn Ser Leu Lys Thr Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Gly Gly Gly Gly Ser Gly
        355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Arg Ser
                405                 410                 415

Ser Thr Gly Ala Val Thr Thr Ser Asn Tyr Ala Asn Trp Val Gln Gln
            420                 425                 430

Lys Pro Gly Gln Ala Phe Arg Gly Leu Ile Gly Gly Thr Asn Lys Arg
        435                 440                 445

Ala Pro Gly Val Pro Ala Arg Phe Ser Gly Ser Leu Leu Gly Gly Lys
    450                 455                 460
```

```
Ala Ala Leu Thr Leu Ser Gly Val Gln Pro Glu Asp Glu Ala Ile Tyr
465                 470                 475                 480

Phe Cys Ala Leu Trp Tyr Ser Asn Leu Trp Val Phe Gly Gly Gly Thr
                485                 490                 495

Lys Leu Glu Ile Lys
            500


<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Gly Gly Ser
1               5


<210> SEQ ID NO 164
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(75)
<223> OTHER INFORMATION: This sequence may encompass 1-15 "Gly Gly Gly
      Gly Ser" repeating units
<220> FEATURE:
<223> OTHER INFORMATION: See specification as filed for detailed
      description of substitutions and preferred embodiments

<400> SEQUENCE: 164

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser
65                  70                  75


<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 165

His His His His His His
1               5
```

ANTI-CLAUDIN 18.2 MULTI-SPECIFIC ANTIBODIES AND USES THEREOF

CROSS-REFERENCE TO RELATED APPLICATIONS

This application is a U.S. National Phase Application under 35 U.S.C. § 371 of International Application No. PCT/US2021/044801, filed Aug. 5, 2021, which claims the benefit of and priority to U.S. Provisional Appl. No. 63/061,895, filed Aug. 6, 2020, U.S. Provisional Appl. No. 63/074,582, filed Sep. 4, 2020, and U.S. Provisional Appl. No. 63/144,657, filed Feb. 2, 2021, the disclosures of which are hereby incorporated by reference herein in their entirety.

SEQUENCE LISTING

The instant application contains a Sequence Listing which has been submitted electronically in ASCII format and is hereby incorporated by reference in its entirety. Said ASCII copy, created on Sep. 16, 2021, is named 106105-0627_SL.txt and is 201,070 bytes in size.

TECHNICAL FIELD

The present technology relates generally to the preparation of immunoglobulin-related compositions (e.g., multi-specific antibodies or antigen binding fragments thereof) that specifically bind Claudin 18.2 protein and uses of the same. In particular, the present technology relates to the preparation of Claudin 18.2 binding multi-specific antibodies and their use in detecting and treating cancer.

BACKGROUND

The following description of the background of the present technology is provided simply as an aid in understanding the present technology and is not admitted to describe or constitute prior art to the present technology.

Claudins are integral membrane proteins that form tight junctions. Tight junctions serve as a physical barrier to prevent solutes and water from passing freely through the intercellular space between epithelial or endothelial cell sheets (Markov, A. G., et al., *IUBMB Life* 67:29-35 (2015); Furuse, M., et al., *J Cell Biol* 141:1539-1550 (1998); Nitta, T., et al., *J Cell Biol* 161:653-660 (2003); Deli, M. A., *Biochim Biophys Acta* 1788:892-910 (2009)). Additionally, tight junctions also play critical roles in maintaining cell polarity and signal transduction. Disruption of the cellular polarity of the epithelium is an early event in malignant transformation (Martin, T. A. And Jiang, W. G., *Biochim Biophys Acta* 1788:872-891 (2009)). Claudin 18.2 is abundant in a significant proportion of primary gastric cancers and its metastases, and plays an important role in their malignant transformation. For example, frequent ectopic activation of claudin 18.2 was found in pancreatic, esophageal, ovarian, and lung tumors (Niimi et al., (2001) *Mol Cell Biol* 21 (21): 7380-7390; Tanaka et al. (2011) *J Histochem Cytochem* 59 (10): 942-952; Micke et al., (2014) *Int J Cancer* 135 (9): 2206-2214; Shimobaba et al. (2016) *Biochim Biophys Acta* 1863 (6 Pt A): 1170-1178; Singh et al., (2017) *J Hematol Oncol* 10 (1): 105; Tokumitsu et al., (2017) *Cytopathology* 28 (2): 116-121).

Accordingly, there is an urgent need for novel anti-Claudin 18.2 immunoglobulin-related compositions that are effective in treating Claudin 18.2-associated malignancies.

SUMMARY OF THE PRESENT TECHNOLOGY

In one aspect, the present disclosure provides a multi-specific (e.g., bispecific) antibody or an antigen binding fragment thereof, comprising a first antigen binding moiety that binds a Claudin 18.2 epitope and at least a second antigen binding moiety that binds to a second epitope, wherein the first antigen binding moiety comprises a first heavy chain immunoglobulin variable domain ($V_H$) and a first light chain immunoglobulin variable domain ($V_L$), wherein the second antigen binding moiety comprises a second $V_H$ and a second $V_L$, and wherein (a) the first $V_H$ comprises a $V_H$-CDR1 sequence selected from the group consisting of SEQ ID NOs: 6, 12, 18, 24 and 30, a $V_H$-CDR2 sequence selected from the group consisting of SEQ ID NOs: 7, 13, 19, 25, and 31, and a $V_H$-CDR3 sequence selected from the group consisting of SEQ ID NOs: 8, 14, 20, 26, and 32, and/or (b) the first $V_L$ comprises a $V_L$-CDR1 sequence selected from the group consisting of SEQ ID NOs: 9, 15, 21, 27, and 33, a $V_L$-CDR2 sequence selected from the group consisting of SEQ ID NOs: 10, 16, 22, 28, 34, 155 and 156, and a $V_L$-CDR3 sequence selected from the group consisting of SEQ ID NOs: 11, 17, 23, 29, and 35.

In one aspect, the present disclosure provides a multi-specific (e.g., bispecific) antibody or an antigen binding fragment thereof, comprising a first antigen binding moiety that binds a claudin 18.2 epitope and at least a second antigen binding moiety that binds to a second epitope, wherein the first antigen binding moiety comprises a first heavy chain immunoglobulin variable domain ($V_H$) and a first light chain immunoglobulin variable domain ($V_L$), wherein the second antigen binding moiety comprises a second $V_H$ and a second $V_L$, and wherein (a) the first $V_H$ comprises a $V_H$-CDR1 sequence of SEQ ID NO: 6, a $V_H$-CDR2 sequence of SEQ ID NO: 7, and a $V_H$-CDR3 sequence of SEQ ID NO: 8, and/or the first $V_L$ comprises a $V_L$-CDR1 sequence of SEQ ID NO: 9, a $V_L$-CDR2 sequence of SEQ ID NO: 10 or SEQ ID NO: 155, and a $V_L$-CDR3 sequence of SEQ ID NO: 11; (b) the first $V_H$ comprises a $V_H$-CDR1 sequence of SEQ ID NO: 12, a $V_H$-CDR2 sequence of SEQ ID NO: 13, and a $V_H$-CDR3 sequence of SEQ ID NO: 14, and/or the first $V_L$ comprises a $V_L$-CDR1 sequence of SEQ ID NO: 15, a $V_L$-CDR2 sequence of SEQ ID NO: 16 or SEQ ID NO: 156, and a $V_L$-CDR3 sequence of SEQ ID NO: 17; (c) the first $V_H$ comprises a $V_H$-CDR1 sequence of SEQ ID NO: 18, a $V_H$-CDR2 sequence of SEQ ID NO: 19, and a $V_H$-CDR3 sequence of SEQ ID NO: 20, and/or the first $V_L$ comprises a $V_L$-CDR1 sequence of SEQ ID NO: 21, a $V_L$-CDR2 sequence of SEQ ID NO: 22, and a $V_L$-CDR3 sequence of SEQ ID NO: 23; (d) the first $V_H$ comprises a $V_H$-CDR1 sequence of SEQ ID NO: 24, a $V_H$-CDR2 sequence of SEQ ID NO: 25, and a $V_H$-CDR3 sequence of SEQ ID NO: 26, and/or the first $V_L$ comprises a $V_L$-CDR1 sequence of SEQ ID NO: 27, a $V_L$-CDR2 sequence of SEQ ID NO: 28, and a $V_L$-CDR3 sequence of SEQ ID NO: 29; or (e) the first $V_H$ comprises a $V_H$-CDR1 sequence of SEQ ID NO: 30, a $V_H$-CDR2 sequence of SEQ ID NO: 31, and a $V_H$-CDR3 sequence of SEQ ID NO: 32, and/or the first $V_L$ comprises a $V_L$-CDR1 sequence of SEQ ID NO: 33, a $V_L$-CDR2 sequence of SEQ ID NO: 34, and a $V_L$-CDR3 sequence of SEQ ID NO: 35.

In one aspect, the present disclosure provides a multi-specific (e.g., bispecific) antibody or an antigen binding fragment thereof, comprising a first antigen binding moiety that binds a claudin 18.2 epitope and at least a second antigen binding moiety that binds to a second epitope, wherein the first antigen binding moiety comprises a first heavy chain immunoglobulin variable domain ($V_H$) and a first light chain immunoglobulin variable domain ($V_L$), wherein the second antigen binding moiety comprises a second $V_H$ and a second $V_L$, and wherein the first $V_H$ comprises an amino acid sequence selected from any one of SEQ ID NOs: 36, 38, 40, 42, 44, 46-49, or 54-57; and/or (b) the first $V_L$ comprises an amino acid sequence selected from any one of SEQ ID NOs: 37, 39, 41, 43, 45, 50-53, or 58-61.

Additionally or alternatively, in some embodiments of the multi-specific (e.g., bispecific) antibody or antigen binding fragment disclosed herein, the second $V_H$ comprises an amino acid sequence selected from any one of SEQ ID NOs: 97, 99, 100, 101, 102, or 157; and/or (b) the second $V_L$ comprises an amino acid sequence selected from any one of SEQ ID NOs: 98, 103, or 158.

In any and all embodiments of the multi-specific (e.g., bispecific) antibody or antigen binding fragment disclosed herein, the multi-specific (e.g., bispecific) antigen binding fragment may be selected from the group consisting of Fab, $F(ab')_2$, Fab', $scF_v$, and $F_v$.

Additionally or alternatively, in some embodiments, the multi-specific (e.g., bispecific) antibody or antigen binding fragment further comprises a Fc domain of an isotype selected from the group consisting of IgG1, IgG2, IgG3, IgG4, IgA1, IgA2, IgM, IgD, and IgE. In certain embodiments, the multi-specific (e.g., bispecific) antibody or antigen binding fragment comprises an IgG1 constant region comprising one or more amino acid substitutions selected from the group consisting of N297A, K322A, L234A and L235A. In other embodiments, the multi-specific (e.g., bispecific) antibody or antigen binding fragment comprises an IgG4 constant region comprising a S228P mutation.

In another aspect, the present disclosure provides a multi-specific (e.g., bispecific) antibody comprising a first antigen binding moiety that binds a Claudin 18.2 epitope and a second antigen binding moiety that binds to a second epitope, wherein the first antigen binding moiety comprises a first heavy chain immunoglobulin variable domain ($V_H$) and a first light chain immunoglobulin variable domain ($V_L$), wherein the second antigen binding moiety comprises a second $V_H$ and a second $V_L$, and wherein (a) the first $V_L$ sequence is at least 95% identical to the light chain immunoglobulin variable domain sequence of any one of SEQ ID NOs: 37, 39, 41, 43, 45, 50-53, or 58-61; and/or (b) the first $V_H$ sequence is at least 95% identical to the heavy chain immunoglobulin variable domain sequence of any one of SEQ ID NOs: 36, 38, 40, 42, 44, 46-49, or 54-57. Additionally or alternatively, in some embodiments, the second $V_H$ comprises an amino acid sequence selected from any one of SEQ ID NOs: 97, 99, 100, 101, 102, or 157; and/or (b) the second $V_L$ comprises an amino acid sequence selected from any one of SEQ ID NOs: 98, 103, or 158.

In one aspect, the present disclosure provides a multi-specific (e.g., bispecific) antibody comprising a first antigen binding moiety that binds a Claudin 18.2 epitope and a second antigen binding moiety that binds to a second epitope, wherein the multi-specific antibody comprises a heavy chain (HC) amino acid sequence comprising SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, SEQ ID NO: 161, or a variant thereof having one or more conservative amino acid substitutions, and/or a light chain (LC) amino acid sequence comprising SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, SEQ ID NO: 162, or a variant thereof having one or more conservative amino acid substitutions. In some embodiments, the multi-specific (e.g., bispecific) antibody comprises a HC amino acid sequence and a LC amino acid sequence selected from the group consisting of: SEQ ID NO: 62 and SEQ ID NO: 63, SEQ ID NO: 64 and SEQ ID NO: 65, SEQ ID NO: 66 and SEQ ID NO: 67, SEQ ID NO: 68 and SEQ ID NO: 69, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 159 and SEQ ID NO: 160, and SEQ ID NO: 161 and SEQ ID NO: 162, respectively. In another aspect, the present disclosure provides a multi-specific (e.g., bispecific) antibody comprising a first antigen binding moiety that binds a Claudin 18.2 epitope and a second antigen binding moiety that binds to a second epitope, wherein the multi-specific antibody comprises: (a) a LC sequence that is at least 95% identical to the LC sequence present in SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, or SEQ ID NO: 162; and/or (b) a HC sequence that is at least 95% identical to the HC sequence present in SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, or SEQ ID NO: 161. Additionally or alternatively, in some embodiments, the immunoglobulin-related compositions contain an IgG4 constant region comprising a S228P mutation. In certain embodiments, the multi-specific (e.g., bispecific) antibody or antigen binding fragment comprises an IgG1 constant region comprising one or more amino acid substitutions selected from the group consisting of N297A, K322A, L234A and L235A.

In any and all embodiments of the multi-specific (e.g., bispecific) antibody or antigen binding fragment disclosed herein, the multi-specific (e.g., bispecific) antibody or antigen binding fragment binds to a CLDN18.2 polypeptide comprising an extracellular loop 1 (EL1) sequence. The extracellular loop 1 (EL1) sequence may comprise the amino acid sequence of SEQ ID NO: 2, or the CLDN18.2 polypeptide may comprise the amino acid sequence of SEQ ID NO: 4. Additionally or alternatively, in some embodiments, the multi-specific (e.g., bispecific) antibody of the present technology is a monoclonal antibody, a chimeric antibody, or a humanized antibody, and/or lacks α-1,6-fucose modifications.

In one aspect, the present disclosure provides a multi-specific (e.g., bispecific) antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 79); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 80) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin or the heavy chain variable domain of the second immunoglobulin is selected from any one of SEQ ID NOs: 36, 38, 40, 42, 44, 46-49, or 54-57, and/or the light chain variable domain of the first immunoglobulin or the light chain variable domain of the second immunoglobulin is selected from any one of SEQ ID NOS: 37, 39, 41, 43, 45, 50-53, or 58-61.

Additionally or alternatively, in some embodiments, the heavy chain variable domain of the first immunoglobulin is selected from any one of SEQ ID NOs: 36, 38, 40, 42, 44, 46-49, or 54-57, the light chain variable domain of the first immunoglobulin is selected from any one of SEQ ID NOs: 37, 39, 41, 43, 45, 50-53, or 58-61, the heavy chain variable domain of the second immunoglobulin is selected from any one of SEQ ID NOS: 97, 99, 100, 101, 102, or 157, and the light chain variable domain of the second immunoglobulin is selected from any one of SEQ ID NOs: 98, 103, or 158.

In other embodiments, the heavy chain variable domain of the first immunoglobulin is selected from any one of SEQ ID NOs: 97, 99, 100, 101, 102, or 157, the light chain variable domain of the first immunoglobulin is selected from any one of SEQ ID NOs: 98, 103, or 158, the heavy chain variable domain of the second immunoglobulin is selected from any one of SEQ ID NOs: 36, 38, 40, 42, 44, 46-49, or 54-57, and the light chain variable domain of the second immunoglobulin is selected from any one of SEQ ID NOs: 37, 39, 41, 43, 45, 50-53, or 58-61.

Additionally or alternatively, in some embodiments, the multi-specific antibody or antigen binding fragment of the present technology also binds to T cells and/or CD3. In one aspect, the present disclosure provides a T cell that is armed ex vivo with a multi-specific antibody or antigen binding fragment of the present technology that also binds to T cells and/or CD3. In another aspect, the present disclosure provides an ex vivo method of making a therapeutic T cell, comprising arming a T cell ex vivo with a multi-specific antibody or antigen binding fragment of the present technology that is capable of binding to T cells and/or CD3, wherein the T cell is optionally a human T cell, and wherein the binding is noncovalent. In another aspect, the present disclosure provides a method for treating cancer in a subject in need thereof, comprising administering to the subject an effective amount of a T cell that is armed ex vivo with a multi-specific antibody or antigen binding fragment of the present technology that also binds to T cells and/or CD3.

In one aspect, the present disclosure provides a recombinant nucleic acid sequence encoding any of the multi-specific (e.g., bispecific) antibodies or antigen binding fragments described herein. In another aspect, the present disclosure provides a host cell or vector comprising any of the recombinant nucleic acid sequences disclosed herein.

In yet another aspect, the present disclosure provides a pharmaceutical composition comprising any of the multi-specific (e.g., bispecific) antibodies or antigen binding fragments described herein and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. In some embodiments, the pharmaceutical composition further comprises an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

Additionally or alternatively, in some embodiments, the multi-specific (e.g., bispecific) antibody or antigen binding fragment of the present technology binds to T cells, B-cells, myeloid cells, plasma cells, or mast-cells. Additionally or alternatively, in some embodiments, the second antigen binding moiety of the multi-specific (e.g., bispecific) antibody or antigen binding fragment binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys (HSG)-D-Tyr-Lys (HSG)-$NH_2$, Ac-Lys (HSG) D-Tyr-Lys (HSG)-Lys (Tscg-Cys)-$NH_2$, DOTA-D-Asp-D-Lys (HSG)-D-Asp-D-Lys (HSG)-$NH_2$; DOTA-D-Glu-D-Lys (HSG)-D-Glu-D-Lys (HSG)-$NH_2$, DOTA-D-Tyr-D-Lys (HSG)-D-Glu-D-Lys (HSG)-$NH_2$, DOTA-D-Ala-D-Lys (HSG)-D-Glu-D-Lys (HSG)-$NH_2$, DOTA-D-Phe-D-Lys (HSG)-D-Tyr-D-Lys (HSG)-$NH_2$, Ac-D-Phe-D-Lys (DOTA)-D-Tyr-D-Lys (DOTA)-$NH_2$, Ac-D-Phe-D-Lys (DTPA)-D-Tyr-D-Lys (DTPA)-$NH_2$, Ac-D-Phe-D-Lys (Bz-DTPA)-D-Tyr-D-Lys (Bz-DTPA)-$NH_2$, Ac-D-Lys (HSG)-D-Tyr-D-Lys (HSG)-D-Lys (Tscg-Cys)-$NH_2$, DOTA-D-Phe-D-Lys (HSG)-D-Tyr-D-Lys (HSG)-D-Lys (Tscg-Cys)-$NH_2$, (Tscg-Cys)-D-Phe-D-Lys (HSG)-D-Tyr-D-Lys (HSG)-D-Lys (DOTA)-$NH_2$, Tscg-D-Cys-D-Glu-D-Lys (HSG)-D-Glu-D-Lys (HSG)-$NH_2$, (Tscg-Cys)-D-Glu-D-Lys (HSG)-D-Glu-D-Lys (HSG)-$NH_2$, Ac-D-Cys-D-Lys (DOTA)-D-Tyr-D-Ala-D-Lys (DOTA)-D-Cys-$NH_2$, Ac-D-Cys-D-Lys (DTPA)-D-Tyr-D-Lys (DTPA)-$NH_2$, Ac-D-Lys (DTPA)-D-Tyr-D-Lys (DTPA)-D-Lys (Tscg-Cys)-$NH_2$, and Ac-D-Lys (DOTA)-D-Tyr-D-Lys (DOTA)-D-Lys (Tscg-Cys)-$NH_2$.

In one aspect, the present disclosure provides a method for treating cancer in a subject in need thereof, comprising administering to the subject an effective amount of any of the multi-specific (e.g., bispecific) antibodies or antigen binding fragments described herein, or any of the pharmaceutical compositions disclosed herein, wherein the multi-specific (e.g., bispecific) antibody or antigen binding fragment specifically binds to CLDN18.2. In some embodiments, the cancer is a solid tumor. Examples of cancer include, but are not limited to, gastric cancer, esophageal cancer, pancreatic cancer, lung cancer, non small cell lung cancer (NSCLC), ovarian cancer, colon cancer, hepatic cancer, head-neck cancer, and gallbladder cancer. In some embodiments of the method, the multi-specific (e.g., bispecific) antibody or antigen binding fragment is administered to the subject separately, sequentially or simultaneously with an additional therapeutic agent. Examples of additional therapeutic agents include one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, T cells, and immuno-modulating/stimulating antibodies (e.g., an anti-PD-1 antibody, an anti-PD-L1 antibody, an anti-PD-L2 antibody, an anti-CTLA-4 antibody, an anti-TIM3 antibody, an anti-4-1BB antibody, an anti-CD73 antibody, an anti-GITR antibody, or an anti-LAG-3 antibody).

In another aspect, the present disclosure provides a method for detecting cancer in a subject in vivo comprising (a) administering to the subject an effective amount of a multi-specific (e.g., bispecific) antibody or antigen binding fragment of the present technology, wherein the multi-specific (e.g., bispecific) antibody or antigen binding fragment is configured to localize to a cancer cell expressing CLDN18.2 and is labeled with a radioisotope; and (b) detecting the presence of a tumor in the subject by detecting radioactive levels emitted by the multi-specific (e.g., bispecific) antibody or antigen binding fragment that are higher than a reference value. In certain embodiments, the cancer is a solid tumor. In some embodiments, the subject is diagnosed with or is suspected of having cancer (e.g., gastric cancer, esophageal cancer, pancreatic cancer, lung cancer, non small cell lung cancer (NSCLC), ovarian cancer, colon cancer, hepatic cancer, head-neck cancer, and gallbladder cancer). Radioactive levels emitted by the multi-specific (e.g., bispecific) antibody or antigen binding fragment may be detected using positron emission tomography or single photon emission computed tomography. Additionally or alternatively, in some embodiments, the method further comprises administering to the subject an effective amount of an immunoconjugate comprising a multi-specific (e.g., bispecific) antibody or antigen binding fragment of the present technology conjugated to a radionuclide.

In any and all embodiments of the methods disclosed herein, the subject is human.

In yet another aspect, the present disclosure provides a method for detecting CLDN18.2 protein expression levels in a biological sample comprising contacting the biological sample with any of the multi-specific (e.g., bispecific) antibodies or antigen binding fragments disclosed herein, and detecting binding to CLDN18.2 protein in the biological sample.

Also disclosed herein are kits for the detection and/or treatment of CLDN18.2-associated cancers comprising at least one immunoglobulin-related composition of the present technology (e.g., any multi-specific (e.g., bispecific) antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label. Additionally or alternatively, in some embodiments, the kit further comprises a secondary antibody that specifically binds to an anti-CLDN18.2 immunoglobulin-related composition described herein. In some embodiments, the secondary antibody is coupled to at least one detectable label selected from the group consisting of a radioactive label, a fluorescent label, or a chromogenic label.

In one aspect, the present disclosure provides an anti-CD3 antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence of any one of SEQ ID NOs: 99-102, or SEQ ID NO: 157; and/or (b) the $V_L$ comprises an amino acid sequence of SEQ ID NO: 103 or SEQ ID NO: 158. In some embodiments, the anti-CD3 antibody or antigen binding fragment comprises heavy chain immunoglobulin variable domain ($V_H$) and light chain immunoglobulin variable domain ($V_L$) amino acid sequences selected from the group consisting of: SEQ ID NO: 101 and SEQ ID NO: 103; and SEQ ID NO: 157 and SEQ ID NO: 158, respectively. Additionally or alternatively, in some embodiments, the anti-CD3 antibody or antigen binding fragment is a monoclonal antibody, a chimeric antibody, a humanized antibody, a bispecific antibody, or multi-specific antibody. The antigen binding fragment may be selected from the group consisting of Fab, F(ab')$_2$, Fab', sc$F_v$, and $F_v$.

Additionally or alternatively, in certain embodiments, the anti-CD3 antibody or antigen binding fragment further comprises a Fc domain of an isotype selected from the group consisting of IgG1, IgG2, IgG3, IgG4, IgA1, IgA2, IgM, IgD, and IgE. In some embodiments, the anti-CD3 antibody further comprises an IgG1 constant region comprising one or more amino acid substitutions selected from the group consisting of N297A, L234A, L235A, and K322A. In other embodiments, the anti-CD3 antibody comprises an IgG4 constant region comprising a S228P mutation. Additionally or alternatively, in some embodiments, the anti-CD3 antibody lacks α-1,6-fucose modifications.

In one aspect, the present disclosure provides a multi-specific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence (GGGGS)$_3$ (SEQ ID NO: 79); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence (GGGGS) 6 (SEQ ID NO: 80) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin or the heavy chain variable domain of the second immunoglobulin comprises any one of SEQ ID NOs: 99-102, or SEQ ID NO: 157, and/or the light chain variable domain of the first immunoglobulin or the light chain variable domain of the second immunoglobulin comprises SEQ ID NO: 103 or SEQ ID NO: 158.

Additionally or alternatively, in some embodiments, the anti-CD3 multi-specific antibody or antigen binding fragment binds to T cells, B-cells, myeloid cells, plasma cells, or mast-cells. Additionally or alternatively, in certain embodiments, the anti-CD3 multi-specific antibody or antigen binding fragment binds to CD3, GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, LMP2, p53, lung resistance protein (LRP), Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, GPC3, EpCAM, CD4, CD8, CD21, CD23, CD46, CD80, HLA-DR, CD74, CD22, CD14, CD15, CD16, CD123, TCR gamma/delta, NKp46, KIR, CD56, DLL3, PD-1, PD-L1, CD28, CD137, CD99, GloboH, CD24, STEAP1, B7H3, Polysialic Acid, OX40, OX40-ligand, peptide MHC complexes (with peptides derived from TP53, KRAS, MYC, EBNA1-6, PRAME, MART, tyronsinase, MAGEA1-A6, pmel17, LMP2, or WT1), or a small molecule DOTA hapten.

In another aspect, the present disclosure provides a composition comprising any and all embodiments of the anti-CD3 antibody or antigen binding fragment disclosed herein and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In yet another aspect, the present disclosure provides a method for treating cancer in a subject in need thereof, comprising administering to the subject an effective amount of any and all embodiments of the anti-CD3 antibody or antigen binding fragment disclosed herein. In another aspect, the present disclosure provides a method for treating cancer in a subject in need thereof, comprising administering to the subject an effective amount of a composition comprising any and all embodiments of the anti-CD3 antibody or antigen binding fragment disclosed herein and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In one aspect, the present disclosure provides a T cell that is armed ex vivo with any and all embodiments of the anti-CD3 antibody or antigen binding fragment disclosed herein. In another aspect, the present disclosure provides an ex vivo method of making a therapeutic T cell, comprising arming a T cell ex vivo with any and all embodiments of the anti-CD3 antibody or antigen binding fragment disclosed herein, wherein the T cell is optionally a human T cell, and wherein the binding is noncovalent. In another aspect, the present disclosure provides a method for treating cancer in a subject in need thereof, comprising administering to the subject an effective amount of a T cell that is armed ex vivo with any and all embodiments of the anti-CD3 antibody or antigen binding fragment disclosed herein.

BRIEF DESCRIPTION OF THE DRAWINGS

FIG. 2 shows an amino acid sequence alignment of hCLDN18.1-EL1 (SEQ ID NO: 1), hCLDN18.2-EL1 (SEQ ID NO: 2) and mCLDN18.2-EL1 (SEQ ID NO: 2), and an amino acid sequence alignment of hCLDN18.1-EL2 (SEQ ID NO: 3) and hCLDN18.2-EL2 (SEQ ID NO: 3). The amino acid sequences of hCLDN18.2-EL1 and mCLDN18.2-EL1 are identical. The amino acid sequences of hCLDN18.1-EL2 and hCLDN18.2-EL2 are identical.

FIG. 10 shows the amino acid sequence of human CLDN18.2 protein (SEQ ID NO: 4).

FIG. 11 shows the amino acid sequence of human CLDN18.1 protein (SEQ ID NO: 5).

FIG. 12 shows the $V_H$ CDR1, $V_H$ CDR2, $V_H$ CDR3, $V_L$ CDR1, $V_L$ CDR2, and $V_L$ CDR3 sequences of murine clones 32G4 (SEQ ID NOs: 6-11, respectively), 47D10 (SEQ ID NOs: 12-17, respectively), 29G4 (SEQ ID NOs: 18-23, respectively), 31A6 (SEQ ID NOs: 24-29, respectively), and 15B10 (SEQ ID NOs: 30-35, respectively). SEQ ID NO:

155 corresponds to the 32G4-huVL4 CDR2 sequence and SEQ ID NO: 156 corresponds to the 47D10-huVL4 CDR2 sequence.

FIG. 13 shows the amino acid sequences of the variable heavy immunoglobulin domain ($V_H$) and the variable light immunoglobulin domain ($V_L$) of murine clones 32G4 (SEQ ID NO: 36 and SEQ ID NO: 37, respectively), 47D10 (SEQ ID NO: 38 and SEQ ID NO: 39, respectively), 29G4 (SEQ ID NO: 40 and SEQ ID NO: 41, respectively), 31A6 (SEQ ID NO: 42 and SEQ ID NO: 43, respectively) and 15B10 (SEQ ID NO: 44 and SEQ ID NO: 45, respectively). The $V_H$ CDR 1-3 and $V_L$ CDR 1-3 amino acid sequences are underlined.

FIG. 14 shows the amino acid sequences of four humanized $V_H$ variants (SEQ ID NOs: 46-49) and four humanized $V_L$ variants (SEQ ID NOs: 50-53) for clone 32G4. The $V_H$CDR 1-3 and $V_L$ CDR 1-3 amino acid sequences are underlined.

FIG. 15 shows the amino acid sequences of four humanized $V_H$ variants (SEQ ID NOs: 54-57) and four humanized $V_L$ variants (SEQ ID NOs: 58-61) for clone 47D10. The $V_H$CDR 1-3 and $V_L$ CDR 1-3 amino acid sequences are underlined.

FIG. 16 shows the heavy chain (HC) and light chain (LC) amino acid sequences of 32G4-huIgG1-V8 (SEQ ID NO: 62 and SEQ ID NO: 63) and 32G4-huIgG1-V9 (SEQ ID NO: 64 and SEQ ID NO: 65). The $V_H$ CDR 1-3 and $V_L$ CDR 1-3 amino acid sequences are underlined, and the $V_H$ and $V_L$ amino acid sequences are italicized.

FIG. 17 shows the heavy chain (HC) and light chain (LC) amino acid sequences of 47D10-huIgG1-V6 (SEQ ID NO: 66 and SEQ ID NO: 67) and 47D10-huIgG1-V7 (SEQ ID NO: 68 and SEQ ID NO: 69). The $V_H$ CDR 1-3 and $V_L$ CDR 1-3 amino acid sequences are underlined, and the $V_H$ and $V_L$ amino acid sequences are italicized.

Figure 18:
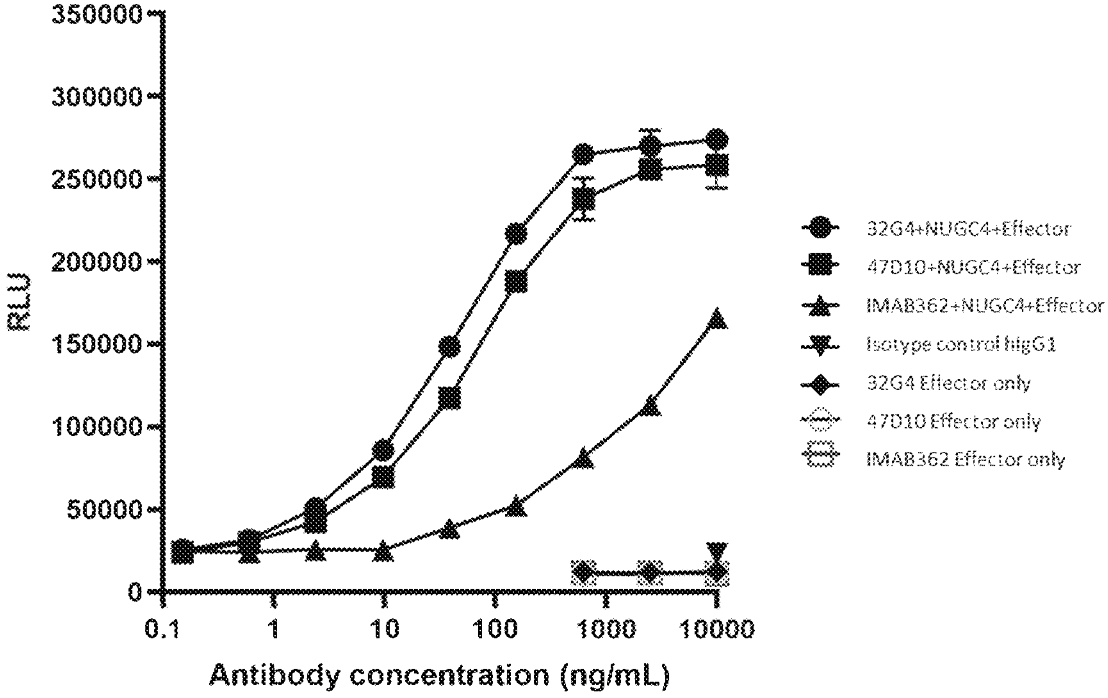

FIG. 18 shows the exemplary antibody-dependent cellular cytotoxicity (ADCC) assay data of 32G4 and 47D10 clones, in comparison to the IMAB362 benchmark antibody and the negative isotype control.

FIG. 19 shows the cross species binding of exemplary humanized 32G4 and 47D10 antibody variants to cynomolgus monkey and mouse claudin 18.2 target protein on cell surface relative to the IMAB362 benchmark antibody and the negative isotype control.

FIG. 20 shows exemplary heavy chain (HC) and light chain (LC) amino acid sequences of 32G4-huIgG1-V8×OKT3 (anti-CLDN18.2×CD3) bispecific antibody (BsAb) (SEQ ID NO: 81 and SEQ ID NO: 82) and 32G4-huIgG1-V9×OKT3 (anti-CLDN18.2×CD3) BsAb (SEQ ID NO: 83 and SEQ ID NO: 84). The $V_H$ CDR 1-3 and $V_L$ CDR 1-3 amino acid sequences of the anti-CLDN18.2 immunoglobulin are underlined, all linkers are boldface, and all $V_H$ and $V_L$ amino acid sequences of the BsAb are italicized.

FIG. 21 shows exemplary heavy chain (HC) and light chain (LC) amino acid sequences of 47D10-huIgG1-V6×OKT3 (anti-CLDN18.2×CD3) bispecific antibody (BsAb) (SEQ ID NO: 85 and SEQ ID NO: 86) and 47D10-huIgG1-V7×OKT3 BsAb (anti-CLDN18.2×CD3) (SEQ ID NO: 87 and SEQ ID NO: 88). The $V_H$CDR 1-3 and $V_L$ CDR 1-3 amino acid sequences of the anti-CLDN18.2 immunoglobulin are underlined, all linkers are boldface, and all $V_H$ and $V_L$ amino acid sequences of the BsAb are italicized.

FIG. 22 shows exemplary heavy chain (HC) and light chain (LC) amino acid sequences of 32G4-huIgG1-V8×huSP34 (anti-CLDN18.2×CD3) bispecific antibody (BsAb) (SEQ ID NO: 89 and SEQ ID NO: 90) and 32G4-huIgG1-V9×huSP34 BsAb (anti-CLDN18.2×CD3) (SEQ ID NO: 91 and SEQ ID NO: 92). The $V_H$CDR 1-3 and $V_L$ CDR 1-3 amino acid sequences of the anti-CLDN18.2 immunoglobulin are underlined, all linkers are boldface, and all $V_H$ and $V_L$ amino acid sequences of the BsAb are italicized.

FIG. 23 shows exemplary heavy chain (HC) and light chain (LC) amino acid sequences of 47D10-huIgG1-V6×huSP34 (anti-CLDN18.2×CD3) bispecific antibody (BsAb) (SEQ ID NO: 93 and SEQ ID NO: 94) and 47D10-huIgG1-V7×huSP34 BsAb (anti-CLDN18.2×CD3) (SEQ ID NO: 95 and SEQ ID NO: 96). The $V_H$CDR 1-3 and $V_L$ CDR 1-3 amino acid sequences of the anti-CLDN18.2 immunoglobulin are underlined, all linkers are boldface, and all $V_H$ and $V_L$ amino acid sequences of the BsAb are italicized.

Figure 24:
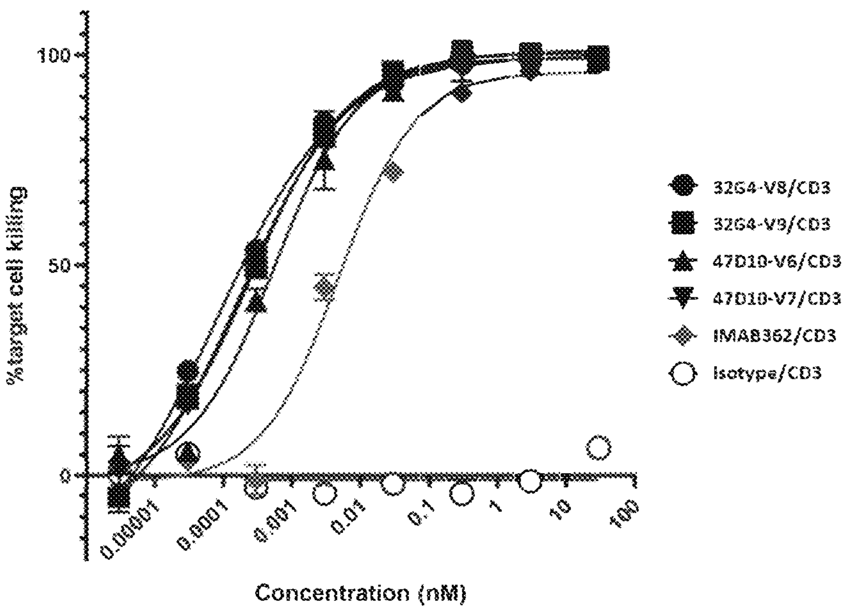

FIG. 24 shows exemplary gastric cancer cell killing (TDCC) assay data of 32G4-anti-CD3 and 47D10-anti-CD3 bispecific antibody variants, in comparison with the IMAB362-anti-CD3 benchmark antibody and the negative isotype control.

FIG. 25 shows $V_H$ and $V_L$ amino acid sequences of anti-CD3 OKT3 antibody (SEQ ID NO: 97 and SEQ ID NO:98), $V_H$ amino acid sequences of humanized SP34 $V_H$ 1-5 (SEQ ID NOs: 99-102, and 157), and $V_L$ amino acid sequences of humanized SP34 $V_L$ (SEQ ID NOs: 103 and 158).

FIG. 26 shows exemplary heavy chain (HC) and light chain (LC) amino acid sequences of 32G4-V8×huSP34-v5 (anti-CLDN18.2×CD3) bispecific antibody (BsAb) (SEQ ID NO: 159 and SEQ ID NO: 160) and 47D10-V7×huSP34-v5 BsAb (anti-CLDN18.2×CD3) (SEQ ID NO: 161 and SEQ ID NO: 162). The $V_H$CDR 1-3 and $V_L$ CDR 1-3 amino acid sequences of the anti-CLDN18.2 immunoglobulin are underlined, all linkers are boldface, and all $V_H$ and $V_L$ amino acid sequences of the BsAb are italicized.

Figure 27:
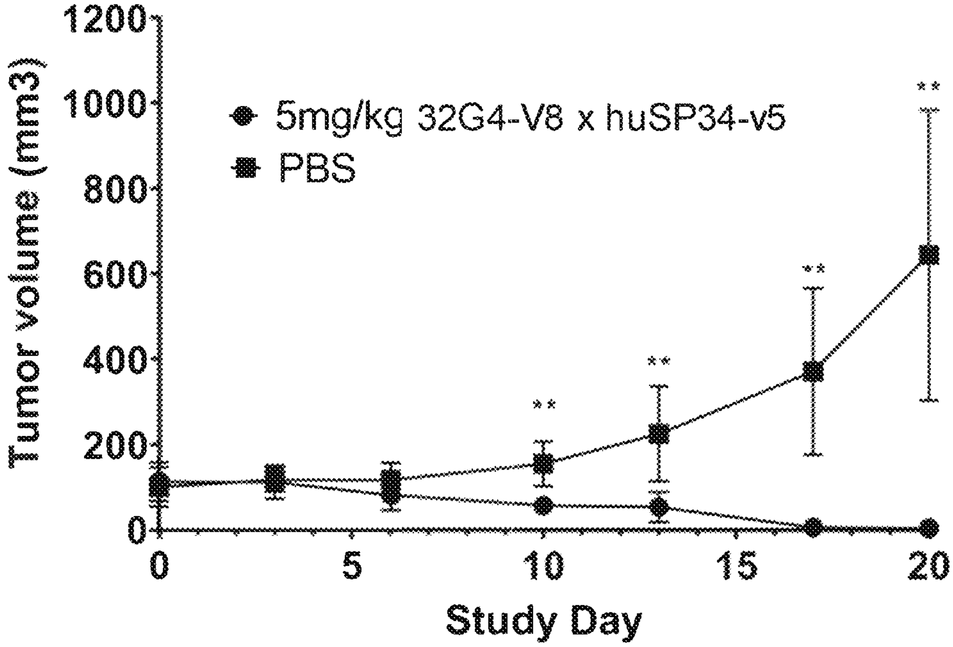

FIG. 27 shows exemplary in vivo efficacy of 32G4-V8×huSP34-v5 in a mouse xenograft gastric cancer model.

FIG. 28 shows exemplary stability of 32G4-V8×huSP34-v5 under accelerated stress test conditions as assessed by SEC-HPLC.

Figure 29:
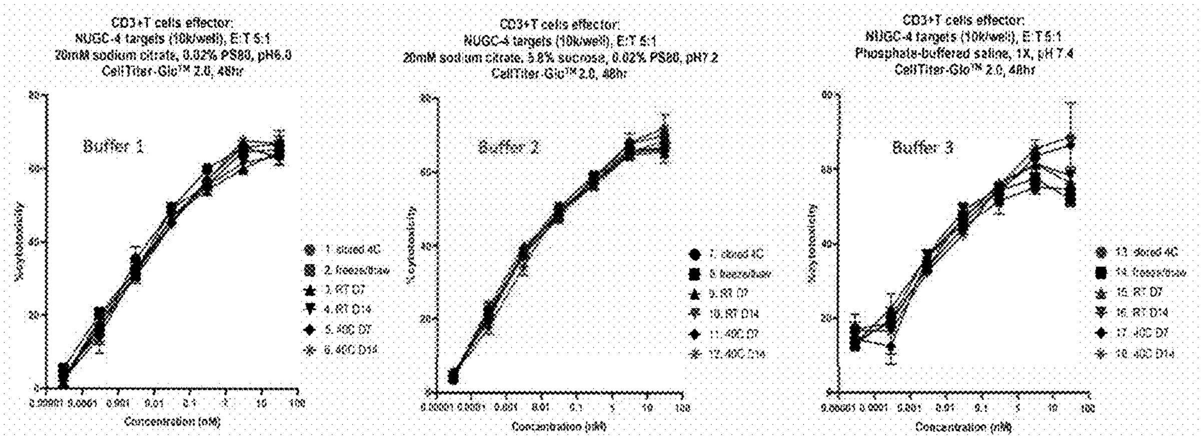

FIG. 29 shows exemplary gastric cancer cell killing (TDCC) assay data of 32G4-V8×huSP34-v5 under accelerated stress test conditions.

DETAILED DESCRIPTION

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to Claudin 18.2 polypeptides. The immunoglobulin-related compositions of the present technology are useful in methods for detecting or treating Claudin 18.2-associated cancers in a subject in need thereof. Accordingly, the various aspects of the present methods relate to the preparation, characterization, and manipulation of anti-Claudin 18.2 antibodies. The immunoglobulin-related compositions of the present technology are useful alone or in combination with additional therapeutic agents for treating cancer. In some embodiments, the immunoglobulin-related composition is a monoclonal antibody, a humanized antibody, a chimeric antibody, a bispecific antibody, or a multi-specific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) PCR 1*: A Practical Approach* (IRL Press at Oxford University Press); MacPherson et al. (1995) PCR 2*: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) Oligonucleotide Synthesis; U.S. Pat. No. 4,683,195; Hames and Higgins eds. (1984) *Nucleic Acid Hybridization; Anderson* (1999) *Nucleic Acid Hybridization*; Hames and Higgins eds. (1984) *Transcription and Translation; Immobilized Cells and Enzymes* (*IRL Press* (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), QUIL-A™ (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, *J., Immunology,* 3rd Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$CDR3 is located in the variable domain of the heavy chain of the antibody in which it is found, whereas a $V_L$ CDR1 is the CDR1 from the variable domain of the light chain of the antibody in which it is found. An antibody that binds Claudin 18.2 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multi-specific antibodies, bispecific antibodies, etc.) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, CL and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a $F_v$ fragment consisting of the $V_L$ and $V_H$ domains of a single arm of an antibody, (v) a dAb fragment (Ward et al., Nature 341:544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', F(ab')$_2$, and $F_v$ fragments; diabodies; linear antibodies; single-chain antibody molecules; and multi-specific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the term "antibody-dependent cell-mediated cytotoxicity" or "ADCC", refers to a mechanism of cell-mediated immune defense whereby an effector cell of the immune system actively lyses a target cell, such as a tumor cell, whose membrane-surface antigens have been bound by antibodies, such as anti-CLDN18.2 antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a CLDN18.2 polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto. Any of the above-noted antibody fragments are obtained using conventional techniques known to those of skill in the art, and the fragments are screened for binding specificity and neutralization activity in the same manner as are intact antibodies.

As used herein, "binding affinity" means the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a tissue sample obtained by needle biopsy.

As used herein, the term "CDR grafting" means replacing at least one CDR of an "acceptor" antibody by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240:1041-1043, 1988; Liu et al., *Proc. Natl. Acad. Sci. USA* 84:3439-3443, 1987; Liu et al., *J. Immunol* 139:3521-3526, 1987; Sun et al., *Proc. Natl. Acad. Sci. USA* 84:214-218, 1987; Nishimura et al., *Cancer Res* 47:999-1005, 1987; Wood et al., *Nature* 314:446-449, 1885; and Shaw et al., *J. Natl. Cancer Inst.* 80:1553-1559, 1988.

As used herein, the term "complement-dependent cytotoxicity" or "CDC" generally refers to an effector function of IgG and IgM antibodies, which trigger classical complement pathway when bound to a surface antigen, inducing formation of a membrane attack complex and target cell lysis.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and Hollinger et al., *Proc Natl Acad Sci USA,* 90:6444-6448 (1993).

As used herein, the term "EC50", known as half maximal effective concentration, refers to the concentration of an antibody which induces a response halfway between the baseline and maximum after a specified exposure time.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the CLDN18.2 protein is a region of the protein to which the anti-CLDN18.2 antibodies of the present technology specifically bind. In some embodiments, the epitope is a conformational epitope or a non-conformational epitope. To screen for anti-CLDN18.2 antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-CLDN18.2 antibody binds the same site or epitope as an anti-CLDN18.2 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of CLDN18.2 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, "homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GENBANK™+EMBL™+DDBJ+PDB+GENBANK™ CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588 (2): 288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, "immunogen" refers to any antigen that is capable of inducing humoral and/or cell-mediated immune response rather than immunological tolerance.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

As used herein, the terms "individual", "patient", or "subject" can be an individual organism, a vertebrate, a mammal, or a human. In some embodiments, the individual, patient or subject is a human.

As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence

```
                                    (SEQ ID NO: 79)
GGGGSGGGGSGGGGS
or
                                    (SEQ ID NO: 80)
GGGGSGGGGSGGGGSGGGGSGGGGSGGGGS.
```

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "nucleic acid" or "polynucleotide" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "pharmaceutically acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20th edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the terms "polypeptide," "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ ($scF_v$)). Bird et al. (1988) *Science* 242:423-426 and Huston et al. (1988) *Proc Natl Acad Sci* 85:5879-5883. Such single-chain antibodies can be prepared by recombinant techniques or enzymatic or chemical cleavage of intact antibodies.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$M, $10^{-5}$ M, $10^{-6}$M, $10^{-7}$M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a CLDN18.2 polypeptide), or an epitope on a particular polypeptide, without substantially binding to any other polypeptide, or polypeptide epitope.

As used herein, "sequence liabilities" refer to any feature in nucleic acid or amino acid sequences that can affect the heterogeneity of the immunoglobulin-related compositions of the present disclosure. Such sequence liabilities include but not limited to, any sequence motifs that are prone to deamidation, isomerization, cleavage, oxidation, and glycosylation.

As used herein, the terms "subject", "patient", or "individual" can be an individual organism, a vertebrate, a mammal, or a human. In some embodiments, the subject, patient or individual is a human.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-CLDN18.2 antibodies described herein are contemplated. Such modifications can be performed to improve the binding affinity and/or other biological properties of the antibody, for examples, to render the encoded amino acid glycosylated, or to destroy the antibody's ability to bind to C1q, Fc receptor, or to activate the complement system. Amino acid sequence variants of an anti-CLDN18.2 antibody are prepared by introducing appropriate nucleotide changes into the antibody nucleic acid, by peptide synthesis, or by chemical modifications. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated.

Conservative amino acid substitutions are amino acid substitutions that change a given amino acid to a different amino acid with similar biochemical properties (e.g., charge, hydrophobicity and size). "Conservative substitutions" are shown in the Table below.

TABLE 1

Amino Acid Substitutions

| Original Residue | Exemplary Substitutions | Conservative Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

Claudins

In human, 27 family members of claudin have been described, including claudin 18. All claudins have four transmembrane domains and two extracellular loops, with the N-terminus and the C-terminus in the cytoplasm (Markov, A. G., et al., *IUBMB Life* 67:29-35 (2015); Furuse, M., et al., *J Cell Biol* 141:1539-1550 (1998); Turksen, K. And Troy, T. C., *Biochim Biophys Acta* 1816:73-79 (2011)).

Figure 1:
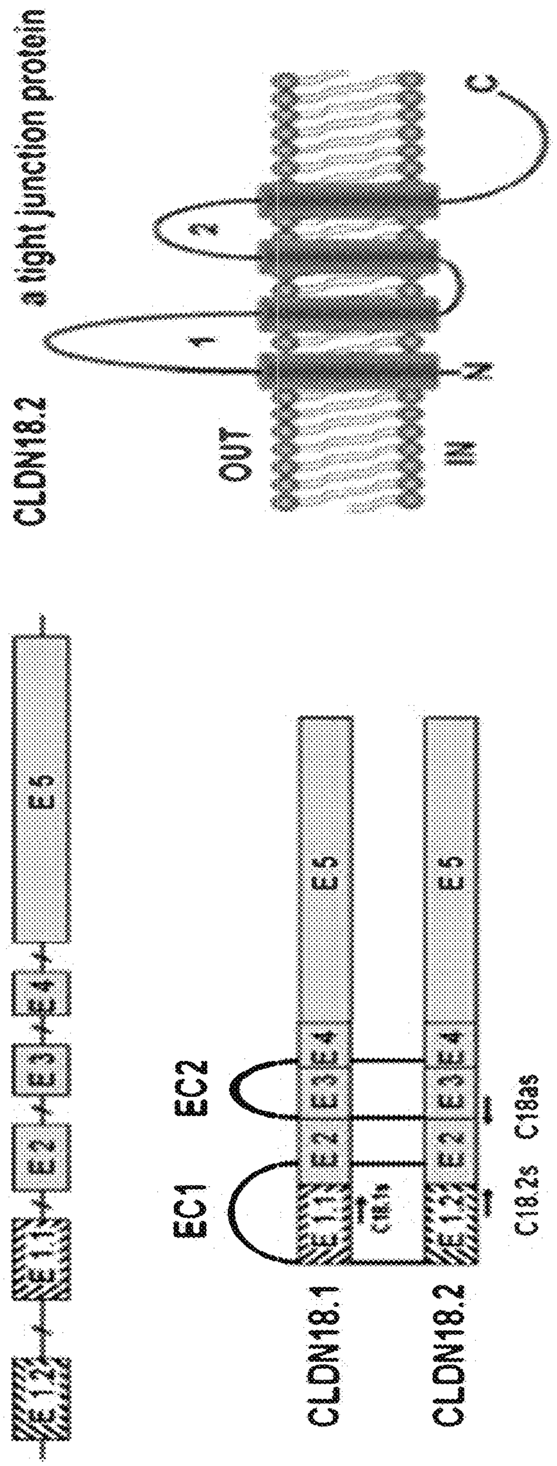
FIG. 1 shows splicing variants and the schematic protein structure of Claudin 18.2 (adapted from Markov, A. G. et al., *IUBMB Life* 67:29-35 (2015)).

The claudin family member 18 gene is composed of 5 exons. There are two splicing variants, Claudin 18.1 (CLDN18.1) and Claudin 18.2 (CLDN18.2). The two variants are the products of alternative splicing that utilize alternative DNA sequences in exon 1, which encode the N-terminal portion of the protein including the first extracellular loop (EL1) (FIG. 1) (Mineta, K., et al., *FEBS Lett* 585:606-612 (2011); Suzuki, H., et al., *Science* 344:304-307 (2014)). CLDN18.1 and CLDN18.2 have different EL1 sequences, but share an identical EL2 sequence (FIG. 2). The homology of CLDN18.2 is extremely high in species such as human, cynomolgus, and mice, as they all possess an identical EL1 amino acid sequence.

Figure 3:
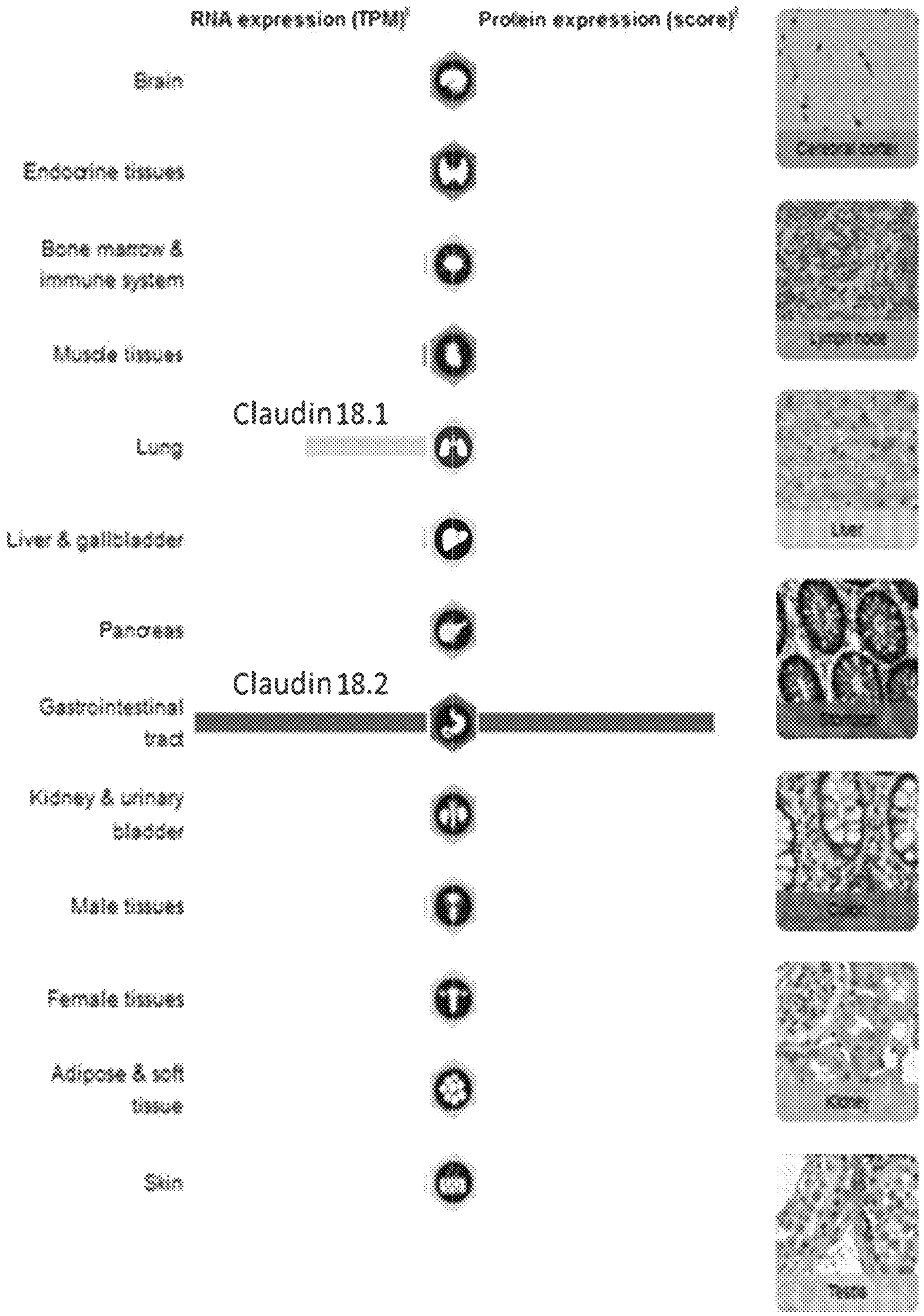
FIG. 3 shows RNA and protein expression of CLDN18 in normal human tissues (adapted from Human Protein Atlas data: www.proteinatlas.org/ENSG00000066405-CLDN18/tissue).
Figure 4:
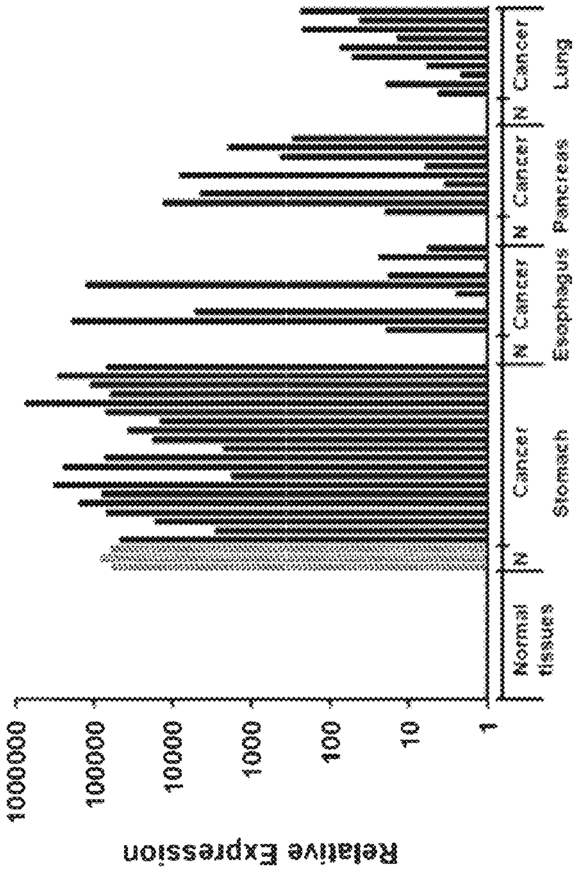
FIG. 4 shows expression of CLDN18 in human cancer tissues (adapted from Sahin U., et al., *Clin Cancer Res* 14:7624-7634 (2008)).

The expression of Claudin 18 in normal human tissues is highly restricted, with CLDN18.1 found predominately in lung and CLDN18.2 in stomach (FIG. 3) (Sahin U., et al., *Clin Cancer Res* 14:7624-7634 (2008)). Cancerous expression of CLDN18.2 has been reported in gastric, pancreatic, and other cancers (FIG. 4) (Sahin U., et al., *Clin Cancer Res* 14:7624-7634 (2008); Karanjawala, Z. E., et al., *Am J Surg Pathol* 32:188-196 (2008)). One study reported that 70% of gastric cancers, 50% of pancreatic cancers, 30% of esophageal cancers, and 25% of NSCLC express CLDN18.2 (Sahin U., et al., *Clin Cancer Res* 14:7624-7634 (2008)). CLDN18.2 has been regarded as a specific gastric tumor associated antigen (TAA).

The malignancy associated expression of CLDN18.2 and its tissue restricted expression makes it an ideal target for antibody-based therapy (Sahin U., et al., *Clin Cancer Res* 14:7624-7634 (2008)). While there is no open access to the normal tight junction forming CLDN18.2 in the gastric mucosa, CLDN18.2 epitopes become exposed on the cell surface upon malignant transformation, thereby making them accessible to therapeutic antibodies.

Immunoglobulin-Related Compositions of the Present Technology

The present technology describes methods and compositions for the generation and use of anti-CLDN18.2 immunoglobulin-related compositions (e.g., anti-CLDN18.2 antibodies or antigen binding fragments thereof). The antibodies and antigen binding fragments of the present technology selectively bind to CLDN18.2 polypeptides (FIG. 10) instead of CLDN18.1 polypeptides (FIG. 11). The anti-CLDN18.2 immunoglobulin-related compositions of the present disclosure may be useful in the diagnosis, or treatment of CLDN18.2-associated cancers. Anti-CLDN18.2 immunoglobulin-related compositions within the scope of the present technology include, e.g., but are not limited to, monoclonal, chimeric, humanized, bispecific antibodies and diabodies that specifically bind the target polypeptide, a homolog, derivative or a fragment thereof. The present disclosure also provides antigen binding fragments of any of the anti-CLDN18.2 antibodies disclosed herein, wherein the antigen binding fragment is selected from the group consisting of Fab, F(ab)'2, Fab', $scF_v$, and $F_v$. The amino acid sequences of the anti-CLDN18.2 immunoglobulin-related compositions of the present technology are described in FIGS. 12-17 and 20-23.

In one aspect, the present disclosure provides an antibody or an antigen binding fragment thereof, comprising a heavy chain immunoglobulin variable domain ($V_H$) and a light chain immunoglobulin variable domain ($V_L$), wherein (a) the $V_H$ comprises a $V_H$-CDR1 sequence selected from the group consisting of SEQ ID NOs: 6, 12, 18, 24 and 30, a $V_H$-CDR2 sequence selected from the group consisting of SEQ ID NOs: 7, 13, 19, 25, and 31, and a $V_H$-CDR3 sequence selected from the group consisting of SEQ ID NOs: 8, 14, 20, 26, and 32, and/or (b) the $V_L$ comprises a $V_L$-CDR1 sequence selected from the group consisting of SEQ ID NOs: 9, 15, 21, 27, and 33, a $V_L$-CDR2 sequence selected from the group consisting of SEQ ID NOs: 10, 16, 22, 28, 34, 155 and 156 and a $V_L$-CDR3 sequence selected from the group consisting of SEQ ID NOs: 11, 17, 23, 29, and 35.

In one aspect, the present disclosure provides an antibody or an antigen binding fragment thereof, comprising a heavy chain immunoglobulin variable domain ($V_H$) and a light chain immunoglobulin variable domain ($V_L$), wherein (a) the $V_H$ comprises a $V_H$-CDR1 sequence of SEQ ID NO: 6, a $V_H$-CDR2 sequence of SEQ ID NO: 7, and a $V_H$-CDR3 sequence of SEQ ID NO: 8, and/or the $V_L$ comprises a $V_L$-CDR1 sequence of SEQ ID NO: 9, a $V_L$-CDR2 sequence of SEQ ID NO: 10 or SEQ ID NO: 155, and a $V_L$-CDR3 sequence of SEQ ID NO: 11; (b) the $V_H$ comprises a $V_H$-CDR1 sequence of SEQ ID NO: 12, a $V_H$-CDR2 sequence of SEQ ID NO: 13, and a $V_H$-CDR3 sequence of SEQ ID NO: 14, and/or the $V_L$ comprises a $V_L$-CDR1 sequence of SEQ ID NO: 15, a $V_L$-CDR2 sequence of SEQ ID NO: 16 or SEQ ID NO: 156, and a $V_L$-CDR3 sequence of SEQ ID NO: 17; (c) the $V_H$ comprises a $V_H$-CDR1 sequence of SEQ ID NO: 18, a $V_H$-CDR2 sequence of SEQ ID NO: 19, and a $V_H$-CDR3 sequence of SEQ ID NO: 20, and/or the $V_L$ comprises a $V_L$-CDR1 sequence of SEQ ID NO: 21, a $V_L$-CDR2 sequence of SEQ ID NO: 22, and a $V_L$-CDR3 sequence of SEQ ID NO: 23; (d) the $V_H$ comprises a $V_H$-CDR1 sequence of SEQ ID NO: 24, a $V_H$-CDR2 sequence of SEQ ID NO: 25, and a $V_H$-CDR3 sequence of SEQ ID NO: 26, and/or the $V_L$ comprises a $V_L$-CDR1 sequence of SEQ ID NO: 27, a $V_L$-CDR2 sequence of SEQ ID NO: 28, and a $V_L$-CDR3 sequence of SEQ ID NO: 29; or (e) the $V_H$ comprises a $V_H$-CDR1 sequence of SEQ ID NO: 30, a $V_H$-CDR2 sequence of SEQ ID NO: 31, and a $V_H$-CDR3 sequence of SEQ ID NO: 32, and/or the $V_L$ comprises a $V_L$-CDR1 sequence of SEQ ID NO: 33, a $V_L$-CDR2 sequence of SEQ ID NO: 34, and a $V_L$-CDR3 sequence of SEQ ID NO: 35.

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from any one of SEQ ID NOs: 36, 38, 40, 42, 44, 46-49, or 54-57; and/or (b) the $V_L$ comprises an amino acid sequence selected from any one of SEQ ID NOS: 37, 39, 41, 43, 45, 50-53, or 58-61.

In any of the above embodiments, the antibody further comprises a Fc domain of any isotype, e.g., but are not limited to, IgG (including IgG1, IgG2, IgG3, and IgG4), IgA (including IgA1 and IgA2), IgD, IgE, or IgM, and IgY. Non-limiting examples of constant region sequences include:

Human IgD constant region, Uniprot: P01880

(SEQ ID NO: 70)

APTKAPDVFPIISGCRHPKDNSPVVLACLITGYHPTSVTVTWYMGTQSQPQRTFPEI

QRRDSYYMTSSQLSTPLQQWRQGEYKCVVQHTASKSKKEIFRWPESPKAQASSVP

TAQPQAEGSLAKATTAPATTRNTGRGGEEKKKEKEKEEQEERETKTPECPSHTQPL

GVYLLTPAVQDLWLRDKATFTCFVVGSDLKDAHLTWEVAGKVPTGGVEEGLLER

HSNGSQSQHSRLTLPRSLWNAGTSVTCTLNHPSLPPQRLMALREPAAQAPVKLSLN

LLASSDPPEAASWLLCEVSGFSPPNILLMWLEDQREVNTSGFAPARPPPQPGSTTFW

AWSVLRVPAPPSPQPATYTCVVSHEDSRTLLNASRSLEVSYVTDHGPMK

Human IgG1 constant region, Uniprot: P01857

(SEQ ID NO: 71)

ASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Human IgG2 constant region, Uniprot: P01859

(SEQ ID NO: 72)

ASTKGPSVFPLAPCSRSTSESTAALGCLVKDYFPEPVTVSWNSGALTSGVHTFPAVL

QSSGLYSLSSVVTVPSSNFGTQTYTCNVDHKPSNTKVDKTVERKCCVECPPCPAPP

VAGPSVFLFPPKPKDTLMISRTPEVTCVVVDVSHEDPEVQFNWYVDGVEVHNAKT

KPREEQFNSTFRVVSVLTVVHQDWLNGKEYKCKVSNKGLPAPIEKTISKTKGQPRE

PQVYTLPPSREEMTKNQVSLTCLVKGFYPSDISVEWESNGQPENNYKTTPPMLDSD

GSFFLYSKLTVDKSRWQQGNVFSCSVMHEALHNHYTQKSLSLSPGK

Human IgG3 constant region, Uniprot: P01860

(SEQ ID NO: 73)

ASTKGPSVFPLAPCSRSTSGGTAALGCLVKDYFPEPVTVSWNSGALTSGVHTFPAV

LQSSGLYSLSSVVTVPSSSLGTQTYTCNVNHKPSNTKVDKRVELKTPLGDTTHTCPR

CPEPKSCDTPPPCPRCPEPKSCDTPPPCPRCPEPKSCDTPPPCPRCPAPELLGGPSVFL

FPPKPKDTLMISRTPEVTCVVVDVSHEDPEVQFKWYVDGVEVHNAKTKPREEQYN

STFRVVSVLTVLHQDWLNGKEYKCKVSNKALPAPIEKTISKTKGQPREPQVYTLPPS

REEMTKNQVSLTCLVKGFYPSDIAVEWESSGQPENNYNTTPPMLDSDGSFFLYSKL

TVDKSRWQQGNIFSCSVMHEALHNRFTQKSLSLSPGK

Human IgM constant region, Uniprot: P01871

(SEQ ID NO: 74)

GSASAPTLFPLVSCENSPSDTSSVAVGCLAQDFLPDSITLSWKYKNNSDISSTRGFPS

VLRGGKYAATSQVLLPSKDVMQGTDEHVVCKVQHPNGNKEKNVPLPVIAELPPKV

SVFVPPRDGFFGNPRKSKLICQATGFSPRQIQVSWLREGKQVGSGVTTDQVQAEAK

ESGPTTYKVTSTLTIKESDWLGQSMFTCRVDHRGLTFQQNASSMCVPDQDTAIRVF

AIPPSFASIFLTKSTKLTCLVTDLTTYDSVTISWTRQNGEAVKTHTNISESHPNATFSA

VGEASICEDDWNSGERFTCTVTHTDLPSPLKQTISRPKGVALHRPDVYLLPPAREQL

NLRESATITCLVTGFSPADVFVQWMQRGQPLSPEKYVTSAPMPEPQAPGRYFAHSIL

TVSEEEWNTGETYTCVAHEALPNRVTERTVDKSTGKPTLYNVSLVMSDTAGTCY

-continued

```
Human IgG4 constant region, Uniprot: P01861
                                                  (SEQ ID NO: 75)
ASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPSCPAPEF

LGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK


Human IgA1 constant region, Uniprot: P01876
                                                  (SEQ ID NO: 76)
ASPTSPKVFPLSLCSTQPDGNVVIACLVQGFFPQEPLSVTWSESGQGVTARNFPPSQ

DASGDLYTTSSQLTLPATQCLAGKSVTCHVKHYTNPSQDVTVPCPVPSTPPTPSPST

PPTPSPSCCHPRLSLHRPALEDLLLGSEANLTCTLTGLRDASGVTFTWTPSSGKSAV

QGPPERDLCGCYSVSSVLPGCAEPWNHGKTFTCTAAYPESKTPLTATLSKSGNTFRP

EVHLLPPPSEELALNELVTLTCLARGFSPKDVLVRWLQGSQELPREKYLTWASRQE

PSQGTTTFAVTSILRVAAEDWKKGDTFSCMVGHEALPLAFTQKTIDRLAGKPTHVN

VSVVMAEVDGTCY

Human IgA2 constant region, Uniprot: P01877
                                                  (SEQ ID NO: 77)
ASPTSPKVFPLSLDSTPQDGNVVVACLVQGFFPQEPLSVTWSESGQNVTARNFPPSQ

DASGDLYTTSSQLTLPATQCPDGKSVTCHVKHYTNPSQDVTVPCPVPPPPPCCHPRL

SLHRPALEDLLLGSEANLTCTLTGLRDASGATFTWTPSSGKSAVQGPPERDLCGCY

SVSSVLPGCAQPWNHGETFTCTAAHPELKTPLTANITKSGNTFRPEVHLLPPPSEEL

ALNELVTLTCLARGFSPKDVLVRWLQGSQELPREKYLTWASRQEPSQGTTTFAVTS

ILRVAAEDWKKGDTFSCMVGHEALPLAFTQKTIDRMAGKPTHVNVSVVMAEVDG

TCY

Human Ig kappa constant region, Uniprot: P01834
                                                  (SEQ ID NO: 78)
TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC
```

In some embodiments, the immunoglobulin-related compositions of the present technology comprise a heavy chain constant region that is at least 80%, at least 85%, at least 90%, at least 95%, at least 99%, or is 100% identical to SEQ ID NOs: 70-77. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 78

Additionally or alternatively, in some embodiments, the antibody or antigen binding fragment binds to the first extracellular loop of a CLDN18.2 polypeptide. In some embodiments, the CLDN18.2 polypeptide has the amino acid sequence of SEQ ID NO: 4. In certain embodiments, the first extracellular loop comprises the amino acid sequence of SEQ ID NO: 2 (see FIG. 2). In certain embodiments, the epitope is a conformational epitope or non-conformational epitope.

In one aspect, the present disclosure provides an antibody comprising a heavy chain (HC) amino acid sequence comprising SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, SEQ ID NO: 161, or a variant thereof having one or more conservative amino acid substitutions. Additionally or alternatively, in some embodiments, the immunoglobulin-related compositions of the present technology comprise a light chain (LC) amino acid sequence comprising SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, SEQ ID NO: 162, or a variant thereof having one or more conservative amino acid substitutions. In some embodiments, the immunoglobulin-related compositions of the present technology comprises a HC amino acid sequence and a LC amino acid sequence selected from the group consisting of: SEQ ID NO: 62 and SEQ ID NO: 63, SEQ ID NO: 64 and SEQ ID NO: 65, SEQ ID NO: 66 and SEQ ID NO: 67, SEQ ID NO: 68 and SEQ ID NO: 69, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 159 and SEQ ID NO: 160, and SEQ ID NO: 161 and SEQ ID NO: 162, respectively.

In any of the above embodiments of the immunoglobulin-related compositions, the HC and LC immunoglobulin variable domain sequences form an antigen binding site that binds to the first extracellular loop of a CLDN18.2 polypeptide. In certain embodiments, the first extracellular loop comprises the amino acid sequence of SEQ ID NO: 2. In some embodiments, the epitope is a conformational epitope or a non-conformational epitope.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one CLDN18.2 polypeptide. In some embodiments, the immunoglobulin-related compositions of the present technology bind at least one CLDN18.2 polypeptide with a dissociation constant ($K_D$) of about $10^{-3}$ M, $10^{-4}$M, $10^{-5}$M, $10^{-6}$M, $10^{-7}$M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, bispecific antibodies, or multi-specific antibodies. In some embodiments, the antibodies comprise a human antibody framework region.

In certain embodiments, the immunoglobulin-related composition includes one or more of the following characteristics: (a) a light chain immunoglobulin variable domain sequence that is at least 80%, at least 85%, at least 90%, at least 95%, or at least 99% identical to the light chain immunoglobulin variable domain sequence of any one of SEQ ID NOs: 37, 39, 41, 43, 45, 50-53, or 58-61; and/or (b) a heavy chain immunoglobulin variable domain sequence that is at least 80%, at least 85%, at least 90%, at least 95%, or at least 99% identical to the heavy chain immunoglobulin variable domain sequence of any one of SEQ ID NOs: 36, 38, 40, 42, 44, 46-49, or 54-57. In another aspect, one or more amino acid residues in the immunoglobulin-related compositions provided herein are substituted with another amino acid. The substitution may be a “conservative substitution” as defined herein.

In another aspect, the present disclosure provides a multi-specific (e.g., bispecific) antibody comprising: (a) a LC sequence that is at least 80%, at least 85%, at least 90%, at least 95%, or at least 99% identical to the LC sequence present in SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, or SEQ ID NO: 162; and/or (b) a HC sequence that is at least 80%, at least 85%, at least 90%, at least 95%, or at least 99% identical to the HC sequence present in SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, or SEQ ID NO: 161.

In certain embodiments, the immunoglobulin-related compositions contain an IgG1 constant region comprising one or more amino acid substitutions selected from the group consisting of N297A, K322A, L234A and L235A. Additionally or alternatively, in some embodiments, the immunoglobulin-related compositions contain an IgG4 constant region comprising a S228P mutation.

In one aspect, the present disclosure provides a multi-specific (e.g., bispecific) antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 79); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 80) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin or the heavy chain variable domain of the second immunoglobulin is selected from any one of SEQ ID NOs: 36, 38, 40, 42, 44, 46-49, or 54-57, and/or the light chain variable domain of the first immunoglobulin or the light chain variable domain of the second immunoglobulin is selected from any one of SEQ ID NOS: 37, 39, 41, 43, 45, 50-53, or 58-61.

Additionally or alternatively, in some embodiments, the heavy chain variable domain of the first immunoglobulin is selected from any one of SEQ ID NOs: 36, 38, 40, 42, 44, 46-49, or 54-57, the light chain variable domain of the first immunoglobulin is selected from any one of SEQ ID NOs: 37, 39, 41, 43, 45, 50-53, or 58-61, the heavy chain variable domain of the second immunoglobulin is selected from any one of SEQ ID NOS: 97, 99, 100, 101, 102, or 157, and the light chain variable domain of the second immunoglobulin is selected from any one of SEQ ID NOs: 98, 103, or 158.

In other embodiments, the heavy chain variable domain of the first immunoglobulin is selected from any one of SEQ ID NOs: 97, 99, 100, 101, 102, or 157, the light chain variable domain of the first immunoglobulin is selected from any one of SEQ ID NOs: 98, 103, or 158, the heavy chain variable domain of the second immunoglobulin is selected from any one of SEQ ID NOs: 36, 38, 40, 42, 44, 46-49, or 54-57, and the light chain variable domain of the second immunoglobulin is selected from any one of SEQ ID NOs: 37, 39, 41, 43, 45, 50-53, or 58-61.

In some aspects, the anti-CLDN18.2 immunoglobulin-related compositions described herein contain structural modifications to facilitate rapid binding and cell uptake and/or slow release. In some aspects, the anti-CLDN18.2 immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a $F(ab)'_2$ fragment is used to facilitate rapid binding and cell uptake and/or slow release.

In one aspect, the present technology provides a nucleic acid sequence encoding any of the immunoglobulin-related compositions described herein. Also disclosed herein are recombinant nucleic acid sequences encoding any of the antibodies described herein.

In another aspect, the present technology provides a host cell expressing any nucleic acid sequence encoding any of the immunoglobulin-related compositions described herein.

The immunoglobulin-related compositions of the present technology (e.g., an anti-CLDN18.2 antibody) can be monospecific, bispecific, trispecific or of greater multi-specificity. Multi-specific antibodies can be specific for different epitopes of one or more CLDN18.2 polypeptides or can be specific for both the CLDN18.2 polypeptide(s) as well as for heterologous compositions, such as a heterologous polypeptide or solid support material. See, e.g., WO 93/17715; WO 92/08802; WO 91/00360; WO 92/05793; Tutt et al., *J. Immunol.* 147:60-69 (1991); U.S. Pat. Nos. 5,573,920, 4,474,893, 5,601,819, 4,714,681, 4,925,648; 6,106,835; Kostelny et al., *J. Immunol.* 148:1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In one aspect, the present disclosure provides an anti-CD3 antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence of any one of SEQ ID NOs: 99-102, or SEQ ID NO: 157; and/or (b) the $V_L$ comprises an amino acid sequence of SEQ ID NO: 103 or SEQ ID NO: 158. In some embodiments, the anti-CD3 antibody or antigen binding fragment comprises heavy chain immunoglobulin variable domain ($V_H$) and light chain immunoglobulin variable domain ($V_L$) amino acid sequences selected from the group consisting of: SEQ ID NO: 101 and SEQ ID NO: 103; and SEQ ID NO: 157 and SEQ ID NO: 158, respectively. Additionally or alternatively, in some embodiments, the anti-CD3 antibody or antigen binding fragment is a monoclonal antibody, a chimeric antibody, a humanized antibody, a bispecific antibody, or multi-specific antibody. The antigen binding fragment may be selected from the group consisting of Fab, $F(ab')_2$, Fab', $scF_v$, and $F_v$.

Additionally or alternatively, in certain embodiments, the anti-CD3 antibody or antigen binding fragment further comprises a Fc domain of an isotype selected from the group consisting of IgG1, IgG2, IgG3, IgG4, IgA1, IgA2, IgM, IgD, and IgE. In some embodiments, the anti-CD3 antibody further comprises an IgG1 constant region comprising one or more amino acid substitutions selected from the group consisting of N297A, L234A, L235A, and K322A. In other embodiments, the anti-CD3 antibody comprises an IgG4 constant region comprising a S228P mutation. Additionally or alternatively, in some embodiments, the anti-CD3 antibody lacks α-1,6-fucose modifications.

In one aspect, the present disclosure provides a multi-specific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence (GGGGS) 3 (SEQ ID NO: 79); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence (GGGGS) 6 (SEQ ID NO: 80) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin or the heavy chain variable domain of the second immunoglobulin comprises any one of SEQ ID NOs: 99-102, or SEQ ID NO: 157, and/or the light chain variable domain of the first immunoglobulin or the light chain variable domain of the second immunoglobulin comprises SEQ ID NO: 103 or SEQ ID NO: 158.

Additionally or alternatively, in some embodiments, the anti-CD3 multi-specific antibody or antigen binding fragment binds to T cells, B-cells, myeloid cells, plasma cells, or mast-cells. Additionally or alternatively, in certain embodiments, the anti-CD3 multi-specific antibody or antigen binding fragment binds to CD3, GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, LMP2, p53, lung resistance protein (LRP), Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, GPC3, EpCAM, CD4, CD8, CD21, CD23, CD46, CD80, HLA-DR, CD74, CD22, CD14, CD15, CD16, CD123, TCR gamma/delta, NKp46, KIR, CD56, DLL3, PD-1, PD-L1, CD28, CD137, CD99, GloboH, CD24, STEAP1, B7H3, Polysialic Acid, OX40, OX40-ligand, peptide MHC complexes (with peptides derived from TP53, KRAS, MYC, EBNA1-6, PRAME, MART, tyronsinase, MAGEA1-A6, pmel17, LMP2, or WT1), or a small molecule DOTA hapten.

In another aspect, the present disclosure provides a composition comprising any and all embodiments of the anti-CD3 antibody or antigen binding fragment disclosed herein and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In yet another aspect, the present disclosure provides a method for treating cancer in a subject in need thereof, comprising administering to the subject an effective amount of any and all embodiments of the anti-CD3 antibody or antigen binding fragment disclosed herein. In another aspect, the present disclosure provides a method for treating cancer in a subject in need thereof, comprising administering to the subject an effective amount of a composition comprising any and all embodiments of the anti-CD3 antibody or antigen binding fragment disclosed herein and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

A. Methods of Preparing Anti-CLDN18.2 Antibodies of the Present Technology

General Overview. Initially, a target polypeptide is chosen to which an antibody of the present technology can be raised. For example, an antibody may be raised against the full-length CLDN18.2 protein, or to a portion of the first extracellular loop of the CLDN18.2 protein. Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from CLDN18.2 protein containing the first extracellular loop which is capable of eliciting an immune response.

It should be understood that recombinantly engineered antibodies and antibody fragments, e.g., antibody-related polypeptides, which are directed to CLDN18.2 protein and fragments thereof are suitable for use in accordance with the present disclosure.

Anti-CLDN18.2 antibodies that can be subjected to the techniques set forth herein include monoclonal and polyclonal antibodies, and antibody fragments such as Fab, Fab', $F(ab')_2$, Fd, scFv, diabodies, antibody light chains, antibody heavy chains and/or antibody fragments. Methods useful for the high yield production of antibody Fv-containing polypeptides, e.g., Fab' and $F(ab')_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes CLDN18.2 proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified CLDN18.2 protein or fragment thereof, a nucleic acid encoding CLDN18.2 protein or fragment thereof, or with a cell expressing the CLDN18.2 protein or fragment thereof. An appropriate immunogenic preparation can contain, e.g., a recombinantly-expressed CLDN18.2 protein or a chemically-synthesized CLDN18.2 peptide. The first extracellular loop of the CLDN18.2 protein, or a portion or fragment thereof, can be used as an immunogen to generate an anti-CLDN18.2 antibody that binds to the CLDN18.2 protein, or a portion or fragment thereof using standard techniques for polyclonal and monoclonal antibody preparation. In some embodiments, the antigenic CLDN18.2 peptide comprises at least 10, at least 20, at least 30, at least 40, at least 50, at least 60, at least 70, at least 80, at least 90, or at least 100 amino acid residues. Longer antigenic peptides are sometimes desirable over shorter antigenic peptides, depending on use and according to methods well known to those skilled in the art. Multimers of a given epitope are sometimes more effective than a monomer.

By way of example, but not by way of limitation, an immunogenic preparation may comprise, e.g., a recombinantly-expressed CLDN18.2 protein or a chemically-synthesized CLDN18.2 peptide comprising the amino acid sequence of SEQ ID NO: 4. The first extracellular loop of the CLDN18.2 protein, or a portion or fragment thereof, e.g., a CLDN18.2-EL1 having amino acid sequence of SEQ ID NO: 2, may be used as an immunogen to generate an anti-CLDN18.2 antibody that binds to the EL1 portion of the CLDN18.2 protein.

If needed, the immunogenicity of the CLDN18.2 protein (or fragment thereof) can be increased by fusion or conjugation to a carrier protein such as keyhole limpet hemocyanin (KLH) or ovalbumin (OVA). Many such carrier proteins are known in the art. One can also combine the CLDN18.2 protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

Alternatively, nanoparticles, for example, virus-like particles (VLPs), can be used to present antigens, e.g., CLDN18.2-EL1, to a host animal. Virus-like particles are multiprotein structures that mimic the organization and conformation of authentic native viruses without being infectious, since they do not carry any viral genetic material (Urakami A, et al, *Clin Vaccine Immunol* 24: e00090-17 (2017)). When introduced to a host immune system, VLPs can evoke effective immune responses, making them attractive carriers of foreign antigens. An important advantage of a VLP-based antigen presenting platform is that it can display antigens in a dense, repetitive manner. Thus, antigen-bearing VLPs are able to induce strong B-cell responses by effectively enabling the cross-linking of B cell receptors (BCRs). VLPs may be genetically manipulated to fine their properties, e.g., immunogenicity. These techniques are standard in the art.

The isolation of sufficient purified protein or polypeptide to which an antibody is to be raised may be time consuming and sometimes technically challenging. Additional challenges associated with conventional protein-based immunization include concerns over safety, stability, scalability and consistency of the protein antigen. Nucleic acid (DNA and RNA) based immunizations have emerged as promising alternatives. DNA vaccines are usually based on bacterial plasmids that encode the polypeptide sequence of candidate antigen, e.g., CLDN18.2. With a robust eukaryotic promoter, the encoded antigen can be expressed to yield enough levels of transgene expression once the host is inoculated with the plasmids (Galvin T. A., et al., *Vaccine* 2000, 18:2566-2583). Modern DNA vaccine generation relies on DNA synthesis, possibly one-step cloning into the plasmid vector and subsequent isolation of the plasmid, which takes significantly less time and cost to manufacture. The resulting plasmid DNA is also highly stable at room temperature, avoiding cold transportation and leading to substantially extended shelf-life. These techniques are standard in the art.

Alternatively, nucleic acid sequences encoding the antigen of interest, e.g., CLDN18.2, can be synthetically introduced into a mRNA molecule. The mRNA is then delivered into a host animal, whose cells would recognize and translate the mRNA sequence to the polypeptide sequence of the candidate antigen, e.g., CLDN18.2, thus triggering the immune response to the foreign antigen. An attractive feature of mRNA antigen or mRNA vaccine is that mRNA is a non-infectious, non-integrating platform. There is no potential risk of infection or insertional mutagenesis associated with DNA vaccines. In addition, mRNA is degraded by normal cellular processes and has a controllable in vivo half-life through modification of design and delivery methods (Kariko, K., et al., *Mol Ther* 16:1833-1840 (2008); Kauffman, K. J., et al., *J Control Release* 240, 227-234 (2016); Guan, S. & Rosenecker, *J., Gene Ther* 24, 133-143 (2017); Thess, A., et al., *Mol Ther* 23, 1456-1464 (2015)). These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization" or "priming") to a particular antigen, e.g., CLDN18.2 protein. In some embodiments, the immunization can occur as a result of vaccinating the individual with a vaccine containing the antigen. For example, the vaccine can be a CLDN18.2 vaccine comprising one or more CLDN18.2 protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated (e.g., boosting), or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4+ T cells. A first exposure to an antigen primes the immune system and additional exposure(s) results in a DTH.

Following appropriate immunization, the anti-CLDN18.2 antibody can be prepared from the subject's serum. If desired, the antibody molecules directed against the CLDN18.2 protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-CLDN18.2 monoclonal antibody. For example, in some embodiments, the anti-CLDN18.2 monoclonal antibody may be a human or a mouse anti-CLDN18.2 monoclonal antibody. For preparation of monoclonal antibodies directed towards the CLDN18.2 protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256:495-497); the trioma technique; the human B-cell hybridoma technique (See, e.g., Kozbor, et al., 1983. *Immunol. Today* 4:72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci. USA* 80:2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the CLDN18.2 protein. Alternatively, hybridomas expressing anti-CLDN18.2 monoclonal antibodies can be prepared by immunizing a subject and then isolating hybridomas from the subject's spleen using routine methods. See, e.g., Milstein et al., (Galfre and Milstein, *Methods Enzymol* (1981) 73:3-46). Screening the hybridomas using standard methods will produce monoclonal antibodies of varying specificity (i.e., for different epitopes) and affinity. A selected monoclonal antibody with the desired properties, e.g., CLDN18.2 binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of CLDN18.2 protein. Also, CPG-dinucleotide techniques can be used to enhance the immunogenic properties of the CLDN18.2 protein. Other manipulations include substituting or deleting particular amino acyl residues that contribute to instability of the antibody during storage or after administration to a subject, and affinity maturation techniques to improve affinity of the antibody of the CLDN18.2 protein.

Hybridoma Technique. In some embodiments, the antibody of the present technology is an anti-CLDN18.2 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-CLDN18.2 antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246:1275-1281, 1989) to allow rapid and effective identification of monoclonal Fab fragments with the desired specificity for a CLDN18.2 polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.,* 85:5879-5883, 1988; Chaudhary et al., *Proc. Natl. Acad. Sci U.S.A.,* 87:1066-1070, 1990; Brinkman et al., *J. Immunol. Methods* 182:41-50, 1995; Ames et al., *J. Immunol. Methods* 184:177-186, 1995; Kettleborough et al., *Eur. J. Immunol.* 24:952-958, 1994; Persic et al., *Gene* 187:9-18, 1997; Burton et al., *Advances in Immunology* 57:191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and $F(ab')_2$ fragments can also be employed using methods known in the art such as those disclosed in WO 92/22324; Mullinax et al., *BioTechniques* 12:864-869, 1992; and Sawai et al., *AJRI* 34:26-34, 1995; and Better et al., *Science* 240:1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-CLDN18.2 Antibodies. As noted above, the antibodies of the present technology can be produced through the application of recombinant DNA technology. Recombinant polynucleotide constructs encoding an anti-CLDN18.2 antibody of the present technology typically include an expression control sequence operably-linked to the coding sequences of anti-CLDN18.2 antibody chains, including naturally-associated or heterologous promoter regions. As such, another aspect of the technology includes vectors containing one or more nucleic acid sequences encoding an anti-CLDN18.2 antibody of the present technology. For recombinant expression of one or more of the polypeptides of the present technology, the nucleic acid containing all or a portion of the nucleotide sequence encoding the anti-CLDN18.2 antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-CLDN18.2 antibody, and the collection and purification of the anti-CLDN18.2 antibody, e.g., cross-reacting anti-CLDN18.2 antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with CLDN18.2 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-CLDN18.2 antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-CLDN18.2 antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-CLDN18.2 antibody, etc.).

Another aspect of the present technology pertains to anti-CLDN18.2 antibody-expressing host cells, which contain a nucleic acid encoding one or more anti-CLDN18.2 antibodies. The recombinant expression vectors of the present technology can be designed for expression of an anti-CLDN18.2 antibody in prokaryotic or eukaryotic cells. For example, an anti-CLDN18.2 antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-CLDN18.2 antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67:31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, *Academic Press*, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-CLDN18.2 antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20:2111-2118). Such alteration of nucleic acid sequences of the present technology can be carried out by standard DNA synthesis techniques.

In another embodiment, the anti-CLDN18.2 antibody expression vector is a yeast expression vector. Examples of vectors for expression in yeast *Saccharomyces cerevisiae* include pYepSec1 (Baldari, et al., 1987. *EMBO J.* 6:229-234), pMFa (Kurjan and Herskowitz, Cell 30:933-943, 1982), pJRY88 (Schultz et al., *Gene* 54:113-123, 1987), pYES2 (Invitrogen Corporation, San Diego, Calif.), and picZ (Invitrogen Corp, San Diego, Calif.). Alternatively, an anti-CLDN18.2 antibody can be expressed in insect cells using baculovirus expression vectors. Baculovirus vectors available for expression of polypeptides, e.g., anti-CLDN18.2 antibody, in cultured insect cells (e.g., SF9 cells) include the pAc series (Smith, et al., *Mol. Cell. Biol.* 3:2156-2165, 1983) and the pVL series (Lucklow and Summers, 1989. *Virology* 170:31-39).

In yet another embodiment, a nucleic acid encoding an anti-CLDN18.2 antibody of the present technology is expressed in mammalian cells using a mammalian expression vector. Examples of mammalian expression vectors include, e.g., but are not limited to, pCDM8 (Seed, *Nature* 329:840, 1987) and pMT2PC (Kaufman, et al., *EMBO J.* 6:187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-CLDN18.2 antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1:268-277, 1987), lymphoid-specific promoters (Calame and Eaton, *Adv. Immunol.* 43:235-275, 1988), promoters of T cell receptors (Winoto and Baltimore, *EMBO J.* 8:729-733, 1989) and immunoglobulins (Banerji, et al., 1983. *Cell* 33:729-740; Queen and Baltimore, Cell 33:741-748, 1983.), neuron-specific promoters (e.g., the neurofilament promoter; Byrne and Ruddle, *Proc. Natl. Acad. Sci. USA* 86:5473-5477, 1989), pancreas-specific promoters (Edlund, et al., 1985. *Science* 230:912- 916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3:537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-CLDN18.2 antibody can be expressed in bacterial cells such as *E. coli*, insect cells, yeast or mammalian cells. Mammalian cells are a suitable host for expressing nucleotide segments encoding immunoglobulins or fragments thereof. See Winnacker, From Genes To Clones, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89:49, 1986. Illustrative expression control sequences are promoters derived from endogenous genes, cytomegalovirus, SV40, adenovirus, bovine papillomavirus, and the like. Co et al., *J Immunol.* 148:1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

Non-limiting examples of suitable vectors include those designed for propagation and expansion, or for expression or both. For example, a cloning vector can be selected from the group consisting of the pUC series, the pBluescript series (Stratagene, LaJolla, Calif.), the pET series (Novagen™, Madison, Wis.), the pGEX series (Pharmacia Biotech, Uppsala, Sweden), and the pEX series (Clontech™, Palo Alto, Calif.). Bacteriophage vectors, such as lamda-GT10, lamda-GT11, lamda-ZapII (Stratagene), lamda-EMBL4, and lamda-NM1149, can also be used. Non-limiting examples of plant expression vectors include pBI110, pBI101.2, pBI101.3, pBI121 and pBIN19 (Clontech™). Non-limiting examples of animal expression vectors include pEUK-C1, pMAM and pMAMneo (Clontech™). The TOPO cloning system (Invitrogen™, Calsbad, CA) can also be used in accordance with the manufacturer's recommendations.

In certain embodiments, the vector is a mammalian vector. In certain embodiments, the mammalian vector contains at least one promoter element, which mediates the initiation of transcription of mRNA, the antibody-coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). Cellular elements can also be used (e.g., the human actin promoter). Non-limiting examples of mammalian expression vectors include, vectors such as pIRESIneo, pRetro-Off, pRetro-On, PLXSN, or pLNCX (Clonetech™ Labs, Palo Alto, Calif.), pcDNA3.1 (+/−), pcDNA/Zeo (+/−) or pcDNA3.1/Hygro (+/−) (Invitrogen, Calsbad, CA), PSVL and PMSG (Pharmacia, Uppsala, Sweden), pRSVcat (ATCC™ 37152), pSV2dhfr (ATCC™ 37146) and pBC12MI (ATCC™ 67109). Non-limiting examples of mammalian host cells that can be used in combination with such mammalian vectors include human Hela 293, HEK 293, H9 and Jurkat cells, mouse 3T3, NIH3T3 and C127 cells, Cos 1, Cos 7 and CV 1, quail QC1-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., *Molecular Cloning, a Laboratory Manual,* 2d edition, Cold Spring Harbor Press, Cold Spring Harbor, N.Y. (1989); and Ausubel et al., *Current Protocols in Molecular Biology, Greene Publishing Associates and* John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce an anti-CLDN18.2 antibody or antigen binding fragment described herein. Accordingly, provided herein are cells comprising a polynucleotide encoding an anti-CLDN18.2 antibody or antigen binding fragment thereof operably linked to a regulatory expression element (e.g., promoter) for expression of such sequences in the host cell. In certain embodiments, a vector encoding the heavy chain operably linked to a promoter and a vector encoding the light chain operably linked to a promoter can be co-expressed in the cell for expression of the entire anti-CLDN18.2 antibody or antigen binding fragment. In certain embodiments, a cell comprises a vector comprising a polynucleotide encoding both the heavy chain and the light chain of an anti-CLDN18.2 antibody or antigen binding fragment described herein that are operably linked to a promoter. In certain embodiments, a cell comprises two different vectors, a first vector comprising a polynucleotide encoding a heavy chain operably linked to a promoter, and a second vector comprising a polynucleotide encoding a light chain operably linked to a promoter. In certain embodiments, a first cell comprises a first vector comprising a polynucleotide encoding a heavy chain of an anti-CLDN18.2 antibody or antigen binding fragment described herein, and a second cell comprises a second vector comprising a polynucleotide encoding a light chain of an anti-CLDN18.2 antibody or antigen binding fragment described herein. In certain embodiments, provided herein is a mixture of cells comprising said first cell and said second cell. Examples of cells include, but are not limited to, a human cell, a human cell line, *E. coli* (e.g., *E. coli* TB-1, TG-2, DH5a, XL-Blue MRF' (Stratagene), SA2821 and Y1090), *B. subtilis, P. aerugenosa, S. cerevisiae, N. crassa*, insect cells (e.g., Sf9, Ea4) and the like.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-CLDN18.2 antibody or can be introduced on a separate vector. Cells stably transfected with the introduced nucleic acid can be identified by drug selection (e.g., cells that have incorporated the selectable marker gene will survive, while the other cells die).

A host cell that includes an anti-CLDN18.2 antibody of the present technology, such as a prokaryotic or eukaryotic host cell in culture, can be used to produce (i.e., express) recombinant anti-CLDN18.2 antibody. In one embodiment, the method comprises culturing the host cell (into which a recombinant expression vector encoding the anti-CLDN18.2 antibody has been introduced) in a suitable medium such that the anti-CLDN18.2 antibody is produced. In another embodiment, the method further comprises the step of isolating the anti-CLDN18.2 antibody from the medium or the host cell. Once expressed, collections of the anti-CLDN18.2 antibody, e.g., the anti-CLDN18.2 antibodies or the anti-CLDN18.2 antibody-related polypeptides are purified from culture media and host cells. The anti-CLDN18.2 antibody can be purified according to standard procedures of the art, including HPLC purification, column chromatography, gel electrophoresis and the like. In one embodiment, the anti-CLDN18.2 antibody is produced in a host organism by the method of Boss et al., U.S. Pat. No. 4,816,397. Usually, anti-CLDN18.2 antibody chains are expressed with signal sequences and are thus released to the culture media. However, if the anti-CLDN18.2 antibody chains are not naturally secreted by host cells, the anti-CLDN18.2 antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-CLDN18.2 antibodies, e.g., the anti-CLDN18.2 antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-CLDN18.2 antibody of the present technology is a single-chain anti-CLDN18.2 antibody. According to the present technology, techniques can be adapted for the production of single-chain antibodies specific to a CLDN18.2 protein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203:46-88, 1991; Shu, L. et al., *Proc. Natl. Acad. Sci. USA,* 90:7995-7999, 1993; and Skerra et al., *Science* 240:1038-1040, 1988.

Chimeric and Humanized Antibodies. In one embodiment, the anti-CLDN18.2 antibody of the present technology is a chimeric anti-CLDN18.2 antibody. In one embodiment, the anti-CLDN18.2 antibody of the present technology is a humanized anti-CLDN18.2 antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-CLDN18.2 antibodies, such as chimeric and humanized monoclonal antibodies, comprising both human and non-human portions, can be made using standard recombinant DNA techniques, and are within the scope of the present technology. For some uses, including in vivo use of the anti-CLDN18.2 antibody of the present technology in humans as well as use of these agents in in vitro detection assays, it is possible to use chimeric or humanized anti-CLDN18.2 antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240:1041-1043; Liu, et al., 1987. *Proc. Natl. Acad.* Sci. USA 84:3439-3443; Liu, et al., 1987. *J. Immunol.* 139:3521-3526; Sun, et al., 1987. *Proc. Natl. Acad. Sci. USA* 84:214-218; Nishimura, et al., 1987. *Cancer Res.* 47:999-1005; Wood, et al., 1985. *Nature* 314:446-449; Shaw, et al., 1988. *J. Natl. Cancer Inst.* 80:1553-1559; Morrison (1985) *Science* 229:1202-1207; Oi, et al. (1986) *BioTechniques* 4:214; Jones, et al., 1986. *Nature* 321:552-525; Verhoeyan, et al., 1988. *Science* 239:1534; Morrison, *Science* 229:1202, 1985; Oi et al., *BioTechniques* 4:214, 1986; Gillies et al., *J. Immunol. Methods,* 125:191-202, 1989; U.S. Pat. No. 5,807,715; and Beidler, et al., 1988. *J. Immunol.* 141:4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., Molecular Immunology, 28:489-498, 1991; Studnicka et al., *Protein Engineering* 7:805-814, 1994; Roguska et al., *PNAS* 91:969-973, 1994), and chain shuffling (U.S. Pat. No. 5,565,332). In one embodiment, a cDNA encoding a murine anti-CLDN18.2 monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240:1041-1043; Liu et al. (1987) *Proc. Natl. Acad. Sci. USA* 84:3439-3443; Liu et al. (1987) *J Immunol* 139:3521-3526; Sun et al. (1987) *Proc. Natl. Acad. Sci. USA* 84:214-218; Nishimura et al. (1987) *Cancer Res* 47:999-1005; Wood et al. (1985) *Nature* 314:446-449; and Shaw et al. (1988) *J. Natl. Cancer Inst.* 80:1553-1559; U.S. Pat. Nos. 6,180,370; 6,300,064; 6,696,248; 6,706,484; 6,828,422.

In one embodiment, the present technology provides the construction of humanized anti-CLDN18.2 antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-CLDN18.2 antibodies, heavy and light chain immunoglobulins.

CDR Antibodies. In some embodiments, the anti-CLDN18.2 antibody of the present technology is an anti-CLDN18.2 CDR antibody. Generally the donor and acceptor antibodies used to generate the anti-CLDN18.2 CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one needs to replace only as many as necessary to permit adequate binding of the resulting CDR-grafted antibody to CLDN18.2 protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-CLDN18.2 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-CLDN18.2 CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Multi-specific antibodies, such as bispecific antibodies (BsAb) and bispecific antibody fragments (BsFab) have at least one arm that specifically binds to, for example, CLDN18.2 and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, TCR gamma/delta, NKp46 and KIR. Exemplary $V_H$ and $V_L$ sequences that bind to a second target antigen (e.g., CD3) are shown in FIG. 25. In certain embodiments, the BsAbs are capable of binding to tumor cells that express CLDN18.2 antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for CLDN18.2 and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54 (22): 5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In some embodiments, the bispecific fusion protein is divalent, comprising, for example, an scFv with a single binding site for one antigen and another scFv fragment with a single binding site for a second antigen. In other embodiments, the bispecific fusion protein is tetravalent, comprising, for example, an immunoglobulin (e.g., IgG) with two binding sites for one antigen and two identical scFvs for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., CLDN18.2) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science* 321:974-977 (2008)). In some embodiments, BsAbs of the present technology comprise two single chain variable fragments (scFvs) in tandem have been designed such that an scFv that binds a tumor antigen (e.g., CLDN18.2) is linked with an scFv that engages a small molecule DOTA hapten.

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10 (10): 1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in a similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any CLDN18.2 immunoglobulin disclosed herein. In some certain embodiments, scFvs are linked to the C-terminal end of the light chain of any CLDN18.2 immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of a CLDN18.2 antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a G4S linker (SEQ ID NO: 163). In some certain embodiments, a BsAb of the present technology comprises a (G4S) n linker (SEQ ID NO: 164), wherein n is 1, 2, 3, 4, 5, 6, 7, 8, 9, 10, 11, 12, 13, 14, 15 or more.

Fc Modifications. In some embodiments, the anti-CLDN18.2 antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature,* 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-CLDN18.2 antibody of the present technology has an altered affinity for activating and/or inhibitory receptors, having a variant Fc region with one or more amino acid modifications, wherein said one or more amino acid modification is a N297 substitution with alanine, or a K322 substitution with alanine. Additionally or alternatively, in some embodiments, the Fc regions of the CLDN18.2 antibodies disclosed herein comprise two amino acid substitutions, Leu234Ala and Leu235Ala (so called LALA mutations) to eliminate FcγRIIa binding. The LALA mutations are commonly used to alleviate the cytokine induction from T cells, thus reducing toxicity of the antibodies (Wines B D, et al., *J Immunol* 164:5313-5318 (2000)).

Glycosylation Modifications. In some embodiments, anti-CLDN18.2 antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., CLDN18.2), without altering the functionality of the antibody, e.g., binding activity to the antigen. As used herein, “glycosylation sites” include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (hCLDN18.2-IgGln) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17:176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland);

each of which is incorporated herein by reference in its entirety. See, e.g., International Patent Application Publication WO 00/061739; U.S. Patent Application Publication No. 2003/0115614; Okazaki et al., 2004, *JMB,* 336:1239-49.

Fusion Proteins. In one embodiment, the anti-CLDN18.2 antibody of the present technology is a fusion protein. The anti-CLDN18.2 antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-CLDN18.2 antibodies. For instance, a region of additional amino acids, particularly charged amino acids, can be added to the N-terminus of the anti-CLDN18.2 antibody to improve stability and persistence during purification from the host cell or subsequent handling and storage. Also, peptide moieties can be added to an anti-CLDN18.2 antibody to facilitate purification. Such regions can be removed prior to final preparation of the anti-CLDN18.2 antibody. The addition of peptide moieties to facilitate handling of polypeptides are familiar and routine techniques in the art. The anti-CLDN18.2 antibody of the present technology can be fused to marker sequences, such as a peptide which facilitates purification of the fused polypeptide. In select embodiments, the marker amino acid sequence is a hexa-histidine peptide (SEQ ID NO: 165), such as the tag provided in a pQE vector (QIAGEN, Inc., Chatsworth, Calif), among others, many of which are commercially available. As described in Gentz et al., *Proc. Natl. Acad. Sci. USA* 86:821-824, 1989, for instance, hexa-histidine (SEQ ID NO: 165) provides for convenient purification of the fusion protein. Another peptide tag useful for purification, the "HA" tag, corresponds to an epitope derived from the influenza hemagglutinin protein. Wilson et al., *Cell* 37:767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270:3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8:52-58, 1995; Johanson et al., *J. Biol. Chem.,* 270: 9459-9471, 1995.

Labeled Anti-CLDN18.2 antibodies. In one embodiment, the anti-CLDN18.2 antibody of the present technology is coupled with a label moiety, i.e., detectable group. The particular label or detectable group conjugated to the anti-CLDN18.2 antibody is not a critical aspect of the technology, so long as it does not significantly interfere with the specific binding of the anti-CLDN18.2 antibody of the present technology to the CLDN18.2 protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{131}I$, $^{112}In$, $^{99}mTc$), other imaging agents such as microbubbles (for ultrasound imaging), $^{18}F$, $^{11}C$, $^{15}O$, $^{89}Zr$ (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6th Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-CLDN18.2 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally, simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-CLDN18.2 antibodies. In this case, antigen-coated particles are agglutinated by samples comprising the target antibodies. In this format, none of the components need be labeled and the presence of the target antibody is detected by simple visual inspection.

B. Identifying and Characterizing the Anti-CLDN18.2 Antibodies of the Present Technology Methods for identifying and/or screening the anti-CLDN18.2 antibodies of the present technology. Methods useful to identify and screen antibodies against CLDN18.2 polypeptides for those that possess the desired specificity to CLDN18.2 protein (e.g., those that bind to the first extracellular loop of CLDN18.2 protein, such as polypeptides comprising the amino acid sequence of SEQ ID NO: 2) include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity,* 2:373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.,* 86:4230-4, 1989); (4) mast cells can be incubated with reagents that cross-link their Fc-epsilon receptors and histamine release measured by enzyme immunoassay (Siraganian et al., *TIPS,* 4:432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72:1310-5, 1988); (3) the proliferation of peripheral blood mononuclear cells (PBMCs) in response to mitogens or mixed lymphocyte reaction can be measured using 3H-thymidine; (4) the phagocytic capacity of granulocytes, macrophages, and other phagocytes in PBMCs can be measured by placing PBMCs in wells together with labeled particles (Peters et al., *Blood,* 72:1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-CLDN18.2 antibodies of the present technology are selected using display of CLDN18.2 peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-CLDN18.2 antibodies of the present technology are selected using display of CLDN18.2 peptides on the surface of a yeast host cell. Methods useful for the isolation of $scF_v$ polypeptides by yeast surface display have been described by Kieke et al., *Protein Eng.* 1997 November; 10 (11): 1303-10.

In some embodiments, anti-CLDN18.2 antibodies of the present technology are selected using ribosome display. Methods useful for identifying ligands in peptide libraries using ribosome display have been described by Mattheakis et al., *Proc. Natl. Acad. Sci.* USA 91:9022-26, 1994; and Hanes et al., *Proc. Natl. Acad. Sci. USA* 94:4937-42, 1997.

In certain embodiments, anti-CLDN18.2 antibodies of the present technology are selected using tRNA display of CLDN18.2 peptides. Methods useful for in vitro selection of ligands using tRNA display have been described by Merryman et al., *Chem. Biol.,* 9:741-46, 2002.

In one embodiment, anti-CLDN18.2 antibodies of the present technology are selected using RNA display. Methods useful for selecting peptides and proteins using RNA display libraries have been described by Roberts et al. *Proc. Natl. Acad. Sci. USA,* 94:12297-302, 1997; and Nemoto et al., *FEBS Lett.,* 414:405-8, 1997. Methods useful for selecting peptides and proteins using unnatural RNA display libraries have been described by Frankel et al., *Curr. Opin. Struct. Biol.,* 13:506-12, 2003.

In some embodiments, anti-CLDN18.2 antibodies of the present technology are expressed in the periplasm of gram negative bacteria and mixed with labeled CLDN18.2 protein. See WO 02/34886. In clones expressing recombinant polypeptides with affinity for CLDN18.2 protein, the concentration of the labeled CLDN18.2 protein bound to the anti-CLDN18.2 antibodies is increased and allows the cells to be isolated from the rest of the library as described in Harvey et al., *Proc. Natl. Acad. Sci.* 22:9193-98 2004 and U.S. Pat. Publication No. 2004/0058403.

After selection of the desired anti-CLDN18.2 antibodies, it is contemplated that said antibodies can be produced in large volume by any technique known to those skilled in the art, e.g., prokaryotic or eukaryotic cell expression and the like. The anti-CLDN18.2 antibodies which are, e.g., but not limited to, anti-CLDN18.2 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of CLDN18.2 Binding. In some embodiments, a CLDN18.2 binding assay refers to an assay format wherein CLDN18.2 protein and an anti-CLDN18.2 antibody are mixed under conditions suitable for binding between the CLDN18.2 protein and the anti-CLDN18.2 antibody and assessing the amount of binding between the CLDN18.2 protein and the anti-CLDN18.2 antibody. The amount of binding is compared with a suitable control, which can be the amount of binding in the absence of the CLDN18.2 protein, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of CLDN18.2 protein binding to anti-CLDN18.2 antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-CLDN18.2 antibody is at least 1 percent greater than the binding observed in the absence of the candidate anti-CLDN18.2 antibody, the candidate anti-CLDN18.2 antibody is useful as an anti-CLDN18.2 antibody of the present technology.

Uses of the Anti-CLDN18.2 Antibodies of the Present Technology

General. The anti-CLDN18.2 antibodies of the present technology are useful in methods known in the art relating to the localization and/or quantitation of CLDN18.2 protein (e.g., for use in measuring levels of the CLDN18.2 protein within appropriate physiological samples, for use in diagnostic methods, for use in imaging the polypeptide, and the like). Antibodies of the present technology are useful to isolate a CLDN18.2 protein by standard techniques, such as affinity chromatography or immunoprecipitation. An anti-CLDN18.2 antibody of the present technology can facilitate the purification of natural immunoreactive CLDN18.2 proteins from biological samples, e.g., mammalian sera or cells as well as recombinantly-produced immunoreactive CLDN18.2 proteins expressed in a host system. Moreover, anti-CLDN18.2 antibodies can be used to detect an immunoreactive CLDN18.2 protein (e.g., in plasma, a cellular lysate or cell supernatant) in order to evaluate the abundance and pattern of expression of the immunoreactive polypeptide. The anti-CLDN18.2 antibodies of the present technology can be used diagnostically to monitor immunoreactive CLDN18.2 protein levels in tissue as part of a clinical testing procedure, e.g., to determine the efficacy of a given treatment regimen. As noted above, the detection can be facilitated by coupling (i.e., physically linking) the anti-CLDN18.2 antibodies of the present technology to a detectable substance.

Detection of CLDN18.2 protein. An exemplary method for detecting the presence or absence of an immunoreactive CLDN18.2 protein in a biological sample involves obtaining a biological sample from a test subject and contacting the biological sample with an anti-CLDN18.2 antibody of the present technology capable of detecting an immunoreactive CLDN18.2 protein such that the presence of an immunoreactive CLDN18.2 protein is detected in the biological sample. Detection may be accomplished by means of a detectable label attached to the antibody.

The term "labeled" with regard to the anti-CLDN18.2 antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-CLDN18.2 antibodies disclosed herein are conjugated to one or more detectable labels. For such uses, anti-CLDN18.2 antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled CLDN18.2-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive CLDN18.2 protein in a biological sample in vitro as well as in vivo. In vitro techniques for detection of an immunoreactive CLDN18.2 protein include enzyme linked immunosorbent assays (ELISAs), Western blots, immunoprecipitations, radioimmunoassay, and immunofluorescence. Furthermore, in vivo techniques for detection of an immunoreactive CLDN18.2 protein include introducing into a subject a labeled anti-CLDN18.2 antibody. For example, the anti-CLDN18.2 antibody can be labeled with a radioactive marker whose presence and location in a subject can be detected by standard imaging techniques. In one embodiment, the biological sample contains CLDN18.2 protein molecules from the test subject.

Immunoassay and Imaging. An anti-CLDN18.2 antibody of the present technology can be used to assay immunoreactive CLDN18.2 protein levels in a biological sample (e.g., human plasma) using antibody-based techniques. For example, protein expression in tissues can be studied with classical immunohistological methods. Jalkanen, M. et al., *J. Cell. Biol.* 101:976-985, 1985; Jalkanen, M. et al., *J. Cell. Biol.* 105:3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}I$, $^{121}I$, $^{131}I$), carbon ($^{14}C$), sulfur ($^{35}S$), tritium ($^{3}H$), indium ($^{112}In$), and technetium ($^{99}mTc$), and fluorescent labels, such as fluorescein, rhodamine, and green fluorescent protein (GFP), as well as biotin.

In addition to assaying immunoreactive CLDN18.2 protein levels in a biological sample, anti-CLDN18.2 antibodies of the present technology may be used for in vivo imaging of CLDN18.2. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-CLDN18.2 antibodies by labeling of nutrients for the relevant scFv clone.

An anti-CLDN18.2 antibody which has been labeled with an appropriate detectable imaging moiety, such as a radioisotope (e.g., $^{131}I$, $^{112}In$, $^{99}mTc$), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}mTc$. The labeled anti-CLDN18.2 antibody will then accumulate at the location of cells which contain the specific target polypeptide. For example, labeled anti-CLDN18.2 antibodies of the present technology will accumulate within the subject in cells and tissues in which the CLDN18.2 protein has localized.

Thus, the present technology provides a diagnostic method of a medical condition, which involves: (a) assaying the expression of immunoreactive CLDN18.2 protein by measuring binding of an anti-CLDN18.2 antibody of the present technology in cells or body fluid of an individual; (b) comparing the amount of immunoreactive CLDN18.2 protein present in the sample with a standard reference, wherein an increase or decrease in immunoreactive CLDN18.2 protein levels compared to the standard is indicative of a medical condition.

Affinity Purification. The anti-CLDN18.2 antibodies of the present technology may be used to purify immunoreactive CLDN18.2 protein from a sample. In some embodiments, the antibodies are immobilized on a solid support. Examples of such solid supports include plastics such as polycarbonate, complex carbohydrates such as agarose and SEPHAROSE™, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl) propionic acid can be employed as a means for cleaving a polypeptide from a solid support. (Brown et al., *Mol. Divers*, pp, 4-12 (1995); Rothschild et al., *Nucl. Acids Res.,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-CLDN18.2 Antibodies of the Present Technology

General. The anti-CLDN18.2 antibodies of the present technology are useful in diagnostic methods. As such, the present technology provides methods using the antibodies in the diagnosis of CLDN18.2 activity in a subject. Anti-CLDN18.2 antibodies of the present technology may be selected such that they have any level of epitope binding specificity and very high binding affinity to a CLDN18.2 protein. In general, the higher the binding affinity of an antibody the more stringent wash conditions can be performed in an immunoassay to remove nonspecifically bound material without removing target polypeptide. Accordingly, anti-CLDN18.2 antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that anti-CLDN18.2 antibodies used as diagnostic reagents have a sufficient kinetic on-rate to reach equilibrium under standard conditions in at least 12 h, at least five (5) h, or at least one (1) hour.

Anti-CLDN18.2 antibodies can be used to detect an immunoreactive CLDN18.2 protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of CLDN18.2 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-CLDN18.2 antibody or a population of anti-CLDN18.2 antibodies immobilized to a solid phase, and another anti-CLDN18.2 antibody or a population of anti-CLDN18.2 antibodies in solution. Typically, the solution anti-CLDN18.2 antibody or population of anti-CLDN18.2 antibodies is labeled. If an antibody population is used, the population can contain antibodies binding to different epitope specificities within the target polypeptide. Accordingly, the same population can be used for both solid phase and solution antibody. If anti-CLDN18.2 monoclonal antibodies are used, first and second CLDN18.2 monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the CLDN18.2 protein with the anti-CLDN18.2 antibody, a sample is incubated for a period that usually varies from about 10 min to about 24 hr and is usually about 1 hr. A wash step is then performed to remove components of the sample not specifically bound to the anti-CLDN18.2 antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive CLDN18.2 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the CLDN18.2 protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-CLDN18.2 antibodies can be joined to a linker molecule, such as biotin for attachment to a surface bound linker, such as avidin.

In some embodiments, the present disclosure provides an anti-CLDN18.2 antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the CLDN18.2 antibodies of the present technology. Macrocyclic chelates such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys (HSG)-D-Tyr-Lys (HSG)-$NH_2$; (ii) Ac-Lys (HSG) D-Tyr-Lys (HSG)-Lys (Tscg-Cys)-$NH_2$; (iii) DOTA-D-Asp-D-Lys (HSG)-D-Asp-D-Lys (HSG)-$NH_2$; (iv) DOTA-D-Glu-D-Lys (HSG)-D-Glu-D-Lys (HSG)-$NH_2$; (v) DOTA-D-Tyr-D-Lys (HSG)-D-Glu-D-Lys (HSG)-$NH_2$; (vi) DOTA-D-Ala-D-Lys (HSG)-D-Glu-D-Lys (HSG)-$NH_2$; (vii) DOTA-D-Phe-D-Lys (HSG)-D-Tyr-D-Lys (HSG)-$NH_2$; (viii) Ac-D-Phe-D-Lys (DOTA)-D-Tyr-D-Lys (DOTA)-$NH_2$; (ix) Ac-D-Phe-D-Lys (DTPA)-D-Tyr-D-Lys (DTPA)-$NH_2$; (x) Ac-D-Phe-D-Lys (Bz-DTPA)-D-Tyr-D-Lys (Bz-DTPA)-$NH_2$; (xi) Ac-D-Lys (HSG)-D-Tyr-D-Lys (HSG)-D-Lys (Tscg-Cys)-$NH_2$; (xii) DOTA-D-Phe-D-Lys (HSG)-D-Tyr-D-Lys (HSG)-D-Lys (Tscg-Cys)-$NH_2$; (xiii) (Tscg-Cys)-D-Phe-D-Lys (HSG)-D-Tyr-D-Lys (HSG)-D-Lys (DOTA)-$NH_2$; (xiv) Tscg-D-Cys-D-Glu-D-Lys (HSG)-D-Glu-D-Lys (HSG)-$NH_2$; (XV) (Tscg-Cys)-D-Glu-D-Lys (HSG)-D-Glu-D-Lys (HSG)-$NH_2$; (xvi) Ac-D-Cys-D-Lys (DOTA)-D-Tyr-D-Ala-D-Lys (DOTA)-D-Cys-$NH_2$; (xvii) Ac-D-Cys-D-Lys (DTPA)-D-Tyr-D-Lys (DTPA)-$NH_2$; (xviii) Ac-D-Lys (DTPA)-D-Tyr-D-Lys (DTPA)-D-Lys (Tscg-Cys)-$NH_2$; and (xix) Ac-D-Lys (DOTA)-D-Tyr-D-Lys (DOTA)-D-Lys (Tscg-Cys)-$NH_2$.

Other ring-type chelates such as macrocyclic polyethers, which are of interest for stably binding nuclides, such as 223Ra for RAIT are also contemplated.

B. Therapeutic Use of Anti-CLDN18.2 Antibodies of the Present Technology

In one aspect, the immunoglobulin-related compositions (e.g., antibodies or antigen binding fragments thereof) of the present technology are useful for the treatment of CLDN18.2-associated cancers, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, or any other neoplastic tissue that expresses CLDN18.2. In some embodiments, the CLDN18.2-associated cancer is a solid tumor. Such treatment can be used in patients identified as having pathologically high levels of the CLDN18.2 (e.g., those diagnosed by the methods described herein) or in patients diagnosed with a disease known to be associated with such pathological levels.

The compositions of the present technology may be employed in conjunction with other therapeutic agents useful in the treatment of CLDN18.2-associated cancers. For example, the antibodies or antigen binding fragments of the present technology may be separately, sequentially or simultaneously administered with at least one additional therapeutic agent-selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, T cells, and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, TYKERB™, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

Additionally or alternatively, in some embodiments, the antibodies or antigen binding fragments of the present technology may be separately, sequentially or simultaneously administered with at least one additional immunomodulating/stimulating antibody including but not limited to anti-PD-1 antibody, anti-PD-L1 antibody, anti-PD-L2 antibody, anti-CTLA-4 antibody, anti-TIM3 antibody, anti-4-1BB antibody, anti-CD73 antibody, anti-GITR antibody, and anti-LAG-3 antibody.

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intratumorally, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-CLDN18.2 antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-CLDN18.2 antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-CLDN18.2 antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting cancer in a subject in vivo comprising (a) administering to the subject an effective amount of an antibody (or antigen binding fragment thereof) of the present technology, wherein the antibody is configured to localize to a cancer cell expressing CLDN18.2 and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}Y$, $^{90}Y$, $^{89}Sr$, $^{165}Dy$, $^{186}Re$, $^{188}Re$, $^{177}Lu$, and $^{67}Cu$. Examples of alpha particle-emitting isotopes include $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, and $^{255}Fm$. Examples of Auger-emitters include $^{111}In$, $^{67}Ga$, $^{51}Cr$, $^{58}Co$, $^{99m}Tc$, $^{103m}Rh$, $^{195m}pt$, $^{119}Sb$, $^{161}Ho$, $^{189m}Os$, $^{192}Ir$, $^{201}Tl$, and $^{203}Pb$. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity. Optimally, an effective amount (e.g., dose) of an anti-CLDN18.2 antibody described herein will provide therapeutic benefit without causing substantial toxicity to the subject. Toxicity of the anti-CLDN18.2 antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-CLDN18.2 antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics, Ch.* 1 (1975).

Formulations of Pharmaceutical Compositions. According to the methods of the present technology, the anti-CLDN18.2 antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA 18th ed., 1990). The pharmaceutical compositions are generally formulated as sterile, substantially isotonic and in full compliance with all Good Manufacturing Practice (GMP) regulations of the U.S. Food and Drug Administration. The pharmaceutical composition may further comprise an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-CLDN18.2 antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-CLDN18.2 antibody named in this technology can be present in unsalified or unesterified form, or in salified and/or esterified form, and the naming of such anti-CLDN18.2 antibody is intended to include both the original (unsalified and unesterified) compound and its pharmaceutically-acceptable salts and esters. Also, certain embodiments of the present technology can be present in more than one stereoisomeric form, and the naming of such anti-CLDN18.2 antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-CLDN18.2 antibody, use thereof in the compositions is contemplated. Supplementary active compounds can also be incorporated into the compositions.

A pharmaceutical composition of the present technology is formulated to be compatible with its intended route of administration. The anti-CLDN18.2 antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-CLDN 18.2 antibody can optionally be administered in combination with other agents that are at least partly effective in treating various CLDN18.2-associated cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-CLDN18.2 antibody of the present technology in the required amount in an appropriate solvent with one or a combination of ingredients enumerated above, as required, followed by filtered sterilization. Generally, dispersions are prepared by incorporating the anti-CLDN18.2 antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-CLDN18.2 antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-CLDN18.2 antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-CLDN18.2 antibody is formulated into ointments, salves, gels, or creams as generally known in the art.

The anti-CLDN18.2 antibody can also be prepared as pharmaceutical compositions in the form of suppositories (e.g., with conventional suppository bases such as cocoa butter and other glycerides) or retention enemas for rectal delivery.

In one embodiment, the anti-CLDN18.2 antibody is prepared with carriers that will protect the anti-CLDN18.2 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

T cells Bound to Multi-specific Binding Molecules of the Present Technology. Without being bound by any theory, it is believed that when the anti-CD3 multi-specific binding molecules provided herein (e.g., CLDN 18.2×CD3) are bound to T cells, by, for example, procedures such as those described herein, an anti-CD3 scFv of the multi-specific binding molecule binds to CD3 on the surface of the T cell. Without being bound by any theory, it is believed that binding of the multi-specific binding molecule to the T cell (i.e., binding of an anti-CD3 scFv to CD3 expressed on the T cell) activates the T cell, and consequently, allows for the T cell receptor-based cytotoxicity to be redirected to desired tumor targets, bypassing MHC restrictions.

Thus, the present disclosure also provides T cells which are bound to a multi-specific binding molecule of the present technology. In specific embodiments, the T cells are bound to the multi-specific binding molecule noncovalently. In specific embodiments, the T cells are autologous to a subject to whom the T cells are to be administered. In specific embodiments, the T cells are allogeneic to a subject to whom the T cells are to be administered. In specific embodiments, the T cells are human T cells.

In specific embodiments, the T cells which are bound to multi-specific binding molecules of the invention are used in accordance with the therapeutic methods described herein. In specific embodiments, the T cells which are bound to multi-specific binding molecules of the present disclosure are used as part of a combination therapy as described below.

In specific embodiments involving combination therapy with infusion of T cells, provided herein is a pharmaceutical composition comprising (a) a multi-specific binding molecule described herein; (b) T cells; and/or (c) a pharmaceutically effective carrier. In specific embodiments, the T cells are autologous to the subject to whom the T cells are administered. In certain embodiments, the T cells are allogeneic to the subject to whom the T cells are administered. In specific embodiments, the T cells are either bound or not bound to the multi-specific binding molecule. In specific embodiments, the binding of the T cells to the multi-specific binding molecule is noncovalently. In specific embodiments, the T cells are human T cells. Methods that can be used to bind multi-specific binding molecules to T cells are known in the art. See, e.g., Lum et al., 2013, *Biol Blood Marrow Transplant,* 19:925-33, Janeway et al., *Immunobiology: The Immune System in Health and Disease,* 5th edition, New York: Garland Science; Vaishampayan et al., 2015, *Prostate Cancer,* 2015:285193, and Stromnes et al., 2014, *Immunol Rev.* 257 (1): 145-164.

In a specific embodiment, the administering of a multi-specific binding molecule provided herein, polynucleotide, vector, or cell encoding the multi-specific binding molecule, or a pharmaceutical composition comprising the multi-specific binding molecule is performed after treating the patient with T cell infusion. In specific embodiments the T cell infusion is performed with T cells that are autologous to the subject to whom the T cells are administered. In specific embodiments, the T cell infusion is performed with T cells that are allogeneic to the subject to whom the T cells are administered. In specific embodiments, the T cells can be bound to molecules identical to a multi-specific binding molecule as described herein. In specific embodiments, the binding of the T cells to molecules identical to the multi-specific binding molecule is noncovalently. In specific embodiments, the T cells are human T cells.

C. Kits

The present technology provides kits for the detection and/or treatment of CLDN18.2-associated cancers, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of CLDN18.2-associated cancers. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive CLDN18.2 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, bispecific, or multi-specific anti-CLDN18.2 antibodies of the present technology (or antigen binding fragments thereof) capable of binding a CLDN18.2 protein in a biological sample; means for determining the amount of the CLDN18.2 protein in the sample; and means for comparing the amount of the immunoreactive CLDN18.2 protein in the sample with a standard. One or more of the anti-CLDN18.2 antibodies may be labeled. The kit components, (e.g., reagents) can be packaged in a suitable container. The kit can further comprise instructions for using the kit to detect the immunoreactive CLDN18.2 protein.

For antibody-based kits, the kit can comprise, e.g., 1) a first antibody, e.g. a humanized, chimeric, bispecific, or multi-specific CLDN18.2 antibody of the present technology (or an antigen binding fragment thereof), attached to a solid support, which binds to a CLDN18.2 protein; and, optionally; 2) a second, different antibody which binds to either the CLDN18.2 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a CLDN18.2 protein in vitro or in vivo, or for treatment of CLDN18.2-associated cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative anti-CLDN18.2 antibodies of the present technology.

Example 1: Materials and Methods

Construction of hCLDN18.2 and hCLDN18.1 Gene Expression Vectors. Human cDNA encoding CLDN18.2 protein (SEQ ID NO: 4, shown in FIG. 10) was cloned into a pCMV3 expression vector (Sino Biological US Inc., Chesterbrook, PA), and was used for stable cell line generation and as DNA immunogen for mouse immunization. Similarly, human CLDN18.1 cDNA (SEQ ID NO: 5, shown in FIG. 11) was cloned into a pCMV3 expression vector and used for stable cell line generation. The human CLDN18.1 cell lines were used in a counter screen for selectivity.

Figure 5:
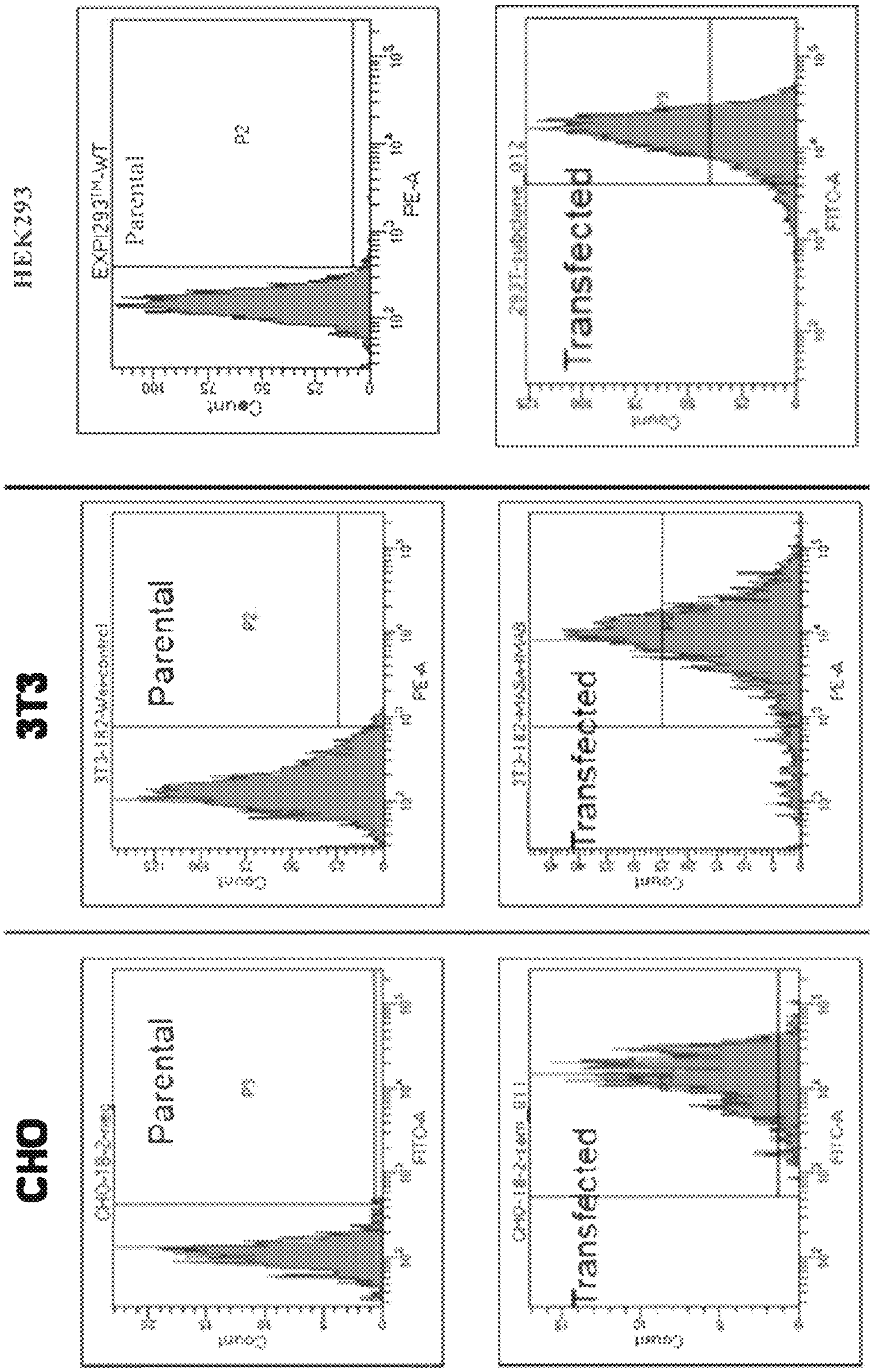
FIG. 5 shows cell lines (e.g., CHO, 3T3 and HEK293) that stably express human CLDN18.2 (analyzed using the benchmark antibody IMAB362, produced according to sequences from imgt.org/3Dstructure-DB/cgi/details.cgi?pdbcode=10473).

Generation of cell lines expressing hCLDN18.2 and hCLDN18.1. The constructed pCMV3-hCLDN18.2 and pCMV3-hCLDN18.1 expression plasmids were used to transfect cells for the development of the following stable or transient cell lines: 1) 3T3-hCLDN18.2, a mouse embryo fibroblast cell line, which was used for boosting mouse immunizations; 2) CHO-hCLDN18.2, which was used for antibody screening by ELISA and FACS; 3) HEK293-hCLDN18.2, which was used for antibody screening by ELISA and FACS; 4) HEK293-hCLDN18.1, which was used for antibody counter-screening. For the stable cell lines, all the final selected clones exhibited high expression levels of the target proteins. As shown in FIG. 5, all the 3 cells lines transfected with pCMV3-hCLDN18.2 exhibited at least 100 times greater expression of hCLDN18.2 than the parental control cell line.

Figure 6:
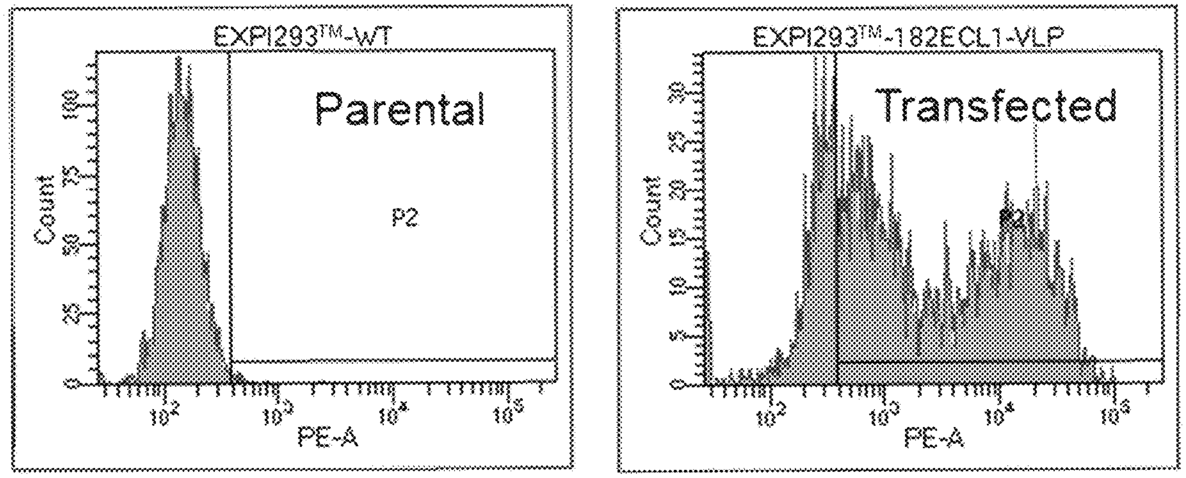
FIG. 6 shows Virus-like-particles (VLPs) that express human CLDN18.2 EL1 (analyzed using the benchmark antibody IMAB362, produced according to sequences from imgt.org/3Dstructure-DB/cgi/details.cgi?pdbcode=10473). More than 90% of the purified VLPs (Right) were expressing hCLDN18.2 EL1 compared to control (Left).

Expression of hCLDN18.2-EL1 in virus-like-particles (VLPs). To raise an anti-hCLDN18.2 specific antibody, the EL1 region was targeted because CLDN18.2 and 18.1 share identical EL2 sequences. To drive an immune response towards the EL1 region, a vector was constructed to express the hCLDN18.2 EL1 region in virus-like particles (VLPs). pEF6-CLDN18.2EL1 and a pEF6-vector (THERMO FISHER SCIENTIFIC™, Waltham MA) carrying a chimeric gene of CLDN18.2EL1 with CD81-cytosolic domains (pEF6-CLDN18.2EL1-CD81cd) were transfected to Expi293™ cells using the following protocol: Expi293" cells were co-transfected with pEF6-CLDN18.2EL1 or pEF6-CLDN18.2EL1-CD81cd and VLP-core coding vector with 180 μl-Epifectamine in 4 mL of OptiMEM™ for 24 hours at 4° C. with rotation. After 24 hours of transfection, cell suspension was added to 26 mL of Expi293™ expression medium and cultured at 37° C. with shaking at 125 rpm. At 24 hours in the shaking culture, enhancers 1 and 2 of the EXPI293™ MembranePro Expression System (THERMO FISHER SCIENTIFIC™, Waltham MA) were added at 150 μl and 1.5 mL, respectively, and further cultured for another 24 hours. Cells were subsequently centrifuged for FACS and the supernatant was collected for VLP precipitation. Cells were probed with mouse anti-CEA Ab followed by anti-mouse-PE conjugate. Total mouse IgG was used as an isotype control. FACS analysis showed that more than 90% of the purified VLPs were expressing hCLDN18.2 EL1 (FIG. 6). The purified VLPs were used for boost immunizations in mice.

Human CLDN18.2- and CLDN18.1-expressing cancer cell lines. To facilitate antibody characterization, in vitro cell killing assay development, and animal xenograft model development, the following cancer cell lines were purchased from ATCC™ Manassas, VA: 1) Gastric cancer cell lines Kato III, NCI-N87, NUGC4 and SNU-16, all of which express CLDN18.2; and 2) Lung cancer cell line A529, which expresses CLDN18.1.

Mouse immunization. Balb/C mice were immunized with eukaryotic expression vectors encoding CLDN18.2. Briefly, 70 μg pCMV3-hCLDN18.2 plasmid was injected intramuscularly using HELIOS® Gene Gun System (Bio-rad, Hercules CA) every two weeks for up to four times, and a final boost with $10^7$ 3T3-hCLDN18.2 cells and 10 μg VLPs expressing hCLDN18.2-EL1 was co-administered. Serum titers were monitored using CHO-hCLDN18.2 cell-based ELISA assays during the immunization course using the benchmark IMAB362 antibody as a positive control.

Hybridoma fusion, screening, and subcloning. After the final boost immunization, three mice that had high serum titer against the benchmark IMAB362 antibody were chosen for hybridoma fusion experiments. Three days after the final boost, freshly harvested mouse B-cells from lymph nodes and spleen were co-pelleted with mouse NS0 myeloma cells by centrifugation and fused by electroporation. The fused cells were resuspended in HAT selection medium and distributed into 96-well microtiter plates (60 plates for each fusion). Hybridomas were grown to at least 50% confluence (10-14 days post fusion) and then screened for production of CLDN18.2-specific antibody using CHO-hCLDN18.2 cell-based ELISA with IMAB362 as a positive control. Positive clones were then confirmed by FACS analysis with CLDN18.2- and CLDN18.1-expressing cells. Only those clones with specific and stronger binding signals than the benchmark IMAB362 antibody were advanced for subcloning, and 2-3 rounds of limiting dilution cloning were performed to confirm clonality.

FACS cell binding assays. Cells were incubated with 5 μg/mL of the primary anti-claudin 18.2 antibodies for thirty minutes at 4° C. in PBS, and then a secondary phycoerythrin-labeled antibody specific for human Fc was added after washing off excessive primary antibody. Cells were fixed with 1% paraformaldehyde (PFA) prior to analysis on FACSCalibur™ cytometer (BD biosciences, Franklin Lakes, New Jersey, U.S.). Controls were cells with secondary antibody only, for which the mean fluorescent intensity (MFI) was set to 5.

Antibody purification and characterization. After screening about 4000 hybridoma clones, 5 clones that showed higher binding signal than the benchmark IMAB362 antibody were selected for subcloning. The cells of the 5 final subcloned hybridomas were expanded to 50-100 ml culture in a density about $10^6$ cells/ml, and the secreted antibodies were purified using standard protein A or protein G columns. The purified antibodies were subjected to characterization to further confirm their binding specificity and affinity with recombinant and endogenous cell lines.

Antibody gene sequencing. The heavy and light chain variable genes of the five selected lead murine antibodies were amplified by PCR using degenerated primers (targeting the leader sequence region) disclosed in Table 2 and the PCR products were used directly for sequencing as a first pass. To have clean readouts, a TA cloning/sequencing step was added as a final confirmation. The $V_H$ and $V_L$ sequences were cloned into human IgG1 constant regions to form the chimeric antibodies. The plasmids expressing the respective heavy and light chain of a chosen anti-CLDN18.2 antibody was transiently co-expressed in HEK293 cells. Co-transfection was performed with polyethyleneimine (PEI) as the transfection reagent. The supernatant was collected 6-8 days after transfection. Antibodies were purified by protein A chromatography. The amino acid sequences of the heavy and light chain variable regions of the five mouse clones (SEQ ID NOs: 36-45) are shown in FIG. 13.

TABLE 2

| Primer Names | Primer Sequences | SEQ ID NO |
|---|---|---|
| VL-F1 | TGGGTATCTGGTACCTGTGGG | SEQ ID NO: 104 |
| VL-F2 | AGGCTGTTGGTGCTGATGTTCTGGATT | SEQ ID NO: 105 |
| VL-F3 | CTCTTGGTGCTTCTGTTGTTCTGGATTCCT | SEQ ID NO: 106 |
| VL-F4 | CTGTTAGTGCTCTGGATTCGGGAAACC | SEQ ID NO: 107 |
| VL-F5 | GGGCTGCTTKTGYTCTGKATCYCT | SEQ ID NO: 108 |
| VL-F6 | CTAGGGSTGCTKVTRCTCTGGATCCCWGGW | SEQ ID NO: 109 |
| VL-F7 | CTGYTATGGGTRCTGCKGCTCTGG | SEQ ID NO: 110 |
| VL-F8 | TTSYTGCTAATCAGTGYCWCAGTYRYAATG | SEQ ID NO: 111 |
| VL-F9 | GTCACAGTCATAGTGTCTAATGGA | SEQ ID NO: 112 |
| VL-F10 | GGKCTCYTGTTGCTCTGKYTTCMWGGT | SEQ ID NO: 113 |
| VL-F11 | GGMWTCTTGTTGCTCTGGTTTCCAGGT | SEQ ID NO: 114 |
| VL-F12 | CAGGTCCTGGSGTTGCTGCTGCTG | SEQ ID NO: 115 |
| VL-F13 | TTTCTACTGCTCTGTGTGTCTGGT | SEQ ID NO: 116 |
| VL-F14 | YTKCTSTGGTTRTMTGGWGYTGAWGGR | SEQ ID NO: 117 |
| VL-F15 | CAGKTYYTBGKRYTYYTKCTKYTCTGG | SEQ ID NO: 118 |
| VL-F16 | CTGCTAATCAGTGCCTCAGTCATAATATCC | SEQ ID NO: 119 |
| VL-F17 | TTCAGCTTCCTGCTAATCAGTGCYTCA | SEQ ID NO: 120 |
| VL-F18 | CTRTKGGTGCTGMTGYTCTGGRTTCCW | SEQ ID NO: 121 |
| VL-F19 | TTGCTCTKKTTTCMAGGTAYCARATGT | SEQ ID NO: 122 |
| VL-F20 | CAGTTCCTGTTTCTGTTAGTGCTCTGG | SEQ ID NO: 123 |
| VL-F21 | CAGGTCYTKGYRTTSSTGYTKCTSTGG | SEQ ID NO: 124 |
| VL-F22 | GCCACCATGGRYWTHMRRRTG | SEQ ID NO: 125 |
| mVL-R | ACTGGATGGTGGGAAGAT | SEQ ID NO: 126 |
| mVH-R | AGGGGCCAGTGGATAGAC | SEQ ID NO: 127 |
| mIgG1-R | ATAGACAGATGGGGGTGTCGTTTTGGC | SEQ ID NO: 128 |
| mIgG2a-R | CTTGACCAGGCATCCTAGAGTCA | SEQ ID NO: 129 |
| mIgG2b-R | AGGGGCCAGTGGATAGACTGATGG | SEQ ID NO: 130 |
| mIgG3-R | AGGGACCAAGGGATAGACAGATGG | SEQ ID NO: 131 |
| mH1 | SARGTNMAGCTGSAGSAGTC | SEQ ID NO: 132 |
| mH2 | SARGTNMAGCTGSAGSAGTCWGG | SEQ ID NO: 133 |
| mK-F | GAYATTGTGMTSACMCARWCTMCA | SEQ ID NO: 134 |
| mKL-R | GGATGGTGGGAAGATGGATACAGTTGGTGC | SEQ ID NO: 135 |
| VH-F1 | ATGATGGTGTTAAGTCTTCTGTACCTG | SEQ ID NO: 136 |
| VH-F2 | CTGTTSACAGYCYTTCCKGGTATCCTG | SEQ ID NO: 137 |
| VH-F3 | RCATTYCCAAGCTGTRTCCTDTCC | SEQ ID NO: 138 |
| VH-F4 | CTGCTGMYTGTCCCTGCATATGTC | SEQ ID NO: 139 |
| VH-F5 | CTCYTGTCAGDAACTGCAGGYGTC | SEQ ID NO: 140 |
| VH-F6 | ATGGGATGGAGCYGKATCWTBCTCTTY | SEQ ID NO: 141 |
| VH-F7 | CACTGGATCTTTCTCTCCCTG | SEQ ID NO: 142 |

TABLE 2-continued

| Primer Names | Primer Sequences | SEQ ID NO |
|---|---|---|
| VH-F8 | ATGGGATGGAGCTATATCWTBCTCTTY | SEQ ID NO: 143 |
| VH-F9 | GCAACAGCYWYMGGTGTCCACTCC | SEQ ID NO: 144 |
| VH-F10 | CTGATGGCAGTGGTTAYAGGGGTC | SEQ ID NO: 145 |
| VH-F11 | KCADYARCTACAGGTGYYCACTCC | SEQ ID NO: 146 |
| VH-F12 | CTTTTAMAWGGTRTCCAGTGT | SEQ ID NO: 147 |
| VH-F13 | GCTCTTTTAAAAGGGGTCCAG | SEQ ID NO: 148 |
| VH-F14 | CTGAGCTGTGYWTTYATTRTT | SEQ ID NO: 149 |
| VH-F15 | CTTGTCSTTVTTTTAAAAGGTGTC | SEQ ID NO: 150 |
| VH-F16 | ATGCTGTTAGGGCTGGTTTTC | SEQ ID NO: 151 |
| VH-F17 | TTCCTGATGGCAGCTGCCCAAAGT | SEQ ID NO: 152 |
| VH-F18 | CTGTTSACAGCCWTTCCTGGT | SEQ ID NO: 153 |
| VH-F19 | CTGGCATTACTCTTCTGCCTG | SEQ ID NO: 154 |

R = AG, Y = CT, M = AC, K = GT, S = CG, W = AT, H = ACT, B = CGT, V = ACG, D = AGT, N = ACGT

Humanization of 32G4 and 47D10 clones. The variable regions of mouse clones 32G4 and 47D10, including $V_H$ and $V_L$, were humanized using germline CDR grafting. Briefly, the original murine sequences were aligned to all human germline sequences. The original mouse and closest matching germline sequences were analyzed for sequence liabilities and the most appropriate germline frameworks were selected. Complementarity determining regions (CDRs) from the parent mouse anti-CLDN18.2 antibodies were grafted onto the human frameworks and back mutations introduced as necessary. For both 32G4 and 47D10, four humanized $V_H$ and four humanized $V_L$ sequences were generated. The four $V_H$ and $V_L$ sequence variants from each clone may be combined to generate 16 humanized antibody variants for 32G4 or 47D10. The amino acid sequences of the four humanized $V_H$ and $V_L$ variants of 32G4 and 47D10 are shown in FIG. 14 and FIG. 15, respectively.

Construction of humanized full IgG1 32G4 and 47D10 expression constructs. Two humanized full IgG1 antibody variants for 32G4 and 47D10 were constructed and used for further characterization. The amino acid sequences of the two full humanized IgG1 antibodies from 32G4 and 47D10 are shown in FIG. 16 and FIG. 17, respectively.

Engineering and expression of anti-CLDN18.2×CD3 bispecific antibodies. The variable heavy and light chain gene sequences of the humanized 32G4 variants V8 and V9, and humanized 47D10 variants V6 and V7 anti-CLDN18.2 antibodies were codon optimized, synthesized, and inserted into a mammalian expression plasmid with the constant region gene of human IgG1 (contains LALA mutation: L234A and L235A) respectively. The humanized SP34 or OKT3 anti-CD3 scFv was attached to the C-terminus of the light chain of the anti-CLDN18.2 antibodies. Ten anti-CLDN18.2×CD3 bispecific antibody constructs were made: 32G4-V8×OKT3, 32G4-V9×OKT3, 47D10-V6×OKT3, 47D10-V7×OKT3, 32G4-V8×huSP34, 32G4-V9×huSP34, 47D10-V6×huSP34, 47D10-V7×huSP34, 32G4-V8×huSP34-v5, and 47D10-V7×huSP34-v5. The final sequences were confirmed by forward and reverse sequencing of the inserts. The amino acid sequences of the ten anti-CLDN18.2×CD3 bispecific antibodies are shown in FIGS. 20-23 and 26. The plasmids expressing the respective heavy and light chain of a particular anti-CLDN18.2×CD3 bispecific antibodies were transiently co-expressed in HEK293 cells. Co-transfection was performed with polyethyleneimine (PEI) as the transfection reagent. The supernatant was collected 6-8 days after transfection. Bispecific antibodies were purified by protein A chromatography.

Example 2: Characterization of Anti-CLDN18.2 Antibodies of the Present Technology Five clones (32G4, 47D10, 29G4, 31A6 and 15B10) were selected based on their binding affinity and selective binding to human CLDN18.2 protein. FACS data display the MFI value in the upper right panel of each plot.

Figure 7:
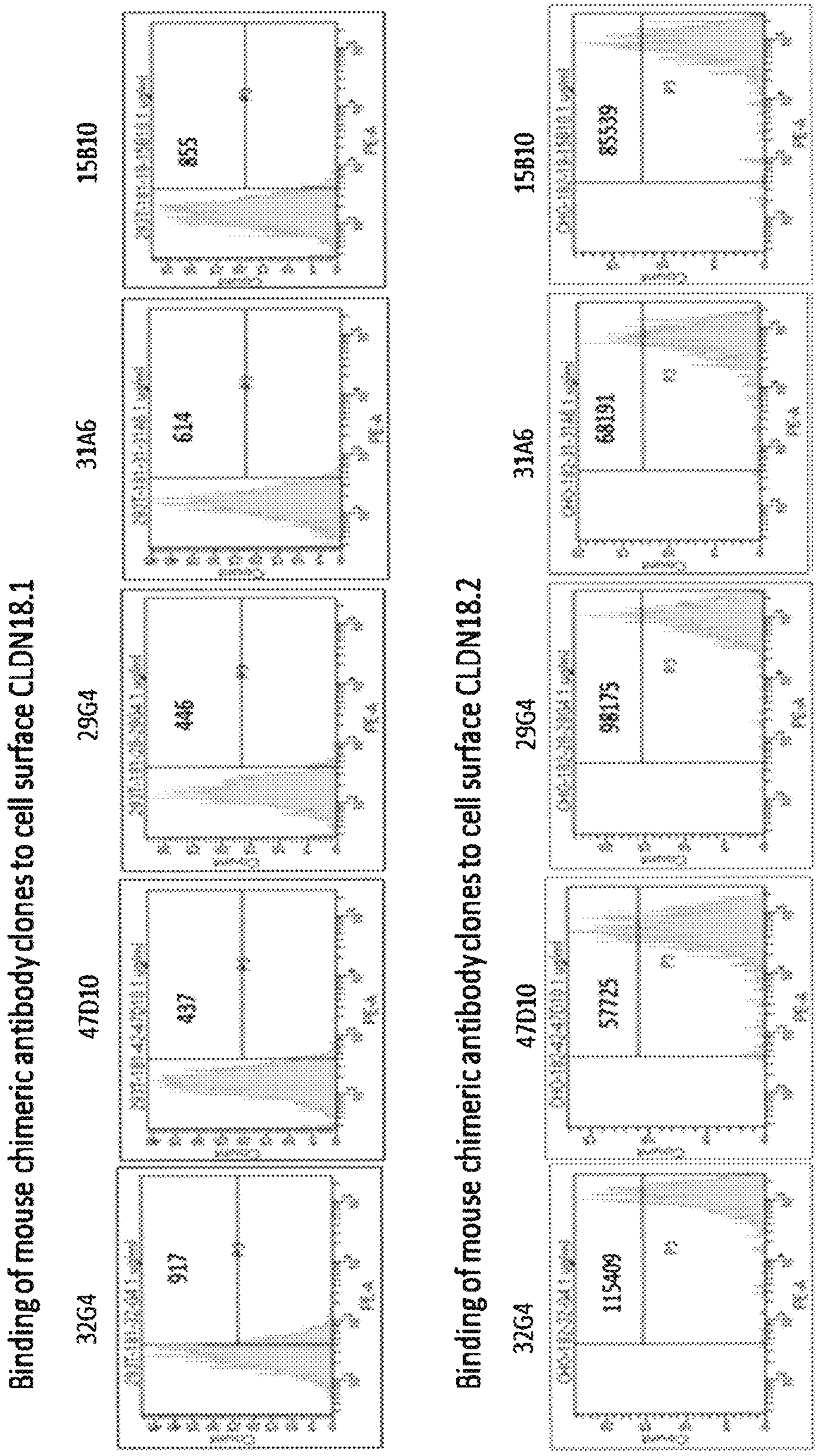
FIG. 7 shows binding of 5 select clones (32G4, 47D10, 29G4, 31A6 and 15B10) that exhibited specific binding to human CLDN18.2 as determined by FACS analysis. Top panel: Binding of mouse chimeric antibody clones to CLDN18.1 expressed at the cell surface. Bottom panel: Binding of mouse chimeric antibody clones to CLDN18.2 expressed at the cell surface.
Figure 8:
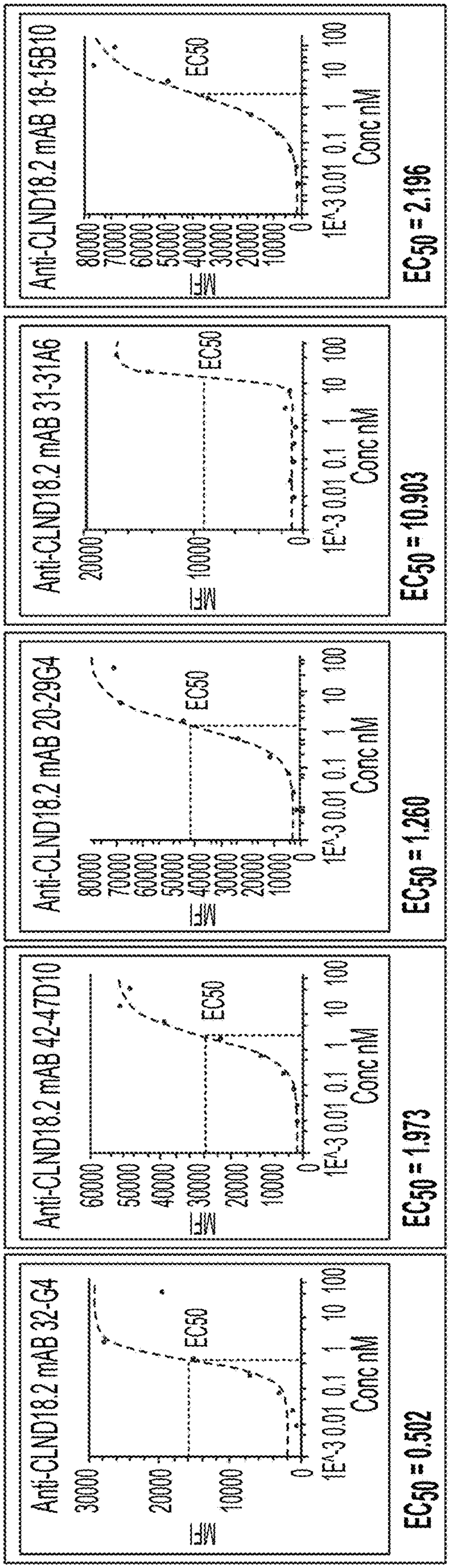
FIG. 8 shows the binding affinity of the murine anti-CLDN18.2 chimeric antibody clones 32G4, 47D10, 29G4, 31A6 and 15B10.
Figure 9A:
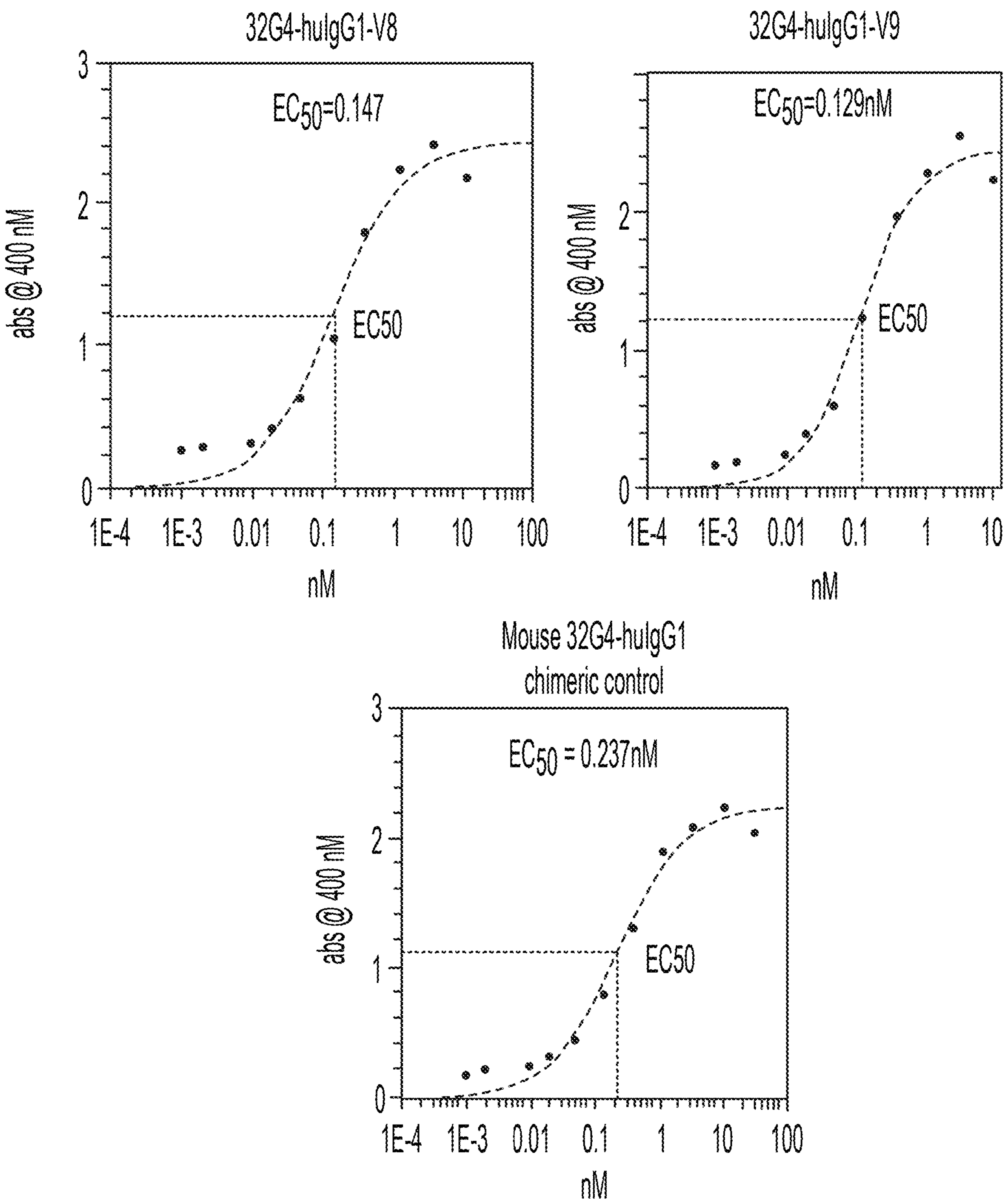
FIG. 9A shows the binding affinity of exemplary humanized 32G4 antibody variants compared to the mouse 32G4 chimeric control antibodies.
Figure 9B:
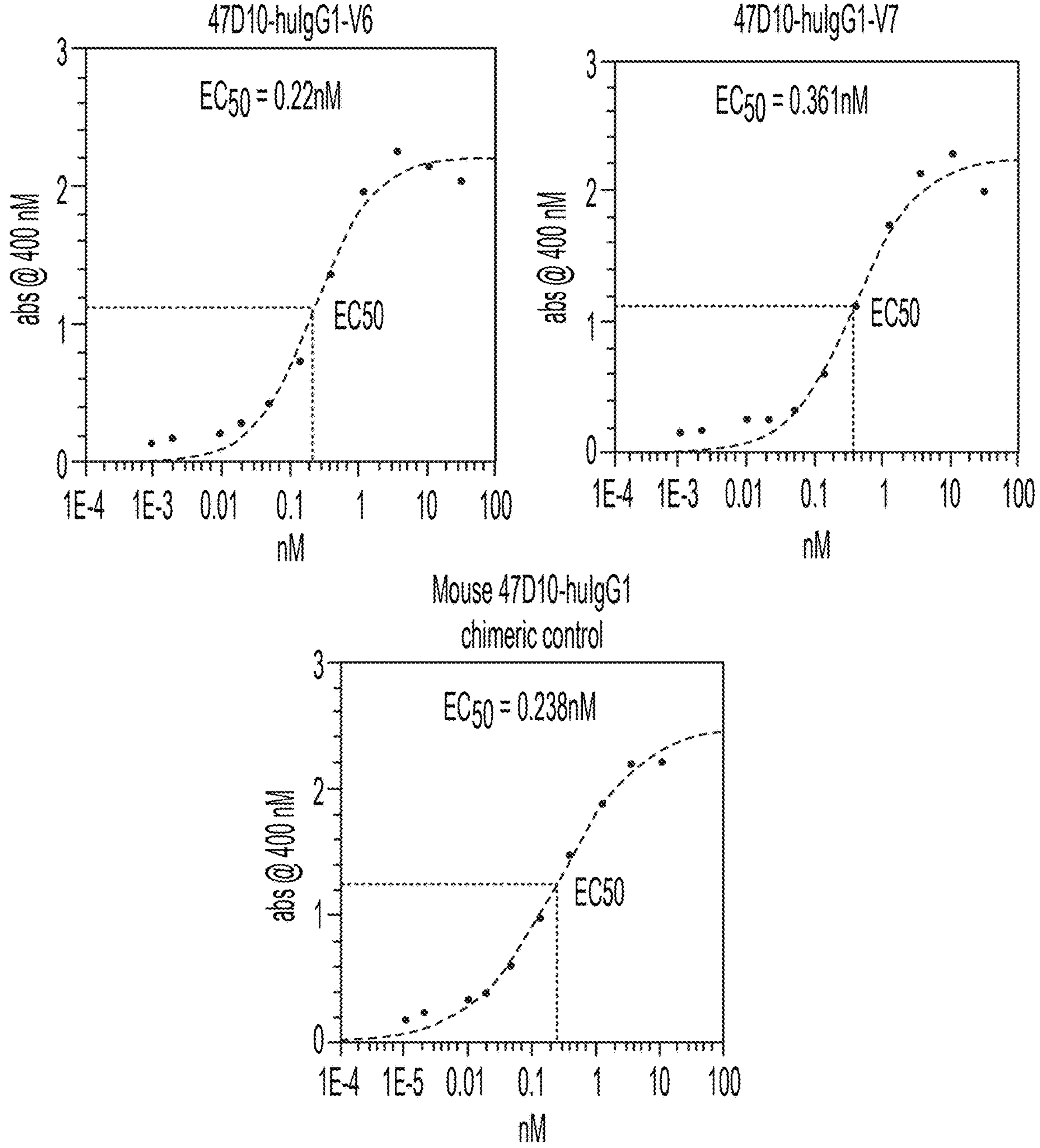
FIG. 9B shows the binding affinity of exemplary humanized 47D10 antibody variants compared to the mouse 47D10 chimeric control antibodies.

As shown in FIG. 7, the binding of murine clones 32G4, 47D10, 29G4, 31A6 and 15B10 to CLDN18.2 is at least 1000 times stronger than their respective binding to CLDN18.1 as determined by FACS analysis. The binding affinity of the five murine clones to human CLDN18.2 was further evaluated using FACS cell surface binding analysis. As shown in FIG. 8, the EC50 of the binding of 32G4, 47D10, 29G4, 31A6 and 15B10 to human CLDN18.2 was 0.502 nM, 1.973 nM, 1.260 nM, 10.903 nM and 2.196 nM, respectively. The EC50 of the binding of the 32G4-huIgG1-V8, 32G4-huIgG1-V9, 47D10-huIgG1-V6, and 47D10-huIgG1-V7 to human CLDN18.2 was 0.147 nM, 0.129 nM, 0.22 nM and 0.361 nM, respectively. See FIGS. 9A-9B. As shown in FIG. 19, humanized 32G4 and 47D10 antibody variants showed elevated binding to cynomolgus monkey and mouse claudin 18.2 target proteins compared to the IMAB362 positive control antibody.

ADCC assays. Antibody-dependent cellular cytotoxicity (ADCC) assays were performed using a bioluminescent reporter assay (Promega Cat #7015, Madison WI) in which engineered Jurkat cells with NFAT-luc and Fc-RIIIa are used as effector cells and NUGC4 gastric cancer cells as target cells. Briefly, PBMCs were cultured in complete RPMI1640 medium containing 50 ng/ml IL-2, overnight (18 hours). ADCC assay was performed according to manufacturer's instructions. Briefly, $2\times10^4$ cells of NUGC4 (target cells) were seeded into each well of a 96 well plate and cultured in 100 μl/well of complete growth medium overnight. 50 μl of the anti-CLDN18.2 antibodies were added into each well (concentration at 0, 0.001, 0.01, 0.1, 1 μg/ml). $6\times10^4$ Jurkat effector cells in 50 μl medium were added into each well. The cells were gently mixed. 21 hours later, the plate was centrifuged at 1000 rpm for 5 min. Then, 50 μl cell culture medium from each well was collected and assayed for lactate dehydrogenase (LDH) release as a measure of cell toxicity. As shown in FIG. 18, the 32G4 and 47D10 monoclonal antibodies of the present technology exhibited superior antibody-dependent cellular cytotoxicity (ADCC) compared to the IMAB362 positive control antibody.

These results demonstrate that the anti-CLDN18.2 immunoglobulin-related compositions of the present technology are useful in methods for detecting CLDN18.2 polypeptides in a biological sample.

Example 3: Characterization of In Vivo and In Vitro Cytotoxic Activities of the Anti-CLDN18.2 Antibodies of the Present Technology In vitro cancer cell killing assays (TDCC: T cell dependent cellular cytotoxicity). In vitro cancer cell killing assays were performed using the CellTiter-Glo™ luminescent cell viability assay, which monitors live cells by measuring the ATP released by viable cells. Briefly, target cells (claudin 18.2-HEK293) were seeded one day before with 10k/well in RPMI 1640 medium. The cells were cultured until they reached 50% confluence. Anti-CLDN18.2×anti-CD3 antibodies 32G4-V8×OKT3, 32G4-V9×OKT3, 47D10-V6×OKT3, and 47D10-V7×OKT3 (see FIGS. 20-21) were diluted at 1:10 serial dilutions. IMAB-362-CD3 (OKT3) was used as a positive benchmark control, and isotype-CD3 (OKT3) was used as a negative control. After removing the supernatant of the cultured target cell claudin 18.2-HEK293, 50 μl/well of the diluted antibodies were added, followed by adding 50 μl/well of the PBMCs, and the culture was kept at 37° C. for 48 hours. ATP assay was performed using the CellTiter-Glo™ kit according to manufacturer's instruction (Promega, Madison, WI). FIG. 24 shows exemplary gastric cancer cell killing (TDCC) assay data of 32G4-anti-CD3 and 47D10-anti-CD3 bispecific antibody variants, in comparison with the IMAB362-anti-CD3 benchmark antibody and the negative isotype control. As shown in FIG. 24, the CLDN18.2 bispecific antibodies of the present technology showed superior TDCC activity at concentrations as low as 0.001 nM compared with the IMAB-362-CD3 positive control antibody.

In vivo mouse xenograft model development. Gastric cancer cell line xenograft (CDX) models using Kato-III and NUGC4, in the BRG (Balb/c Rag2$^{-/-}$, IL2Rγ$^{-/-}$) mouse were developed. This mouse strain lacks adaptive immune cells and NK cells and was used for cancer cell engraftment. Twenty-five million cancer cells were implanted subcutaneously, and the tumor volume was measured twice weekly by caliper. Once the tumor reached around 1500 mm$^3$, animals were randomized for efficacy studies. Animals were divided into the following three groups. Group 1:5 experimental mice (experimental group with 32G4-V8×huSP34-v5 anti-CLDN18.2×anti-CD3; dose concentration: 5 mg/KG; injection schedule: every other day; route: IV); Group 2:5 control mice (PBS/saline; injection schedule: every other day; route: IV); Group 3: Benchmark antibody (IMAB362×anti-CD3, 5 mg/KG, injection schedule: every other day; route: IV). Tumor measurements were performed twice weekly up to 40 days post graft. FIG. 27 shows exemplary in vivo efficacy of 32G4-V8×huSP34-v5 in the mouse xenograft gastric cancer model, in comparison with the negative control (PBS). As shown in FIG. 27, the 32G4-V8×huSP34-v5 bispecific antibody showed strong inhibition of gastric tumor growth in the mouse model.

The anti-CLDN18.2 immunoglobulin-related compositions of the present technology exhibited potent in vitro and/or in vivo cytotoxic activity against CLDN18.2-associated cancers. Accordingly, the immunoglobulin-related compositions of the present technology are useful to treat a Claudin 18.2-associated cancer in a subject in need thereof.

Example 4: Stability of the Anti-CLDN18.2 Antibodies of the Present Technology

The stability of 32G4-V8×huSP34-v5 molecule was assessed in freeze/thaw (−80° C.)/(RT) cycles, and at 4° C., room temperature (25° C.) and 40° C. at 1, 3, 7 and 14 days, followed by SEC-HPLC, and TDCC cancer cell killing activity evaluation. The samples were tested in three buffer conditions (Buffer 1: 20 mM sodium citrate, 0.02% PS 80, pH 6.0; Buffer 2: 20 mM sodium citrate, 5.8% sucrose, 0.02% polysorbate 80, pH 7.2; buffer 3: PBS pH 7.4). As shown in FIG. 28, the 32G4-V8×huSP34-v5 bispecific antibody remained stable under the conditions tested, and as shown in FIG. 29, the 32G4-V8×huSP34-v5 bispecific antibody maintained cancer cell killing activity under the conditions tested.

These results demonstrate that the anti-CLDN18.2 immunoglobulin-related compositions of the present technology are stable for use in methods for detecting CLDN18.2 polypeptides in a biological sample or treating a Claudin 18.2-associated cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An antibody or antigen binding fragment thereof that binds to Claudin 18.2 (CLDN18.2), comprising a heavy chain immunoglobulin variable domain ($V_H$) and a light chain immunoglobulin variable domain ($V_L$), wherein:

(a) the $V_H$ comprises a $V_H$-complementarity-determining region (CDR) 1 sequence of SEQ ID NO: 6, a $V_H$-CDR2 sequence of SEQ ID NO: 7, and a $V_H$-CDR3 sequence of SEQ ID NO: 8, and/or the $V_L$ comprises a $V_L$-CDR1 sequence of SEQ ID NO: 9, a $V_L$-CDR2 sequence of SEQ ID NO: 10 or SEQ ID NO: 155, and a $V_L$-CDR3 sequence of SEQ ID NO: 11;

(b) the $V_H$ comprises a $V_H$-CDR1 sequence of SEQ ID NO: 12, a $V_H$-CDR2 sequence of SEQ ID NO: 13, and a $V_H$-CDR3 sequence of SEQ ID NO: 14, and/or the $V_L$ comprises a $V_L$-CDR1 sequence of SEQ ID NO: 15, a $V_L$-CDR2 sequence of SEQ ID NO: 16 or SEQ ID NO: 156, and a $V_L$-CDR3 sequence of SEQ ID NO: 17;

(c) the $V_H$ comprises a $V_H$-CDR1 sequence of SEQ ID NO: 18, a $V_H$-CDR2 sequence of SEQ ID NO: 19, and a $V_H$-CDR3 sequence of SEQ ID NO: 20, and/or the $V_L$ comprises a $V_L$-CDR1 sequence of SEQ ID NO: 21, a $V_L$-CDR2 sequence of SEQ ID NO: 22, and a $V_L$-CDR3 sequence of SEQ ID NO: 23;

(d) the $V_H$ comprises a $V_H$-CDR1 sequence of SEQ ID NO: 24, a $V_H$-CDR2 sequence of SEQ ID NO: 25, and a $V_H$-CDR3 sequence of SEQ ID NO: 26, and/or the $V_L$ comprises a $V_L$-CDR1 sequence of SEQ ID NO: 27, a $V_L$-CDR2 sequence of SEQ ID NO: 28, and a $V_L$-CDR3 sequence of SEQ ID NO: 29; or (e) the $V_H$ comprises a $V_H$-CDR1 sequence of SEQ ID NO: 30, a $V_H$-CDR2 sequence of SEQ ID NO: 31, and a $V_H$-CDR3 sequence of SEQ ID NO: 32, and/or the $V_L$ comprises a $V_L$-CDR1 sequence of SEQ ID NO: 33, a $V_L$-CDR2 sequence of SEQ ID NO: 34, and a $V_L$-CDR3 sequence of SEQ ID NO: 35.

2. The antibody or antigen binding fragment thereof of claim 1, wherein:

(a) the $V_H$ comprises an amino acid sequence that is at least 95% identical to the $V_H$ sequence of any one of SEQ ID NOs: 36, 38, 40, 42, 44, 46-49, or 54-57, and/or the $V_L$ comprises an amino acid sequence that is at least 95% identical to the $V_L$ sequence of any one of SEQ ID NOS: 37, 39, 41, 43, 45, 50-53, or 58-61; or (b) the $V_H$ comprises an amino acid sequence selected from any one of SEQ ID NOs: 36, 38, 40, 42, 44, 46-49, or 54-57; and/or (b) the $V_L$ comprises an amino acid sequence selected from any one of SEQ ID NOs: 37, 39, 41, 43, 45, 50-53, or 58-61.

3. The antibody or antigen binding fragment thereof of claim 1, comprising:

(a) a heavy chain (HC) amino acid sequence comprising SEQ ID NO: 62, SEQ ID NO: 64, SEQ ID NO: 66, SEQ ID NO: 68, or a variant thereof having one or more conservative amino acid substitutions, and/or a light chain (LC) amino acid sequence comprising SEQ ID NO: 63, SEQ ID NO: 65, SEQ ID NO: 67, SEQ ID NO: 69, or a variant thereof having one or more conservative amino acid substitutions;

(b) a HC amino acid sequence that is at least 95% identical to the HC sequence present in SEQ ID NO: 62, SEQ ID NO: 64, SEQ ID NO: 66, or SEQ ID NO: 68 and/or a LC amino acid sequence that is at least 95% identical to the LC sequence present in SEQ ID NO: 63, SEQ ID NO: 65, SEQ ID NO: 67, or SEQ ID NO: 69; or (c) a HC amino acid sequence and a LC amino acid sequence selected from the group consisting of: SEQ ID NO: 62 and SEQ ID NO: 63, SEQ ID NO: 64 and SEQ ID NO: 65, SEQ ID NO: 66 and SEQ ID NO: 67, and SEQ ID NO: 68 and SEQ ID NO: 69, respectively.

4. The antibody or antigen binding fragment thereof of claim 1, wherein the antibody or antigen binding fragment thereof binds to a Claudin 18.2 (CLDN18.2) polypeptide comprising an extracellular loop I (EL I) sequence, and wherein the extracellular loop I (ELI) sequence comprises the amino acid sequence of SEQ ID NO: 2 or the CLDN18.2 polypeptide comprises the amino acid sequence of SEQ ID NO: 4.

5. The antibody or antigen binding fragment thereof of claim 1, wherein:

(a) the antigen binding fragment is selected from the group consisting of a Fab, a F(ab')2, a Fab', a scFv, and a Fv;

(b) the antibody further comprises a Fc domain of an isotype selected from the group consisting of IgG1, IgG2, IgG3, IgG4, IgA1, IgA2, IgM, IgD, and IgE;

(c) a monoclonal antibody, a chimeric antibody, or a humanized antibody; and/or (d) a monospecific antibody, a bispecific antibody, or a multispecific antibody; and/or (e) the antibody lacks $\alpha$-1,6-fucose modifications.

6. The antibody or antigen binding fragment thereof of claim 5, comprising:

(a) an IgG 1 constant region comprising one or more amino acid substitutions selected from the group consisting of N297A, K322A, L234A, and L235A, or (b) an IgG4 constant region comprising a S228P mutation.

7. A bispecific antibody that binds to CLDN18.2, comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein:

(a) each of the first polypeptide chain and the fourth polypeptide chain comprises in the N-terminal to C-terminal direction:

(i) a light chain variable domain of a first immunoglobulin that specifically binds to a first epitope;

(ii) a light chain constant domain of the first immunoglobulin;

(iii) a flexible peptide linker comprising the amino acid sequence (GGGGS) 3 (SEQ ID NO: 79); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin specifically bind to a second epitope, and are linked together via a flexible peptide linker comprising the amino acid sequence $(GGGGS)_6$ (SEQ ID NO: 80) to form a single-chain variable fragment; and (b) each of the second polypeptide chain and the third polypeptide chain comprises in the N-terminal to C-terminal direction:

(i) a heavy chain variable domain of the first immunoglobulin that specifically binds to the first epitope; and (ii) a heavy chain constant domain of the first immunoglobulin; and wherein the heavy chain variable domain of the first immunoglobulin or the heavy chain variable domain of the second immunoglobulin is selected from (i) any one of SEQ ID NOs: 36, 38, 40, 42, 44, 46-49, or 54-57 or (ii) any one of SEQ ID NOs: 99-102, or SEQ ID NO: 157, and/or the light chain variable domain of the first immunoglobulin or the light chain variable domain of the second immunoglobulin is selected from (i) any one of SEQ ID NOs: 37, 39, 41, 43, 45, 50-53, or 58-61 or (ii) SEQ ID NO: 103 or SEQ ID NO: 158.

8. A bispecific antibody molecule comprising a first antigen binding moiety that binds to an epitope on a CLDN18.2 polypeptide comprising the antibody or antigen binding fragment thereof of claim 1 and a second antigen binding moiety that binds to a second epitope, wherein the first antigen binding moiety comprises a first heavy chain immunoglobulin variable domain ($V_H$) and a first light chain immunoglobulin variable domain ($V_L$), wherein the second antigen binding moiety comprises a second $V_H$ and a second $V_L$.

9. The antibody or antigen binding fragment thereof of claim 8, wherein the second antigen binding moiety binds to CD3, and wherein:

(a) the second $V_H$ comprises an amino acid sequence that is at least 95% identical to the $V_H$ sequence of any one of SEQ ID NOs: 97, 99, 100, 101, 102, or 157; and/or (b) the second $V_L$ comprises an amino acid sequence that is at least 95% identical to the $V_L$ sequence of any one of SEQ ID NOs: 98, 103, or 158;

(b) the second $V_H$ comprises an amino acid sequence selected from any one of SEQ ID NOS: 97, 99, 100, 101, 102, or 157; and/or (b) the second $V_L$ comprises an amino acid sequence selected from any one of SEQ ID NOs: 98, 103, or 158;

(c) (i) the first $V_H$ sequence is at least 95% identical to the $V_H$ sequence of any one of SEQ ID NOs: 36, 38, 40, 42, 44, 46-49, or 54-57; (ii) the first $V_L$ sequence is at least 95% identical to the $V_L$ sequence of any one of SEQ ID NOs: 37, 39, 41, 43, 45, 50-53, or 58-61; (iii) the second $V_H$ is at least 95% identical to the $V_H$ sequence of any one of SEQ ID NOs: 97, 99, 100, 101, 102, or 157; and/or (iv) the second $V_L$ is at least 95% identical to the $V_L$ sequence of any one of SEQ ID NOs: 98, 103, or 158; or (d) (i) the first $V_H$ comprises an amino acid sequence of the $V_H$ sequence of any one of SEQ ID NOs: 36, 38, 40, 42, 44, 46-49, or 54-57; (ii) the first $V_L$ sequence comprises an amino acid sequence of the $V_L$ sequence of any one of SEQ ID NOs: 37, 39, 41, 43, 45, 50-53, or 58-61; (iii) the second $V_H$ comprises an amino acid sequence of the $V_H$ sequence of any one of SEQ ID NOS: 97, 99, 100, 101, 102, or 157; and/or (iv) the second $V_L$ comprises an amino acid sequence of the $V_L$ sequence of any one of SEQ ID NOs: 98, 103, or 158.

10. The antibody or antigen binding fragment thereof of claim 8, wherein the second antigen binding moiety binds to CD3, and wherein the antibody or antigen binding fragment thereof comprises:

(a) a heavy chain (HC) comprising an amino acid sequence that is at least 95% identical to the HC sequence of any one of SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, SEQ ID NO: 161, and/or a light chain (LC) comprising an amino acid sequence an amino acid sequence that is at least 95% identical to the LC sequence of any one of SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, SEQ ID NO: 162;

(b) a HC comprising an amino acid sequence of any one of SEQ ID NO: 62, SEQ ID NO: 64, SEQ ID NO: 66, SEQ ID NO: 68, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 159, SEQ ID NO: 161, or a variant thereof having one or more conservative amino acid substitutions, and/or a LC comprising an amino acid sequence of any one of SEQ ID NO: 63, SEQ ID NO: 65, SEQ ID NO: 67, SEQ ID NO: 69, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 160, SEQ ID NO: 162, or a variant thereof having one or more conservative amino acid substitutions; or (c) a HC amino acid sequence and a LC amino acid sequence selected from the group consisting of: SEQ ID NO: 62 and SEQ ID NO: 63, SEQ ID NO: 64 and SEQ ID NO: 65, SEQ ID NO: 66 and SEQ ID NO: 67, SEQ ID NO: 68 and SEQ ID NO: 69, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 159 and SEQ ID NO: 160, and SEQ ID NO: 161 and SEQ ID NO: 162, respectively.

11. The antibody or antigen binding fragment thereof of claim 8, wherein the CLDN18.2 polypeptide an extracellular loop 1 (EL1) sequence, optionally wherein the extracellular loop 1 (EL1) sequence comprises the amino acid sequence of SEQ ID NO: 2 or the CLDN18.2 polypeptide comprises the amino acid sequence of SEQ ID NO: 4.

12. The antibody or antigen binding fragment thereof of claim 8, wherein the antibody or antigen binding fragment thereof binds to T cells, B-cells, myeloid cells, plasma cells, or mast-cells.

13. The antibody or antigen binding fragment thereof of claim 8, wherein the second epitope is CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

14. An anti-CD3 antibody or antigen binding fragment thereof comprising a heavy chain immunoglobulin variable domain ($V_H$) and a light chain immunoglobulin variable domain ($V_L$), wherein:

(a) the $V_H$ comprises an amino acid sequence of any one of SEQ ID NOs: 99-102, or SEQ ID NO: 157;

(b) the $V_L$ comprises an amino acid sequence of SEQ ID NO: 103 or SEQ ID NO: 158; or (c) the $V_H$ and $V_L$ comprise the amino acid sequences selected from the group consisting of: SEQ ID NO: 101 and SEQ ID NO: 103; and SEQ ID NO: 157 and SEQ ID NO: 158, respectively.

15. A recombinant nucleic acid sequence encoding the antibody or antigen binding fragment thereof of claim 1.

16. A host cell or vector comprising the recombinant nucleic acid sequence of claim 15.

17. A pharmaceutical composition comprising the antibody or antigen binding fragment thereof of claim 1 and a pharmaceutically-acceptable carrier, wherein the antibody or antigen binding fragment thereof is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

18. A method for treating cancer in a subject in need thereof, comprising administering to the subject a therapeutically effective amount of the antibody or antigen binding fragment thereof of claim 1, wherein the antibody or antigen binding fragment thereof specifically binds to Claudin 18.2 (CLDN18.2).

19. The method of claim 18, wherein the cancer is:
(a) a solid tumor; and/or
(b) selected from the group consisting of gastric cancer, esophageal cancer, pancreatic cancer, lung cancer, ovarian cancer, colon cancer, hepatic cancer, head-neck cancer, and gallbladder cancer.

20. The method of claim 18, wherein the antibody or antigen binding fragment thereof is administered to the subject separately, sequentially or simultaneously with an additional therapeutic agent.

21. The method of claim 20, wherein the additional therapeutic agent is:
(a) one or more of alkylating agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, and bisphosphonate therapy agents; and/or
(b) an immuno-modulating/stimulating antibody, optionally wherein the immuno-modulating/stimulating antibody is an anti-PD-1 antibody, an anti-PD-L1 antibody, an anti-PD-L2 antibody, an anti-CTLA-4 antibody, an anti-TIM3 antibody, an anti-4-1BB antibody, an anti-CD73 antibody, an anti-GITR antibody, or an anti-LAG-3 antibody.

22. A method for detecting cancer in a subject in vivo comprising:
(a) administering to the subject an effective amount of the antibody or antigen binding fragment thereof of claim 1, wherein the antibody or antigen binding fragment thereof is localizes binds to a cancer cell expressing a CLDN18.2 polypeptide and is labeled with a radioisotope; and
(b) detecting the presence of a tumor in the subject by detecting radioactive levels emitted by the antibody or antigen binding fragment thereof that are higher than a reference value.

23. The method of claim 18, wherein the subject is human.

24. A method for detecting Claudin 18.2 (CLDN18.2) protein expression levels in a biological sample comprising contacting the biological sample with the antibody or antigen binding fragment thereof of claim 1, and detecting binding to CLDN18.2 protein in the biological sample.

25. A chimeric antigen receptor (CAR) comprising the antibody or antigen binding fragment thereof of claim 1.

26. An engineered immune cell comprising the CAR of claim 25, optionally wherein the engineered immune cell is a B cell, a T cell, or a natural killer (NK) cell.

27. A method for treating cancer in a subject in need thereof, comprising administering to the subject a therapeutically effective amount of the engineered immune cell of claim 26.

28. The method of claim 27, wherein the cancer is:
(a) a solid tumor; or
(b) selected from the group consisting of gastric cancer, esophageal cancer, pancreatic cancer, lung cancer, ovarian cancer, colon cancer, hepatic cancer, head-neck cancer, and gallbladder cancer.

29. The anti-CD3 antibody or antigen binding fragment thereof of claim 14, wherein the antibody is a bispecific antibody or antigen binding fragment thereof.

30. A T cell comprising the anti-CD3 bispecific antibody or antigen binding fragment thereof of claim 29.

31. An ex vivo method of making a therapeutic T cell, comprising binding the anti-CD3 bispecific antibody or antigen binding fragment thereof of claim 29 to a T cell, wherein the T cell is optionally a human T cell, and wherein the binding is noncovalent.

32. A method for treating cancer in a subject in need thereof, comprising administering to the subject a therapeutically effective amount of the T cell of claim 30.

33. The anti-CD3 antibody or antigen binding fragment thereof of claim 29, wherein the bispecific antibody or antigen binding fragment thereof binds to CD3, GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125, carcinoembryonic antigen, RAGE, MART, MUC-1, MUC-2, MUC-3, MUC-4, MUC-5ac, MUC-16, MUC-17, tyrosinase, Pmel 17, GnT-V intron V sequence, Prostate cancer psm, PRAME, β-catenin, Epstein-Barr Virus nuclear antigen 1-6, LMP2, p53, lung resistance protein, Bcl-2, prostate specific antigen, Ki-67, CEACAM6, colon-specific antigen-p, HLA-DR, CD40, CD74, CD138, EGFR, EGP-1, EGP-2, VEGF, PlGF, insulin-like growth factor, tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y antigen, E-cadherin, V-cadherin, GPC3, EpCAM, CD4, CD8, CD21, CD23, CD46, CD80, HLA-DR, CD74, CD22, CD14, CD15, CD16, CD123, TCR gamma/delta, NKp46, KIR, CD56, DLL3, PD-1, PD-L1, CD28, CD137, CD99, GloboH, CD24, STEAP1, B7H3, Polysialic Acid, OX40, OX40-ligand, a peptide MHC complex comprising a peptide derived from TP53, KRAS, MYC, EBNA1-6, PRAME, MART, tyronsinase, MAGEA1-A6, pmel17, LMP2, or WT1, or a small molecule DOTA hapten.

* * * * *